US012721876B2

(12) United States Patent
Rizun

(10) Patent No.: US 12,721,876 B2
(45) **Date of Patent: *Sep. 1, 2026**

(54) ENRICHED MINERAL PITCH RESIN PRODUCTS AND METHODS OF MANUFACTURING ENRICHED MINERAL PITCH RESIN PRODUCTS

(71) Applicant: Nodari Rizun, San Diego, CA (US)

(72) Inventor: Nodari Rizun, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/599,039

(22) Filed: Mar. 7, 2024

(65) Prior Publication Data

US 2024/0216456 A1 Jul. 4, 2024

Related U.S. Application Data

(63) Continuation of application No. 18/531,571, filed on Dec. 6, 2023, which is a continuation-in-part of application No. 18/240,004, filed on Aug. 30, 2023, now Pat. No. 12,427,176, which is a continuation of application No. 17/834,654, filed on Jun. 7, 2022, now Pat. No. 11,883,454.

(60) Provisional application No. 63/197,850, filed on Jun. 7, 2021.

(51) Int. Cl.

| | |
|---|---|
| ***A61K 36/47*** | (2006.01) |
| ***A61K 31/047*** | (2006.01) |
| ***A61K 31/20*** | (2006.01) |
| ***A61K 31/201*** | (2006.01) |
| ***A61K 31/202*** | (2006.01) |
| ***A61K 31/352*** | (2006.01) |
| ***A61K 36/185*** | (2006.01) |
| ***A61K 36/48*** | (2006.01) |
| ***A61K 36/61*** | (2006.01) |
| ***A61K 36/752*** | (2006.01) |
| ***A61K 36/76*** | (2006.01) |
| ***A61K 36/835*** | (2006.01) |

(52) U.S. Cl.

CPC ............ *A61K 36/47* (2013.01); *A61K 31/047* (2013.01); *A61K 31/20* (2013.01); *A61K 31/201* (2013.01); *A61K 31/202* (2013.01); *A61K 31/352* (2013.01); *A61K 36/3482* (2024.05); *A61K 36/48* (2013.01); *A61K 36/61* (2013.01); *A61K 36/752* (2013.01); *A61K 36/76* (2013.01); *A61K 36/835* (2013.01)

(58) Field of Classification Search

None

See application file for complete search history.

(56) References Cited

U.S. PATENT DOCUMENTS

| | | | |
|---|---|---|---|
| 2008/0050500 | A1 | 2/2008 | Muranishi et al. |
| 2016/0213713 | A1 | 7/2016 | Rizun |
| 2019/0038573 | A1 | 2/2019 | Westphal et al. |

FOREIGN PATENT DOCUMENTS

| | | | |
|---|---|---|---|
| CA | 2826884 | * | 3/2014 |
| WO | WO 2016/147186 | * | 9/2016 |

OTHER PUBLICATIONS

Wilson et al., Journal of Ethnopharmacoclogy, 136, 2011, 1-9.*

Cbdiablo, 9 pages, 2024.*

Sommano et al., Molecules, 2020, 25, 5792, 16 pages.*

SecretNatureCBD, "Cannabis and Shilajit—Himalayan Wonder-Substance or Cannabinold Amplifier?", May 15, 2021 (May 15, 2021) retrieved on Aug. 11, 2022 from https://web.archive.org/web/20210515050205/htlps://secretnaturecbd.com/blogs/cbd/cannabis-and-shilajlt-himalayan-wonder-substance-or-cannabinoid-amptifier, 20 pages.

Mountaindrop, "Glycine in Shilajit", Apr. 17, 2021 (Apr. 17, 2021), retrieved on Aug. 11, 2022 from https://web.archive.org/web/20210417054623/hltps://mountaindrop.eu/glycine-in-shilajit; 5 pages.

Huchchannanavar et al., "The black seed Nigella sativa: A wonder seed" Jan. 2019 (Jan. 2019), International Journal of Chemical Studies 2019; 7(3): 1320-1324.

International Search Report and Written Opinion for PCT/US2022/032548 dated Dec. 29, 2022, 12 pages.

Shilajit Eye & Facial Mask with essential oils—Therapia By Aroma, webpage <https://www.therapiabyaroma.com/shilajit-eye-facial-mask-with-essential-oils/>, retrieved on Jun. 1, 2022, 4 pages.

Shilajit Toner—Therapia By Aroma, webpage <https://www.therapiabyaroma.com/shilajit-toner/>, retrieved on Jun. 1, 2022, 5 pages.

Lotus Blooming Herbs | Buy Pure Shilajit—Ayurvedic Supplements, https://lotusbloomingherbs.com/, Retrieved Oct. 5, 2023, 7 pages.

Pürblack Live Resin—Authentic Shilajit Resin Fulvic Acid, https://purblack.com/, Retrieved Oct. 5, 2023, 6 pages.

Genuine Shilajit Resin Sourced at High Altitude + Free Measuring Spoon, https://www.purehimalayanshilajit.com/shilajit-resin/?id=361, Retrieved Oct. 5, 2023, 15 pages.

Buy 100% Ayurvedic Shilajit Products Online In India With Discounts, https://zanducare.com/collections/shilajit, Retrieved Oct. 5, 2023, 6 pages.

Elevate Vitality with Minature Shilajit Capsules | Energy & Well-being—minaturewellness, https://www.minaturewellness.com/products/shilajit-extract, Retrieved Oct. 5, 2023, 3 pages.

Amazon.com: Altay Mummiyo Shilajit Resin with Fulvic Acid & Trace Minerals, Original Siberian Pure Shilajit with 85+ Humic Acid Supplement, Support Metabolism & Immune System—100 Serving / 50g (2 Pack), Gel : Health & Household, https://www.amazon.com/ALTAY-MUMMIYO-Shilajit-Supplement-Metabolism/dp/B0BDRPMQPP?th=1, Retrieved Oct. 5, 2023, 7 pages.

Pürblack Pure Mineral Shilajit Live Resin | Cymbiotika, https://cymbiotika.com/collections/supplements-best-sellers/products/shilajit-normaljar, Retrieved Oct. 5, 2023, 6 pages.

(Continued)

*Primary Examiner* — Michael V Meller

(74) *Attorney, Agent, or Firm* — Rimon PC

(57) ABSTRACT

Compositions and methods of manufacturing mineral pitch resin compositions comprising at least one of a cannabinoid, a terpene, a terpenoid, an essential oil and a fatty acid are provided. Such mineral pitch resin compositions may be safely consumed orally, topically or otherwise, and have numerous health benefits.

6 Claims, 3 Drawing Sheets

(56) References Cited

OTHER PUBLICATIONS

NutriHoney (30 Sticks)—Mix of Natural Shilajit Resin & Raw Honey—Healthy Nutrition Group LLC, https://naturalshilajit.com/products/nutrihoney-natural-shilajit-resin-mixed-with-rawhoney-30-sticks, Retrieved Oct. 5, 2023, 4 pages.

Siberian Green Canada, https://siberiangreen.ca/, Retrieved Oct. 5, 2023, 4 pages.

Shilajit Extract—100% Raw, Vegan Supplements—, https://www.sunfood.com/personal-care-supplements/shilajit.html, Retrieved Oct. 5, 2023, 2 pages.

Amazon.com: Nootropics Depot PrimaVie Shilajit Capsules | 250mg | 30 Count | Purified Extract | Ayurveda Supplement | Supports Mitochondrial Function + Boosts Endurance : Health & Household, https://www.amazon.com/PrimaVie-Shilajit-Supplement-Mitochondrial-Endurance/dp/B076FKT14B?th=1, Retrieved Oct. 5, 2023, 12 pages.

Buy Products by Natreon, Inc. | Sensoril Ashwagandha | PrimaVie Shilajit, https://nootropicsdepot.com/brands/Natreon%2C-Inc..html, Retrieved Oct. 5, 2023, 2 pages.

https://www.muniyalayurveda.in/products/tvakashuddi, Retrieved Oct. 5, 2023, 3 pages.

Moringo, https://www.mymoringo.com/IN/phytoshine.html, Retrieved Oct. 6, 2023, 5 pages.

Ashwashila Capsule Benefits, Dosage and Side Effects, Ayurvedic Proprietary Medicine, Nov. 4, 2017, 10 pages.

Extended European Search Report dated Jun. 10, 2025 concerning European Patent Application No. 22820911.0; 12 pp.

Health; "DeeplyRooted Dietary Supplement"; Mintel; May 22, 2019; XP055644769; 9 pp.

Frolova et al.; "Structure of Chemical 1-9Compounds, Methods of Analysis and Process A61K Control Chemical Composition of Mumijo and Methods for Determining Its Authenticity and Quality (A Review)"; Pharmaceutical Chemestry Journal; Jul. 25, 1995; XP093249060; Retrieved from the Internet URL:https://link.springer.com/content/pdf/10.1007/BF02334644.pdf; XP093249060; 5 pp.

Mintel; "Yes Life Foods: Grounding Botanical Chocolate Bar"; Mar. 17, 2016; XP093256472; 3 pp.

* cited by examiner

ENRICHED MINERAL PITCH RESIN PRODUCTS AND METHODS OF MANUFACTURING ENRICHED MINERAL PITCH RESIN PRODUCTS

CROSS-REFERENCE TO RELATED APPLICATIONS

This application is a continuation of U.S. Parent application Ser. No. 18/531,571, filed on Dec. 6, 2023, which is a continuation-in part of U.S. patent application Ser. No. 18/240,004, filed on Aug. 30, 2023, which is a continuation of U.S. patent application Ser. No. 17/834,654, filed on Jun. 7, 2022, which claims priority to and the benefit of U.S. Provisional Patent Application No. 63/197,850, filed on Jun. 7, 2021. These and all other extrinsic materials discussed herein, including publications, patent applications, and patents, are incorporated by reference in their entirety. Where a definition or use of a term in an incorporated reference is inconsistent or contrary to the definition of that term provided herein, the definition of that term provided herein applies and the definition of the term in the reference does not apply.

FIELD OF THE INVENTION

The field of the invention is mineral pitch resin, also known as shilajit, as a product for human consumption, and methods of manufacturing the same.

SUMMARY OF THE INVENTION

Mineral Pitch resin for human consumption is also known as shilajit, mumie, moomia, salajeet, and so forth. Shilajit is often associated with health benefits, and is orally consumed or topically applied by users in many countries throughout the world. Some of the health benefits associated with shilajit include, among other things, healing of skin wounds, improved circulation, improved stamina, stress relief, improved skin, hair and nails, faster tissue regeneration, anti-inflammatory properties, optimization of blood sugar levels, nootropic and performance-enhancing properties, improved sleep, would healing, increased sexual potency, improved outcome for those undergoing radiation therapy, mitigated pain, improved body homeostasis, and so forth. Shilajit can be consumed in various forms (e.g., semisolid, liquid, liquid emulsions, oils, dispersions, solid, powdered) and made into numerous consumables for human application, including orally, topically, and rectally administered products, or as drops for application into any suitable human orifice.

Unfortunately, shilajit is also one of the most adulterated and counterfeited health substances available to the public. For example, many combinations of shilajit with other botanicals do not include genuine shilajit, or the producers do not transparently disclose methods of preparing the shilajit or the botanical combinations thereof.

Furthermore, shilajit is sometimes considered to have an appalling taste and smell, which many compare to stale cow urine. The vile smell of genuine shilajit can be a major barrier for some individuals to enjoy the many health benefits of genuine shilajit resin. Still further, where genuine shilajit resin is maintained in water for a long period of time, the smell gets worse, which makes drinking it unbearable to some.

Known attempts to improve the taste and smell lead to more adulterations of shilajit or mixing it with substances like sugars, high fructose corn syrup, cheap honeys, artificial sweetener and other adulterants which take away from shilajit's quality and efficacy. Further, such efforts do not sufficiently improve the taste or smell of genuine shilajit products.

Applicant surprisingly and unexpectedly discovered methods of manufacturing shilajit products that are organoleptically attractive. A genuine shilajit product that was to be consumed for the benefits of its taste and/or smell did not exist prior to Applicant's discover. Further, the advantages of the shilajit products and methods of the disclosure go beyond just pleasant smell and taste. Applicant surprisingly discovered that consuming the shilajit products disclosed herein can change brain frequencies from Gamma to Beta to Alpha to Theta and generally maintain the brain within the range from 0.5 up to 35 Hz, depending on the formulation, time of day, and how long the specific formulation was smelled. Sending signals to the Olfactory Cortex and engaging the limbic system of the human brain through a pleasant smell of a shilajit product has never been considered in known efforts. Consuming the shilajit products disclosed herein can evoke emotions, a sense of well-being, and change the state of mind, all of which can improve health. These changes could take place in specific ways that evoke a desired health response, for example, feeling energized, feeling relaxed, increasing the sense of feeling excited or happy, improving mood, improving focus, improving relaxation, inducing a state of higher consciousness or spirituality, increasing sexual excitement and orgasmicity, and/or feeling calm, tranquil and peaceful.

In some aspects of the disclosure, a mineral pitch resin product is provided comprising a mineral pitch resin and at least one enriching ingredient, wherein the enriching ingredient comprises at lest one of a fatty acid, a cannabinoid, an essential oil, a terpene, and a terpenoid. In some aspects, a mineral pitch resin is provided comprising glycine and at least one enriching ingredient, wherein the enriching ingredient comprises at lest one of a fatty acid, a cannabinoid, an essential oil, a terpene, and a terpenoid. In some embodiments, the at least one enriching ingredient comprises at least one cannabinoid. In some embodiments, the at least one enriching ingredient comprises at least one fatty acid. In some embodiments, the at least one enriching ingredient comprises at least one essential oil. In some embodiments, the at least one enriching ingredient comprises one or more terpenes and/or terpenoids. In some embodiments, the at least one enriching ingredient comprises at least one fatty acid, at least one cannabinoid, and at least one essential oil. In some embodiments, the at least one enriching ingredient comprises at least one fatty acid, at least one cannabinoid, at least one essential oil, at least one terpene and at least one terpenoid. In some embodiments, each ingredient of the shilajit product is natural/non-synthetic. In some embodiments, the shilajit product comprises no greater than 3 mg/kg lead, no greater than 6 mg/kg arsenic, no greater than 0.5 mg/kg cadmium, no greater than 1 mg/kg mercury, less than 10 GFU/g microbiological pathogens, a moisture level by mass of 0.001 up to 60%, no less than 1% glycine, and at least 1 fatty acid. In some embodiments, the mineral pitch resin product is an orally consumable product (e.g., a paste, a tonic, a powder). In some embodiments, the mineral pitch resin product is a topical product. In some embodiments, the mineral pitch resin product is a ready to consume resin or paste product that stays emulsified with no visible separation of oil and resin when stored at 25 degrees Celsius for a period of at least one month. In some embodiments, the mineral pitch resin product is a ready to consume resin or paste product that stays emulsified with no visible separation of oil and resin when stored at 25 degrees Celsius for a period of at least three months. In some embodiments, the mineral pitch resin product is a ready to consume resin or paste product that stays emulsified with no visible separation of oil and resin when stored at 25 degrees Celsius for a period of at least six months. In some embodiments, the mineral pitch resin product is a ready to consume resin or paste product that stays emulsified with no visible separation of oil and resin when stored at 25 degrees Celsius for a period of at least one year. In some embodiments, the at least one enriching ingredient comprises all enriching ingredients present in the product, and wherein the at least one enriching ingredient comprises no more than 10% of the mineral pitch resin product by weight. In some embodiments, the at least one enriching ingredient comprises all enriching ingredients present in the product, wherein the at least one enriching ingredient consists of ingredients selected from Tables 1-4 herein, and wherein the at least one enriching ingredient comprises no more than 10% of the mineral pitch resin product by weight. In some embodiments, the mineral pitch resin product is a paste that provides a reading of between 5-8 on the Hegman gage.

In another aspect of the disclosure, a method of manufacturing a mineral pitch resin product is provided, comprising the steps of: identification of a raw mineral pitch material; collecting the raw mineral pitch material; testing the collected raw mineral pitch material for glycine; washing the collected raw material, for example, with food grade alcohol to form a washed material and placing it in containers, for example, thermo-controlled containers; removing the washed material from the containers; dissolving the washed material in sterile liquid to create a solution; filtering the solution through multiple filters to result a filtered solution; removing moisture from the filtered solution to a predetermined residual moisture level to result in a resin or paste; at a point prior to removing moisture from the filtered solution, adding at least one enriching ingredient, wherein the enriching ingredient comprises at least one of a fatty acid, a cannabinoid, an essential oil, a terpene and a terpenoid; storing the resin or paste in cold-hot storage for a period of at least 10 days wherein the temperature fluctuates; and observing the resin or paste for separation of oils beyond a threshold amount. In some embodiments, the method further comprises testing the resin or paste for the presence of glycine and at least one of fatty acids and cannabinoids. In some embodiments, the at least one enriching ingredient comprises at least one cannabinoid. In some embodiments, the at least one enriching ingredient comprises at least one fatty acid. In some embodiments, the at least one enriching ingredient comprises at least one essential oil. In some embodiments, the at least one enriching ingredient comprises at least one fatty acid, at least one cannabinoid, and at least one essential oil. In some embodiments, the at least one enriching ingredient comprises at least one fatty acid, at least one cannabinoid, at least one essential oil, at least one terpene and at least one terpenoid. In some embodiments, the resin or paste is a ready to consume product that stays emulsified with no visible separation of oil and resin when stored at 25 degrees Celsius for a period of at least one month. In some embodiments, the resin or paste is a ready to consume product stays emulsified with no visible separation of oil and resin when stored at 25 degrees Celsius for a period of at least three months. In some embodiments, the resin or paste is a ready to consume product that stays emulsified with no visible separation of oil and resin when stored at 25 degrees Celsius for a period of at least six months. In some embodiments, the resin or paste is a ready to consume product that stays emulsified with no visible separation of oil and resin when stored at 25 degrees Celsius for a period of at least one year. In some embodiments, the at least one enriching ingredient comprises all enriching ingredients present in the product, and wherein the at least one enriching ingredient comprises no more than 10% of the mineral pitch resin product by weight. In some embodiments, the at least one enriching ingredient comprises all enriching ingredients present in the product, wherein the at least one enriching ingredient consists of ingredients selected from Tables 1-4 herein, and wherein the at least one enriching ingredient comprises no more than 10% of the mineral pitch resin product by weight. In some embodiments, the mineral pitch resin product is a paste that provides a reading of between 5-8 on the Hegman gage.

In another aspect of the disclosure, a emulsified product that can be ready to consume is provided, comprising a processed mineral pitch resin including a plurality of resin molecules, and a set of enriching ingredients comprising at least a first enriching ingredient and a second enriching ingredient. The products described herein can be made using any suitable method(s), for example, the methods described further herein. The first enriching ingredient can comprise, for example, a cannabinoid, a fatty acid, an oil (e.g., an essential oil), a terpene, a terpenoid, or any other enriching ingredient. The second enriching ingredient can comprise, for example, a cannabinoid, a fatty acid, an oil (e.g., an essential oil), a terpene, a terpenoid, or any other enriching ingredient. In some aspects, at least two among a molecule of the plurality of resin molecules, a molecule of the first enriching ingredient, and a molecule of the second enriching ingredient are bound together. Without wishing to be bound by any particular theory, it is contemplated that the bonding occurs as a result of the emulsification process, for example, based on the shear forces or temperature, resulting in a new component.

In another aspect, a ready to consume emulsified product is provided, comprising a processed mineral pitch resin including a plurality of resin molecules, and a set of enriching ingredients comprising a fatty acid, an essential oil, a first terpene, and a second terpene, wherein at least two among a molecule of the plurality of resin molecules, a molecule of a first enriching ingredient of the set of enriching ingredients, and a molecule of a second enriching ingredient of the set of enriching ingredients are bound together. Any of the fatty acid, the essential oil, the first terpene, and the second terpene of the set of enriching ingredients can be the first enriching ingredient. Any of the fatty acid, the essential oil, the first terpene, and the second terpene of the set of enriching ingredients can be the second enriching ingredient.

In another aspect, a ready to consume emulsified product is provided, comprising a processed mineral pitch resin including a plurality of resin molecules, and a set of enriching ingredients comprising a cannabinoid, a fatty acid, an essential oil, a first terpene, and a second terpene, wherein at least two among a molecule of the plurality of resin molecules, a molecule of a first enriching ingredient of the set of enriching ingredients, and a molecule of a second enriching ingredient of the set of enriching ingredients are bound together. Any of the cannabinoid, the fatty acid, the essential oil, the first terpene, and the second terpene of the set of enriching ingredients can be the first enriching ingredient. Any of the cannabinoid, the fatty acid, the essential oil, the first terpene, and the second terpene of the set of enriching ingredients can be the second enriching ingredient.

The products described herein can be made using any suitable method(s), for example, the methods described further herein.

It should be appreciated that bonding resulting from the emulsification process, shearing, and/or heat can result in at least one component that is present in the emulsion (e.g., resulting from combining the mineral pitch resin with the enriching ingredients at a predetermined shear force and temperature range) but not present in any of the mineral pitch resin or enriching ingredients alone. The at least two molecules that are bound can comprise, among other things, molecule(s) of the mineral pitch resin and molecule(s) of an essential oil, molecule(s) of the mineral pitch resin and molecule(s) of a fatty acid, molecule(s) of the mineral pitch resin and molecule(s) of a cannabinoid, molecule(s) of the mineral pitch resin and molecule(s) of a terpene, molecule(s) of the mineral pitch resin and molecule(s) of a terpenoid, molecule(s) of the first and second essential oils, molecule (s) of the first and second fatty acids, molecule(s) of the first and second cannabinoids, molecule(s) of the first and second terpenes, molecule(s) of the first and second terpenoids, molecule(s) of an essential oil and molecule(s) of any other enriching ingredient, molecule(s) of a fatty acid and molecule(s) of any other enriching ingredient, molecule(s) of a cannabinoid and molecule(s) of any other enriching ingredient, molecule(s) of a terpene and molecule(s) of any other enriching ingredient, molecule(s) of a terpenoid and molecule(s) of any other enriching ingredient.

The products described herein have a highly unique organoleptic profile, and an ability to produce beneficial effects not present in shilajit resin alone, for example, to change a mood and shift brain frequencies relatively quickly. The products described herein have a highly unique organoleptic profile, and an ability to reduce undesirable quality or property associated with shilajit resin alone, for example, to change odor, taste, and/or appearance of shilajit. Without wishing to be bound by any particular theory, it is contemplated that certain combinations of terpenes in certain combinations of essential oils as described herein may contribute to or cause the change in odor, taste, and/or appearance of shilajit, or the organoleptic profile and shift the brain frequencies, for example, with the formation of terpenes bound together or cross-linked, such as diterpenes. Whether terpenes bound together or cross-linked or other terpenes form can depend on one or more factors such as reactivity, catalysts or enzymes present, conditions such as temperature and pressure, the availability of precursor compounds, physical conditions such as shear stress during the emulsification process or temperature, and other factors. Olfactory stimulation is an alternative way to pass information to the brain, and can be much quicker than through the mouth. While genuine Shilajit generally has an unpleasant smell and taste, the products described herein and the products produced using the methods described herein unexpectedly transformed the odor of silajit to have, for example, a pleasant smell and taste and results in quicker and enhanced benefits. Further, where enriching ingredients comprise one or more essential oils, it has been found that the essential oil(s) are trapped in the structure and stay preserved without going bad in terms of the smell. The emulsion form may interfere with oxygenation and deterioration, and improve viscosity.

In some embodiments, the at least two among the molecule of the plurality of resin molecules, the molecule of a first enriching ingredient of the set of essential ingredients, and the molecule of a second enriching ingredient of the set of essential ingredients are bound together. In some embodiments, the at least two among the molecule of the plurality of resin molecules, the molecule of a first enriching ingredient of the set of essential ingredients, and the molecule of a second enriching ingredient of the set of essential ingredients are chemically bound. In some embodiments, the at least two among the molecule of the plurality of resin molecules, the molecule of a first enriching ingredient of the set of essential ingredients, and the molecule of a second enriching ingredient of the set of essential ingredients are bound by a certain force such as interactions of surface tensions of molecules. In some embodiments, the at least two among the molecule of the plurality of resin molecules, the molecule of a first enriching ingredient of the set of essential ingredients, and the molecule of a second enriching ingredient of the set of essential ingredients are cross-linked. In some embodiments, the at least two among the molecule of the plurality of resin molecules, the molecule of a first enriching ingredient of the set of essential ingredients, and the molecule of a second enriching ingredient of the set of essential ingredients are bound by a chemical bonding. In some embodiments, the at least two among the molecule of the plurality of resin molecules, the molecule of a first enriching ingredient of the set of essential ingredients, and the molecule of a second enriching ingredient of the set of essential ingredients are bound by ionic bonding. In some embodiments, the at least two among the molecule of the plurality of resin molecules, the molecule of a first enriching ingredient of the set of essential ingredients, and the molecule of a second enriching ingredient of the set of essential ingredients are bound by covalent bonding. In some embodiments, the at least two among the molecule of the plurality of resin molecules, the molecule of a first enriching ingredient of the set of essential ingredients, and the molecule of a second enriching ingredient of the set of essential ingredients are bound by hydrogen bonding.

It should be appreciated that the products described herein can comprise any suitable number of enriching ingredients. In some embodiments, the first terpene and the second terpene are the same terpene. In some embodiments, the first terpene and the second terpene are different terpenes. In some embodiments, the set of enriching ingredients further comprises a third terpene different from the first terpene and the second terpene. In some embodiments, the set of enriching ingredients further comprises a fourth terpene different from the first terpene, the second terpene, and the third terpene. In some embodiments, the set of enriching ingredients further comprises a fifth terpene different from the first, second, third, and fourth terpenes. In some embodiments, the set of enriching ingredients further comprises a sixth terpene different from the first, second, third, fourth, and fifth terpenes. In some embodiments, the set of enriching ingredients further comprises five or more different terpenes. In some embodiments, the set of enriching ingredients further comprises ten or more different terpenes. In some embodiments, the set of enriching ingredients further comprises twenty or more different terpenes.

In some embodiments, the set of enriching ingredients lacks a cannabinoid. In some embodiments, the set of enriching ingredients further comprises a second cannabinoid. In some embodiments, the set of enriching ingredients further comprises a third cannabinoid. In some embodiments, the set of enriching ingredients further comprises a fourth cannabinoid. In some embodiments, the set of enriching ingredients further comprises a fifth cannabinoid. The first, second, third, fourth, and fifth cannabinoids can be the same or different cannabinoids. In some embodiments, the set of enriching ingredients further comprises a second essential oil. In some embodiments, the set of enriching ingredients further comprises a third essential oil. In some embodiments, the set of enriching ingredients further comprises a fourth essential oil. In some embodiments, the set of enriching ingredients further comprises a fifth essential oil. The first, second, third, fourth, and fifth essential oils can be the same or different essential oils. In some embodiments, the set of enriching ingredients further comprises a second fatty acid. In some embodiments, the set of enriching ingredients further comprises a third fatty acid. In some embodiments, the set of enriching ingredients further comprises a fourth fatty acid. In some embodiments, the set of enriching ingredients further comprises a fifth fatty acid. The first, second, third, fourth, and fifth fatty acids can be the same or different fatty acids. In some embodiments, the set of enriching ingredients comprises a terpenoid. In some embodiments, the set of enriching ingredients comprises two or more terpenoids.

In some embodiments, the product comprises a plurality of terpenes of different types including the first terpene and the second terpene. In some embodiments, the set of enriching ingredients comprises a plurality of terpenes of different types including the first terpene and the second terpene. In some embodiments, the first and second terpenes can be terpenes of the essential oil(s). In some embodiments, at least one of the first terpene, the second terpene, and the terpenoid comprises at least one molecule selected from the group consisting of 1,8-cineole, α-Bisabolol, α-Pinene, α-terpinyl acetate, β-Pinene, β-Sesquiphellandrene, Cafestol, Caffeine, Caryophyllene, Chamazulene, Citral, Citronellol, Cinnamaldehyde, Curcumene, Eugenol, Flavesone, Geraniol, Geranyl acetate, Germacrone, Iso-leptospermone, Leptospermone, Limonene, Linalool, Linalyl acetate, Myrcene, Nerol, Pinene, Sabinene, Terpinolene, Theobromine, Zdravets lactone, γ-Terpinene, and Zingiberene.

In some embodiments, the product is an orally consumable product. In some embodiments, the product is a topical.

In some embodiments, the product stays emulsified with no visible separation of oil and resin when stored at 25° C. for a period of at least one month. In some embodiments, the product stays emulsified with no visible separation of oil and resin when stored at 25° C. for a period of at least two months. In some embodiments, the product stays emulsified with no visible separation of oil and resin when stored at 25 ° C. for a period of at least three months. In some embodiments, the product stays emulsified with no visible separation of oil and resin when stored at 25° C. for a period of at least six months. In some embodiments, the product stays emulsified with no visible separation of oil and resin when stored at 25° C. for a period of at least nine months. In some embodiments, the product stays emulsified with no visible separation of oil and resin when stored at 25° C. for a period of at least twelve months. In some embodiments, the product stays emulsified with no visible separation of oil and resin when stored at 25° C. for a period of at least eighteen months. In some embodiments, the product stays emulsified with no visible separation of oil and resin when stored at 25° C. for a period of at least twenty-four months. In some embodiments, the product stays emulsified with no visible separation of oil and resin when stored at 25° C. for a period of at least thirty months. In some embodiments, the product stays emulsified with no visible separation of oil and resin when stored at 25° C. for a period of at least thirty-six months.

In some embodiments, the processed mineral pitch resin comprises at least 90% by weight of the product. In some embodiments, the processed mineral pitch resin itself comprises no enriching ingredients. In some embodiments, the product is a paste that provides a reading of between 5-8 on the Hegman gage. In some embodiments, the product causes an olfactory stimulation and produces a brainwave change of between 0.5 to 3 HZ, 3 to 8 HZ, 8 to 13 Hz, 12 to 15 Hz, 16 to 31 Hz, 32 to 100 Hz ranges when used. In some embodiments, the product causes an olfactory stimulation and produces a brainwave change in a human of between within 0.5 to 3 HZ, 3 to 8 HZ, 8 to 13 Hz, 12 to 15 Hz, 16 to 31 Hz, 32 to 100 Hz ranges 0.5 to 3 HZ, 3 to 8 HZ, 8 to 13 Hz, 12 to 15 Hz, 16 to 31 Hz, 32 to 100 Hz ranges within sixty seconds when used, within 3600 seconds when used, or within 43,200 seconds when used. In some embodiments, the product causes an olfactory stimulation and produces a brainwave change in a human of between within 0.5 to 3 HZ, 3 to 8 HZ, 8 to 13 Hz, 12 to 15 Hz, 16 to 31 Hz, or 32 to 100 Hz ranges within 60 seconds of use and lasting through at least 43200 seconds after use. In some embodiments, the product causes an olfactory stimulation and produces a brainwave change in a human of between within 0.5 to 3 HZ, 3 to 8 HZ, 8 to 13 Hz, 12 to 15 Hz, 16 to 31 Hz, or 32 to 100 Hz ranges within 60 seconds of use and lasting through at least 3600 seconds after use. In some embodiments, the product causes an olfactory stimulation and produces a brainwave change in a human of between within 0.5 to 3 HZ, 3 to 8 HZ, 8 to 13 Hz, 12 to 15 Hz, 16 to 31 Hz, or 32 to 100 Hz ranges within 3600 seconds of use and lasting through at least 43200 seconds after use. Use of the product can include smelling, applying topically, orally consuming, etc.

In some embodiments, the product comprises no greater than 3 mg/kg lead, no greater than 6 mg/kg arsenic, no greater than 0.5 mg/kg cadmium, no greater than 1 mg/kg mercury, less than 10 GFU/g microbiological pathogens, a moisture level by mass of 0.001 up to 60%, no less than 1% glycine; and at least 1 fatty acid.

In some aspects, the mineral pitch resin products described herein, including the mineral pitch resin products manufactured according to the methods described herein, can provide numerous benefits. For example, the mineral pitch resin products described herein can provide one, some or all of the following benefits, among others: controlling appetite, improved immune response, improved memory, improved mood, reduced pain, improved sleep, treatment of a variety of conditions like chronic pain, anxiety, epilepsy, cancer, arthritis and many others (as cannabinoids are known to treat), the healing of skin wounds, improved circulation, improved stamina, stress relief, improved skin, hair and nails, faster tissue regeneration, anti-inflammatory properties, optimization of blood sugar levels, nootropic and performance-enhancing properties, improved sleep, increased sexual potency, improved outcome for those undergoing radiation therapy, mitigated pain, improved body homeostasis, evoking of emotions, a sense of well-being, and change in the state of mind, all of which can improve health and evoke a desired health response, for example, feeling energized, feeling relaxed, increasing the sense of feeling excited or happy, improving mood, improving focus, improving relaxation, inducing a state of higher consciousness or spirituality, increasing sexual excitement and orgasmicity, and/or feeling calm, tranquil and peaceful.

BRIEF DESCRIPTION OF THE DRAWINGS

The accompanying figures, which are incorporated and constitute a part of the specification, illustrate embodiments of the invention and, together with the description, serve to explain the objects, advantages, and principles of the invention. In the drawings.

DETAILED DESCRIPTION

Figure 1:
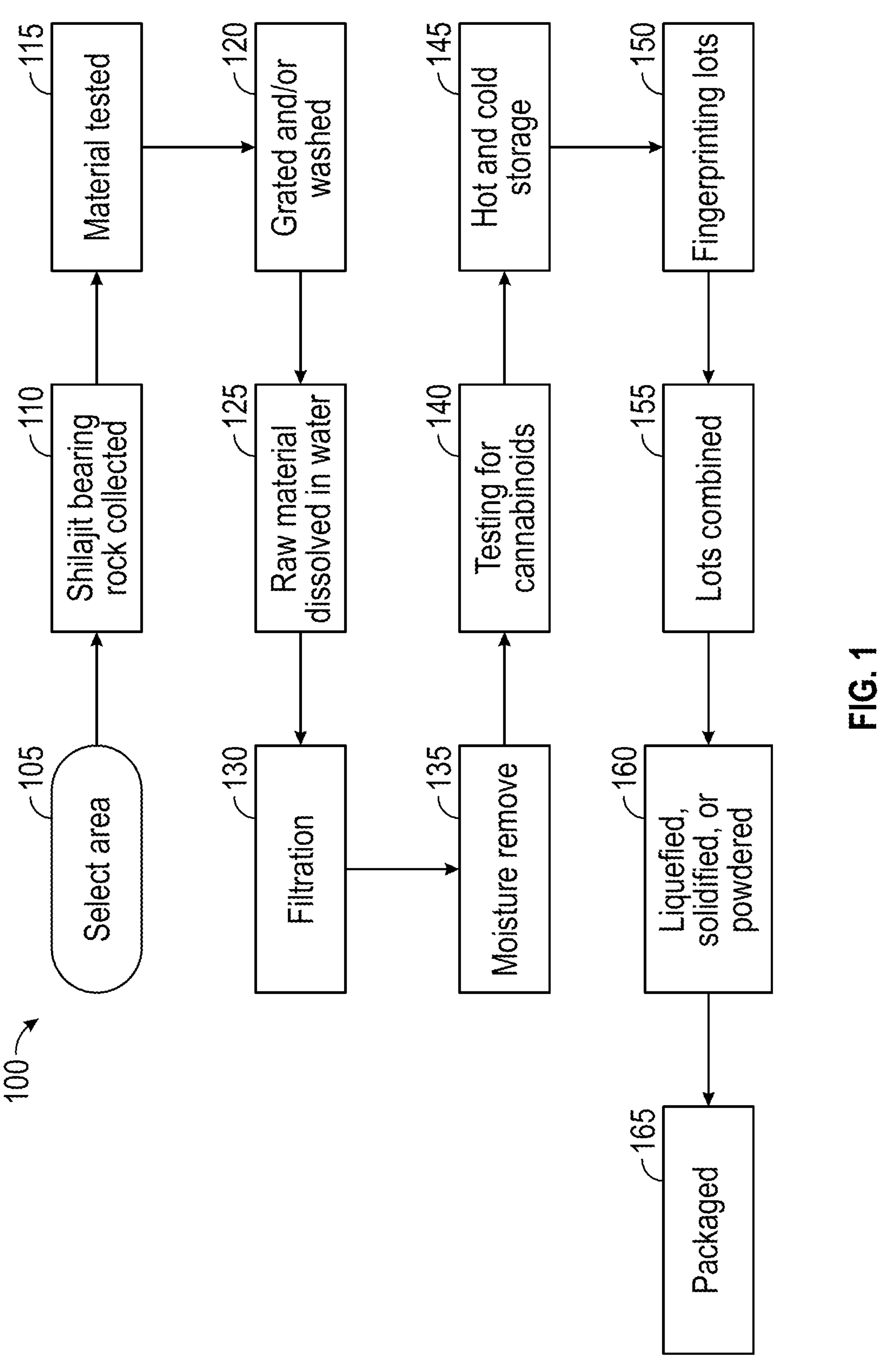
FIG. 1 is a flow diagram which shows steps and constituents in an exemplary method of creating mineral pitch resin discovering and increasing innate cannabinoid, essential oils, terpenes, or terpenoids, saturated, monounsaturated and/or polyunsaturated fatty acids content, at the same time avoiding separation of oils and the resin.

Embodiments described herein are directed to mineral pitch resin products comprising one or more cannabinoids, fatty acids (e.g., monosaturated, polyunsaturated, saturated), essential oils, terpenes, and/or terpenoids, and methods for manufacturing mineral pitch resin products with such enhancing ingredients from natural or processed sources so that the products (1) contain a homogenous combination of mineral pitch resin with cannabinoids, fatty acids (e.g., monosaturated, polyunsaturated, saturated), essential oils, terpenes, and/or terpenoids, (2) contain clinically effective amounts of cannabinoids, fatty acids (e.g., monosaturated, polyunsaturated, saturated), essential oils, terpenes, and/or terpenoids bonded with mineral pitch resin, and (3) are safe for humans to consume as a healing, adaptogenic, tonifying, and clinically effective substance with benefits of shilajit (also known as mineral pitch resin) and at least one of cannabinoids (e.g., CBD, cannabis family plant extract, hemp family plant extract), fatty acids (e.g., monosaturated, polyunsaturated, saturated), essential oils, terpenes, and/or terpenoids.

After reading this description it will become apparent to one skilled in the art how to implement the invention in various alternative embodiments and alternative applications. However, all the various embodiments of the present invention will not be described herein. It is understood that the embodiments presented here are presented by way of an example only, and not limitation. As such, this detailed description of various alternative embodiments should not be construed to limit the scope or breadth of the present invention as set forth below.

In some aspects, mineral pitch resin products including one or more of cannabinoids (e.g., major cannabinoids such cannabidiol, cannabigerol, cannabinol, tetrahydrocannabidiol; minor cannabinoids such as cannabinol, cannabichromene, tetrahydrocannabivarin) are provided herein. In some aspects, the mineral pitch resin products may be enhanced from shilajit-bearing rock, essential oils, fatty acids, terpenes and/or terpenoids.

Cannabinoids are closely tied to human physiology. Scientifically validated research shows that a human body makes its own cannabinoids and uses them to regulate homeostasis and many physiological processes. Cannabinoids are linked to appetite, immune response, memory, mood, pain, sleep, and multiple other factors in the body. Cannabinoids are of great use in treating a variety of conditions like chronic pain, anxiety, epilepsy, cancer, arthritis, and many others. Similar to the shilajit resin market, the growing cannabinoid market is replete with adulterated and misrepresented products claiming to be "CBD" while being something completely different. Cannabinoids from a Cannabis plant may not be viewed separate from other compounds found in a cannabis and or hemp plant, such as lipids made of fatty acids, aromatics known interchangeably as terpenes and terpenoids, and amino acids all being part of the plant. The cannabis plant shares these constituence with many other members of the plant kingdom.

Despite the growing popularity of shilajit, and the growing popularity of cannabinoids and similar compounds and plants, effective combinations of shilajit and cannabinoids were not known. An effective combination is very difficult to achieve due to the somewhat immiscible properties of water-soluble shilajit and oil-soluble cannabinoids or in general any other oil soluble compound, and the fairly low bioavailability of cannabinoid extracts in the human body. Known attempts to create a combination that is effective, bioavailable and has optimal final product properties until Applicant's discovery have generally failed.

Surprisingly, the inventor, an expert in manufacturing of genuine and high quality shilajit resin products with multiple U.S. Patents awarded, has solved the problem and effectively combined shilajit resin with major and minor cannabinoids, fatty acids, essential oils, terpenes, and/or terpenoids to create effective and bioavailable mineral pitch resin products comprising one or more of cannabinoids, fatty acids, essential oils, terpenes, and/or terpenoids. Since both substances (genuine shilajit resin and cannabinoids (major and minor)), achieve somewhat similar health benefits and homeostasis in the human body through different means (shilajit changes the chemical balance of the human body through the introduction of carbon-based minerals and normalizing mitochondrial metabolism, and Cannabinoids regulate human homeostatic state affecting cannabinoid receptors), it is contemplated that a combination of both substances will achieve better cumulative results with synergistic effects, higher efficacy and long-term stability. Enriching shilajit resin further (and/or alternatively to cannabinoids) with essential oils, fatty acids, terpenes, and/or terpenoids further gentrifies taste and smell of shilajit, it also adds multiple medicinal properties and physiological benefits to the combination. The unique and surprising result is that the Applicant was able to achieve excellent miscibility of water and oil soluble components, while creating novel type of shilajit resin products with minor quantity of natural and beneficial enriching additives. The final products can advantageously be targeted towards a specific physiologic response.

The inventive subject matter provides mineral pitch resin products comprising at least one of a cannabinoid, a fatty acid, an essential oil, a terpene, and terpenoid. All can be of natural or synthetic source, although natural compounds can generally be preferable in some embodiments. For example, contemplated products may include 1, 2, 3, 4, 5, at least 2, at least 3, at least 5, at least 8, at least 10, at least 15, at least 20, between 1-1,000, between 1-500, between 1-200, between 1-100, between 1-50, between 8-100, between 8-75, between 8-50, between 8-25, or any suitable number of any suitable cannabinoids, terpenes, terpenoids, essential oils and/or fatty acids set forth in Tables 1-4. In some aspects, contemplated products may include 1, 2, 3, 4, 5, at least 2, at least 3, at least 5, at least 8, at least 10, at least 15, at least 20, between 1-1,000, between 1-500, between 1-200, between 1-100, between 1-50, between 8-100, between 8-75, between 8-50, between 8-25, or any suitable number of any of the cannabinoids set forth in Table 1 and/or any of the Example compositions described herein. In some aspects, contemplated products may include 1, 2, 3, 4, 5, at least 2, at least 3, at least 5, at least 8, at least 10, at least 15, at least 20, between 1-1,000, between 1-500, between 1-200, between 1-100, between 1-50, between 8-100, between 8-75, between 8-50, between 8-25, or any suitable number of any of the terpenes and terpenoids set forth in Table 2 and/or any of the Example compositions described herein. In some aspects, contemplated products may include 1, 2, 3, 4, 5, at least 2, at least 3, at least 5, at least 8, at least 10, at least 15, at least 20, between 1-1,000, between 1-500, between 1-200, between 1-100, between 1-50, between 8-100, between 8-75, between 8-50, between 8-25, or any suitable number of any of the essential oils set forth in Table 3 and/or any of the Example compositions described herein. In some aspects, contemplated products may include 1, 2, 3, 4, 5, at least 2, at least 3, at least 5, at least 8, at least 10, at least 15, at least 20, between 1-1,000, between 1-500, between 1-200, between 1-100, between 1-50, between 8-100, between 8-75, between 8-50, between 8-25, or any suitable number of any of the fatty acids set forth in Table 4 and/or any of the Example compositions described herein.

In some aspects, contemplated products may comprise mineral pitch resin enriched with 1, 2, 3, 4, 5, at least 2, at least 3, at least 5, at least 8, at least 10, at least 15, at least 20, between 1-1,000, between 1-500, between 1-200, between 1-100, between 1-50, between 8-100, between 8-75, between 8-50, between 8-25, or any suitable number of any of the cannabinoids set forth in Table 1 and/or any of the Example compositions described herein. In some aspects, contemplated products may comprise mineral pitch resin enriched with 1, 2, 3, 4, 5, at least 2, at least 3, at least 5, at least 8, at least 10, at least 15, at least 20, between 1-1,000, between 1-500, between 1-200, between 1-100, between 1-50, between 8-100, between 8-75, between 8-50, between 8-25, or any suitable number of any of the terpenes and terpenoids set forth in Table 2 and/or any of the Example compositions described herein. In some aspects, contemplated products may comprise mineral pitch resin enriched with 1, 2, 3, 4, 5, at least 2, at least 3, at least 5, at least 8, at least 10, at least 15, at least 20, between 1-1,000, between 1-500, between 1-200, between 1-100, between 1-50, between 8-100, between 8-75, between 8-50, between 8-25, or any suitable number of any of the essential oils set forth in Table 3 and/or any of the Example compositions described herein. In some aspects, contemplated products may comprise mineral pitch resin enriched with 1, 2, 3, 4, 5, at least 2, at least 3, at least 5, at least 8, at least 10, at least 15, at least 20, between 1-1,000, between 1-500, between 1-200, between 1-100, between 1-50, between 8-100, between 8-75, between 8-50, between 8-25, or any suitable number of any of the fatty acids set forth in Table 4 and/or any of the Example compositions described herein.

TABLE 1

| | |
|---|---|
| CBDA (cannabidiolic acid) | cannabinoid |
| CBL (cannabicyclol) | cannabinoid |
| CBN (cannabinol) | cannabinoid |
| CBC (cannabichromene) | cannabinoid |
| CBCV (cannabichromevarin) | cannabinoid |
| CBD (cannabidiol) | cannabinoid |
| CBDV (cannabidivarin) | cannabinoid |
| CBE (cannabielsoin) | cannabinoid |
| CBG (cannabigerol) | cannabinoid |
| CBGM (cannabigerol monomethyl ether) | cannabinoid |
| CBGV (cannabigerovarin) | cannabinoid |
| CBT (cannabicitran) | cannabinoid |
| CBV (cannabivarin) | cannabinoid |
| THC (tetrahydrocannabinol) | cannabinoid |
| THCA (tetrahydrocannabinolic acid) | cannabinoid |
| THCC (tetrahydrocannabiorcol) | cannabinoid |
| THCP (tetrahydrocannabiphorol) | cannabinoid |
| THCV (tetrahydrocannabivarin) | cannabinoid |

TABLE 2

| | |
|---|---|
| (+)-Himachala-2,4-diene | terpene/terpenoid |
| (+)-Marsupellol | terpene/terpenoid |
| (1(10)E,4Z)-Germacrene B | terpene/terpenoid |
| (2E,4E)-Methyl abscisate | terpene/terpenoid |
| (2Z,4E)-Methyl abscisate | terpene/terpenoid |
| (2Z,4E)-Methyl phaseate | terpene/terpenoid |
| (3E,5Z)-Undeca-1,3,5-triene (Isomer 2) | terpene/terpenoid |
| (3E,6Z)-a-Farnesene | terpene/terpenoid |
| (3E,7E)-4,8,12-Trimethyltrideca-1,3,7,11-tetraene | terpene/terpenoid |
| (3Z,6E)-a-Farnesene | terpene/terpenoid |
| (3Z,9E)-Isoligustilide | terpene/terpenoid |
| (4E,6Z)-allo-Ocimene | terpene/terpenoid |
| (6Z,8E)-Megastigma-4,6,8-trien-3-one | terpene/terpenoid |
| (8a,12Z)-Abienol | terpene/terpenoid |
| (all-E)-1,7-Dimethylcyclodeca-1,4,7-triene | terpene/terpenoid |
| (all-E)-Geranylcitronellol | terpene/terpenoid |
| (all-Z)-6,9,12,15-Heneicosatetraene | terpene/terpenoid |
| (all-Z)-Methyl Docosa-4,7,10,13,16,19-hexaenoate | terpene/terpenoid |
| (all-Z)-Methyl eicosa-11,14-dienoate | terpene/terpenoid |
| (E,E)-a-Farnesene | terpene/terpenoid |
| (E,E)-Deca-2,4-dienal | terpene/terpenoid |
| (E,E)-Farnesylacetate | terpene/terpenoid |
| (E,E)-Germacradiene-11-ol | terpene/terpenoid |
| (E,E)-Megastigma-4,6,8-trien-3-one | terpene/terpenoid |
| (E,E)-Methyl 10-oxofarnesoate | terpene/terpenoid |
| (E,E)-Methyl 10,11-epoxyfarnesoate | terpene/terpenoid |
| (E,E)-Methyl farnesoate | terpene/terpenoid |
| (E,E)-Nona-2,4-dienal | terpene/terpenoid |
| (E,E)-Nona-3,6-dien-1-ol | terpene/terpenoid |
| (E) n-Propyl 1-propenyl disulfide | terpene/terpenoid |
| (E)-1,2-Dimethoxy-4-propenylbenzene | terpene/terpenoid |
| (E)-15,16-Bisnorlabda-8(17),11-dien-13-one | terpene/terpenoid |
| (E)-15,16-Bisnorlabda-8(17),12-dien-14-al | terpene/terpenoid |
| (E)-2-Decenal | terpene/terpenoid |
| (E)-2-Heptenal | terpene/terpenoid |
| (E)-2-Hexenal | terpene/terpenoid |
| (E)-2-Octenal | terpene/terpenoid |
| (E)-2,6-Dimethyl-10-(p-tolyl)-undeca-2,6-diene | terpene/terpenoid |
| (E)-2,6-Dimethylocta-1,5,7-trien-3-ol | terpene/terpenoid |
| (E)-2,6,10-Trimethylundeca-2,6-diene | terpene/terpenoid |
| (E)-3-Methylnon-2-en-4-one | terpene/terpenoid |
| (E)-4-Propenylphenol angelate | terpene/terpenoid |
| (E)-4-Propenylphenol tiglate | terpene/terpenoid |
| (E)-4,8-Dimethylnona-1,3,7-triene | terpene/terpenoid |
| (E)-a-Atlantone | terpene/terpenoid |
| (E)-a-Bisabolene | terpene/terpenoid |
| (E)-a-Damascone | terpene/terpenoid |
| (E)-Anethol epoxide | terpene/terpenoid |
| (E)-Anyl 2-methylbutyrate | terpene/terpenoid |
| (E)-Asarone | terpene/terpenoid |
| (E)-Aucantene | terpene/terpenoid |
| (E)-Aucantene | terpene/terpenoid |
| (E)-b-Caryophyllene | terpene/terpenoid |
| (E)-b-Damascenone | terpene/terpenoid |
| (E)-b-Damascone | terpene/terpenoid |
| (E)-b-Farnesene | terpene/terpenoid |
| (E)-b-Ocimene | terpene/terpenoid |
| (E)-b-Phenylethyl cinnamate | terpene/terpenoid |
| (E)-b-Santalol | terpene/terpenoid |
| (E)-Benzyl cinnamate | terpene/terpenoid |
| (E)-Biformene | terpene/terpenoid |
| (E)-Cinnamaldehyde | terpene/terpenoid |
| (E)-Cinnamyl acetate | terpene/terpenoid |

TABLE 2-continued

| | |
|---|---|
| (E)-Cinnamyl alcohol | terpene/terpenoid |
| (E)-Cinnamyl isobutyrate | terpene/terpenoid |
| (E)-Cinnamyl isovalerate | terpene/terpenoid |
| (E)-Cinnamyl propionate | terpene/terpenoid |
| (E)-Coridrin | terpene/terpenoid |
| (E)-Dendrolasin | terpene/terpenoid |
| (E)-Ectocarpene | terpene/terpenoid |
| (E)-Ethyl cinnamate | terpene/terpenoid |
| (E)-Ethyl p-methoxycinnamate | terpene/terpenoid |
| (E)-g-Atlantone | terpene/terpenoid |
| (E)-g-Bisabolene | terpene/terpenoid |
| (E)-Hex-3-en-1-ol | terpene/terpenoid |
| (E)-Isoamyl cinnamate | terpene/terpenoid |
| (E)-Isobutyl cinnamate | terpene/terpenoid |
| (E)-Isoelemicin | terpene/terpenoid |
| (E)-Isoeugenol | terpene/terpenoid |
| (E)-Isosafrol | terpene/terpenoid |
| (E)-Jasmone | terpene/terpenoid |
| (E)-Labda-7,12,14-triene | terpene/terpenoid |
| (E)-Ligustilide | terpene/terpenoid |
| (E)-m-Methoxycinnamyl alcohol | terpene/terpenoid |
| (E)-Megastigm-7-en-3,9-dione (t) | terpene/terpenoid |
| (E)-Methyl 10-hydroxy-3,7,11-trimethyldodeca-2,6,11-trienoate | terpene/terpenoid |
| (E)-Methyl 4-(geranyloxy)-cinnamate | terpene/terpenoid |
| (E)-Methyl cinnamate | terpene/terpenoid |
| (E)-Methyl p-methoxycinnamate | terpene/terpenoid |
| (E)-Multifidene | terpene/terpenoid |
| (E)-Nerolidol | terpene/terpenoid |
| (E)-Non-2-en-4-one 306 | terpene/terpenoid |
| (E)-Non-2-enal | terpene/terpenoid |
| (E)-Nuciferal | terpene/terpenoid |
| (E)-Nuciferol | terpene/terpenoid |
| (E)-o-Methoxycinnamaldehyde | terpene/terpenoid |
| (E)-o-Methoxycinnamyl alcohol | terpene/terpenoid |
| (E)-Ocimenone | terpene/terpenoid |
| (E)-Ocimenoxide | terpene/terpenoid |
| (E)-p-Methoxycinnamyl alcohol | terpene/terpenoid |
| (E)-Pseudoisoeugenyl tiglate | terpene/terpenoid |
| (E)-Pseudoisoeugenyl-2-methyl butyrate | terpene/terpenoid |
| (E)-Salvene | terpene/terpenoid |
| (E)-Tagetone | terpene/terpenoid |
| (E)-Taylopyran | terpene/terpenoid |
| (E)-trans-a-Bergamota-2,10-dien-12-al | terpene/terpenoid |
| (E)-trans-Bergamotol | terpene/terpenoid |
| (Methoxymethyl)-benzene | terpene/terpenoid |
| (Z,Z)-a-Farnesene | terpene/terpenoid |
| (Z,Z)-Methyl docosa-13,16-dienoate | terpene/terpenoid |
| (Z)-1,2-Dimethoxy-4-propenylbenzene | terpene/terpenoid |
| (Z)-2-Hexylcinnamic aldehyde | terpene/terpenoid |
| (Z)-2-Pentylcinnamaldehyde | terpene/terpenoid |
| (Z)-2,6-Dimethylocta-1,5,7-trien-3-ol | terpene/terpenoid |
| (Z)-2,6,10-Trimethylundeca-2,6-diene | terpene/terpenoid |
| (Z)-3-Butyliden-4,5,6,7-tetrahydrophthalide | terpene/terpenoid |
| (Z)-3-Hexenyl benzoate | terpene/terpenoid |
| (Z)-a-Atlantone | terpene/terpenoid |
| (Z)-a-Bisabolene | terpene/terpenoid |
| (Z)-a-Damascone | terpene/terpenoid |
| (Z)-a-Santalol | terpene/terpenoid |
| (Z)-Asarone | terpene/terpenoid |
| (Z)-b-Curcumen-12-ol | terpene/terpenoid |
| (Z)-b-Farnesene | terpene/terpenoid |
| (Z)-b-Ocimene | terpene/terpenoid |
| (Z)-b-Phenylethyl cinnamate | terpene/terpenoid |
| (Z)-b-Santalol | terpene/terpenoid |
| (Z)-Biformene | terpene/terpenoid |
| (Z)-Butylidenphthalide | terpene/terpenoid |
| (Z)-Cinnamyl propionate | terpene/terpenoid |
| (Z)-Coriandrin | terpene/terpenoid |
| (Z)-Coridrin | terpene/terpenoid |
| (Z)-Ethyl oct-5-enoate | terpene/terpenoid |
| (Z)-Ethyl p-methoxycinnamate | terpene/terpenoid |
| (Z)-Ethylcinnamate | terpene/terpenoid |
| (Z)-g-Atlantone | terpene/terpenoid |
| (Z)-g-Bisabolene | terpene/terpenoid |
| (Z)-g-Curcumen-12-ol | terpene/terpenoid |
| (Z)-g-Curcumenyl isobutyrate | terpene/terpenoid |
| (Z)-g-Curcumyl 2-methylbutyrate | terpene/terpenoid |
| (Z)-g-Curcumyl acetate | terpene/terpenoid |
| (Z)-Heptadec-8-ene | terpene/terpenoid |

TABLE 2-continued

| | |
|---|---|
| (Z)-Hex-2-en-1-ol | terpene/terpenoid |
| (Z)-Hex-3-en-1-ol | terpene/terpenoid |
| (Z)-Hex-3-enyl acetate | terpene/terpenoid |
| (Z)-Isobutyl cinnamate | terpene/terpenoid |
| (Z)-Isoelemicin | terpene/terpenoid |
| (Z)-Isoeugenol | terpene/terpenoid |
| (Z)-Jasmone | terpene/terpenoid |
| (Z)-Lanceol | terpene/terpenoid |
| (Z)-Ligustilide | terpene/terpenoid |
| (Z)-Methyl 4-(geranyloxy)-cinnamate | terpene/terpenoid |
| (Z)-Methyl cinnamate | terpene/terpenoid |
| (Z)-Methyl eicosa-11-enoate | terpene/terpenoid |
| (Z)-Methyl Heptadec-10-enoate | terpene/terpenoid |
| (Z)-Methyl p-hydroxycinnamate | terpene/terpenoid |
| (Z)-Methyl p-methoxycinnamate | terpene/terpenoid |
| (Z)-Methyl pentadec-10-enoate | terpene/terpenoid |
| (Z)-Multifidene | terpene/terpenoid |
| (Z)-Nerolidol | terpene/terpenoid |
| (Z)-Nuciferal | terpene/terpenoid |
| (Z)-Nuciferol | terpene/terpenoid |
| (Z)-Nuciferyl 2-methylbutyrate | terpene/terpenoid |
| (Z)-Nuciferyl acetate | terpene/terpenoid |
| (Z)-Nuciferyl isobutyrate | terpene/terpenoid |
| (Z)-o-Methoxycinnamaldehyde | terpene/terpenoid |
| (Z)-Ocimenone | terpene/terpenoid |
| (Z)-Ocimenoxide | terpene/terpenoid |
| (Z)-Salvene | terpene/terpenoid |
| (Z)-Tagetone | terpene/terpenoid |
| 1-(3-Methoxyphenyl)-2-(4-methoxyphenyl)-ethane | terpene/terpenoid |
| 1-(3-Methoxyphenyl)-2-phenylethane | terpene/terpenoid |
| 1-Acetoxy-4-ethylbenzene | terpene/terpenoid |
| 1-Angeloyloxyverbenone | terpene/terpenoid |
| 1-Decanol | terpene/terpenoid |
| 1-epi-a-Pinguisene | terpene/terpenoid |
| 1-epi-Cubenol | terpene/terpenoid |
| 1-Hepten-3-one | terpene/terpenoid |
| 1-Hexanol | terpene/terpenoid |
| 1-Methyl-3-(2-oxopropyl)-4-(1-methylethenyl)-cyclohexene | terpene/terpenoid |
| 1-Nonadecene | terpene/terpenoid |
| 1-Oct-3-enyl acetate | terpene/terpenoid |
| 1-Octanol | terpene/terpenoid |
| 1-Octen-3-ol | terpene/terpenoid |
| 1-Octen-3-yl 2-methylbutyrate | terpene/terpenoid |
| 1-Octen-3-yl 3-methylbutyrate | terpene/terpenoid |
| 1-Octen-3-yl isobutyrate | terpene/terpenoid |
| 1-Octen-3-yl propanoate | terpene/terpenoid |
| 1-Oxo-a-longipinene | terpene/terpenoid |
| 1-p-Menthan-8-thiol | terpene/terpenoid |
| 1-p-Menthen-8-thiol | terpene/terpenoid |
| 1-Phenyl-2-(3,5-dimethoxyphenyl)-ethane | terpene/terpenoid |
| 1-Phenylethanol | terpene/terpenoid |
| 1-Phenylethyl acetate | terpene/terpenoid |
| 1-Tetradecene | terpene/terpenoid |
| 1-Undecanol | terpene/terpenoid |
| 1,10-di-epi-Cubenol | terpene/terpenoid |
| 1,11-Oxidocalamenene | terpene/terpenoid |
| 1,2-Diacetoxy-4-allylbenzene | terpene/terpenoid |
| 1,2-Dihydro-1,1,6-trimethyl-naphthalene | terpene/terpenoid |
| 1,2-Dimethoxybenzene (Veratrol) | terpene/terpenoid |
| 1,2,4-Trimethoxybenzene | terpene/terpenoid |
| 1,3-Dimethoxybenzene | terpene/terpenoid |
| 1,3,5-Trimethyl-1,3,5-triazin-2,4,6-trione | terpene/terpenoid |
| 1,4-Dimethoxy-2-methylbenzene | terpene/terpenoid |
| 1,4-Dimethoxybenzene | terpene/terpenoid |
| 1,4-Dimethylazulene | terpene/terpenoid |
| 1,4-trans-6-Methoxyisocalamenene | terpene/terpenoid |
| 1,4a-Dimethyl-1,2,3,4,4a,5,6,7-octahydro-naphthalene | terpene/terpenoid |
| 1,5-di-epi-a-Bourbonene | terpene/terpenoid |
| 1,5-di-epi-b-Bourbonene | terpene/terpenoid |
| 1,7-Dioxaspiro[5.5]undecane | terpene/terpenoid |
| 1,8-Cineol | terpene/terpenoid |
| 1,8-Dimethyl-3-ethyl-2,9-dioxabicyclo[3.3.1]non-7-en-6-one | terpene/terpenoid |
| 1,8-Oxidocadin-4-ene | terpene/terpenoid |
| 1(10)-Spirovetivene-7b-ol | terpene/terpenoid |
| 1(10)-Valencen-7b-ol | terpene/terpenoid |
| 1(11)-Africanen-8-ol | terpene/terpenoid |
| 10-Acetoxy-4-oplopanone | terpene/terpenoid |
| 10-epi-1,8-Oxidocadina-4-ene | terpene/terpenoid |

TABLE 2-continued

| | |
|---|---|
| 10-epi-cis-Dracunculifoliol | terpene/terpenoid |
| 10-epi-Dihydroagarofuran | terpene/terpenoid |
| 10-epi-g-Eudesmol | terpene/terpenoid |
| 10-epi-Italicen-4-one | terpene/terpenoid |
| 10-epi-Italicene | terpene/terpenoid |
| 10-epi-Italicene ether | terpene/terpenoid |
| 10-epi-Junenol | terpene/terpenoid |
| 10-epi-Muurola-4,11-diene | terpene/terpenoid |
| 10-epi-trans-Dracunculifoliol | terpene/terpenoid |
| 10-Hydroxy-4-oplopanone | terpene/terpenoid |
| 10-Methyldecalin-2,7-dione | terpene/terpenoid |
| 10,11-Dihydro-a-cuparenone | terpene/terpenoid |
| 10a-Hydroxy-12-prenylguai-11-ene | terpene/terpenoid |
| 11-b-Hydroxykauren-15-a-yl acetate | terpene/terpenoid |
| 11-epi-6,10-Epoxybisabol-3-en-12-al | terpene/terpenoid |
| 11-Nordrim-8-en-12-al | terpene/terpenoid |
| 11,12-Dihydrochiloscyphone | terpene/terpenoid |
| 12-Acetoxygymnomitr-3(15)-ene | terpene/terpenoid |
| 12-epi-Cedrol | terpene/terpenoid |
| 13-epi-Manoyl oxide | terpene/terpenoid |
| 14-Hydroxy-4,5-dihydro-b-caryophyllene | terpene/terpenoid |
| 14-Hydroxy-b-caryophyllene | terpene/terpenoid |
| 14-Oxocalamenene | terpene/terpenoid |
| 15-Acetoxygymnomitr-3-ene | terpene/terpenoid |
| 15-Kaurene | terpene/terpenoid |
| 15-Nor-3-gymnomitrone | terpene/terpenoid |
| 15-Norlabdan-8-ol | terpene/terpenoid |
| 16-Atisirene | terpene/terpenoid |
| 16-Kaurene | terpene/terpenoid |
| 1a,10a-Epoxyamorph-4-ene | terpene/terpenoid |
| 1aH-Presilphiperfolan-9b-ol | terpene/terpenoid |
| 1aH,10aH-Guaia-4,6-diene | terpene/terpenoid |
| 1b-Acetoxyfurano-3-eudesmene | terpene/terpenoid |
| 1b-Acetoxyfurano-4(15)-eudesmene | terpene/terpenoid |
| 1bH-Presilphiperfolane-9a-ol | terpene/terpenoid |
| 1bH,5aH,7bH-Guaia-3,10(14)-dien-11-ol | terpene/terpenoid |
| 2-(1-Hydroxyethyl)-5-methyl-5-vinyltetrahydrofuran | terpene/terpenoid |
| 2-(2-Ethoxyethoxy)-ethanol | terpene/terpenoid |
| 2-(4-Methoxyphenyl)-5-methoxy-2,3-dihydrobenzo[b]furan | terpene/terpenoid |
| 2-(4-tert-butylbenzyl)-propione aldehyde | terpene/terpenoid |
| 2-a-Acetoxy-11-methoxyamorpha-4,7-diene | terpene/terpenoid |
| 2-a-Acetoxyamorpha-4,7(11)-dien-8-one | terpene/terpenoid |
| 2-Acetoxyfuranoelemene | terpene/terpenoid |
| 2-Allyl-4-methylphenol | terpene/terpenoid |
| 2-Allylphenol | terpene/terpenoid |
| 2-Butylfuran | terpene/terpenoid |
| 2-Decanol | terpene/terpenoid |
| 2-Decanone | terpene/terpenoid |
| 2-Dodecanol | terpene/terpenoid |
| 2-Dodecanone | terpene/terpenoid |
| 2-epi-(E)-b-Caryophyllene | terpene/terpenoid |
| 2-epi-Thujopsa-3-one | terpene/terpenoid |
| 2-Ethylbutanolide | terpene/terpenoid |
| 2-Heptanol | terpene/terpenoid |
| 2-Heptanone | terpene/terpenoid |
| 2-Himachalen-7b-ol | terpene/terpenoid |
| 2-Hydroxy-1,2-dihydrolavandulyl acetate | terpene/terpenoid |
| 2-Hydroxy-3,5-dimethoxy-9,10-dihydrophenanthrene | terpene/terpenoid |
| 2-Hydroxy-4-methoxyacetophenone | terpene/terpenoid |
| 2-Hydroxyethyl-4-methylbenzene | terpene/terpenoid |
| 2-Hydroxypinan-3-one | terpene/terpenoid |
| 2-Methyl-1-(octahydro-7,7a-dimethyl-1H-inden-1-yl)-propan-1-ol | terpene/terpenoid |
| 2-Methyl-1-(octahydro-7,7a-dimethyl-1H-inden-1-yl)-propan-1-one | terpene/terpenoid |
| 2-Methyl-1-hexanol | terpene/terpenoid |
| 2-Methyl-2-borneol | terpene/terpenoid |
| 2-Methyl-2-pentanol | terpene/terpenoid |
| 2-Methyl-2,5-divinyltetrahydrofuran | terpene/terpenoid |
| 2-Methyl-3-(4-isopropylphenyl)-propanal | terpene/terpenoid |
| 2-Methyl-3-(4-methoxyphenyl)-prop-2-ene | terpene/terpenoid |
| 2-Methyl-5-propionylfuran | terpene/terpenoid |
| 2-Methylbenzofuran | terpene/terpenoid |
| 2-Methylbutanolide | terpene/terpenoid |
| 2-Methylbutyl angelate | terpene/terpenoid |
| 2-Methylbutyl benzoate | terpene/terpenoid |
| 2-methylbutyl hexanoate | terpene/terpenoid |
| 2-Methylbutyl octanoate | terpene/terpenoid |

TABLE 2-continued

| | |
|---|---|
| 2-Methylene-6,6-dimethylcyclohex-3-ene-1-carbaldehyde | terpene/terpenoid |
| 2-n-Pentyl-g-butanolide | terpene/terpenoid |
| 2-n-Propyl-g-butanolide | terpene/terpenoid |
| 2-Nonanol | terpene/terpenoid |
| 2-Nonanone | terpene/terpenoid |
| 2-Octanol | terpene/terpenoid |
| 2-Octanone | terpene/terpenoid |
| 2-Pentadecanone | terpene/terpenoid |
| 2-Pentylfuran | terpene/terpenoid |
| 2-Phenylethyl acetate | terpene/terpenoid |
| 2-Phenylethyl butyrate | terpene/terpenoid |
| 2-Sterpurene | terpene/terpenoid |
| 2-Tridecanol | terpene/terpenoid |
| 2-Tridecanone | terpene/terpenoid |
| 2-Undecanol | terpene/terpenoid |
| 2-Undecanone | terpene/terpenoid |
| 2,2-Dimethyl-4-oxocyclohexane-1-carbaldehyde | terpene/terpenoid |
| 2,2-Dimethyl-7-isobutyl-2H,5H-pyrano[4.3-b]pyran-5-one | terpene/terpenoid |
| 2,2-Dimethyl-7-secbutyl-2H,5H-pyrano[4.3-b]pyran-5-one | terpene/terpenoid |
| 2,2,9-Trimethyl-1,6-dioxaspiro[4.4]nona-3,8-diene | terpene/terpenoid |
| 2,2',5,6-Tetramethylcyclohexanone (Isomer 1) | terpene/terpenoid |
| 2,2',5,6-Tetramethylcyclohexanone (Isomer 2) | terpene/terpenoid |
| 2,3-Dehydro-1,4-cineol | terpene/terpenoid |
| 2,3-Dehydro-1,8-cineol | terpene/terpenoid |
| 2,3-Dihydrofarnesol | terpene/terpenoid |
| 2,3-Epoxycinnamyl alcohol | terpene/terpenoid |
| 2,3,3a,4,5,6-Hexahydro-1,4-dimethylazulen-3-ol | terpene/terpenoid |
| 2,3,4-Trimethylbenzaldehyde | terpene/terpenoid |
| 2,3,5-Trimethylvalerolactone | terpene/terpenoid |
| 2,3,6-Trimethylbenzaldehyde | terpene/terpenoid |
| 2,4-Diethyloct-1-ene | terpene/terpenoid |
| 2,5-Diethyltetrahydrofuran | terpene/terpenoid |
| 2,5-Dimethoxy-4-isopropyltoluene | terpene/terpenoid |
| 2,6-Di-tert-butyl-4-methylphenol | terpene/terpenoid |
| 2,6-Diethyl-2,3-dihydro-4H-pyran-4-one | terpene/terpenoid |
| 2,6-Dimethoxycymene | terpene/terpenoid |
| 2,6,6-Trimethyl-3-oxocyclohex-1-ene-1-carbaldehyde | terpene/terpenoid |
| 2,6,6-Trimethylcyclohex-2-enone | terpene/terpenoid |
| 2,6,6-Trimethylcyclohexanone | terpene/terpenoid |
| 2,8-Dimethyl-1,7-dioxaspiro[5.5]undecane (Isomer 1) | terpene/terpenoid |
| 2,8-Dimethyl-1,7-dioxaspiro[5.5]undecane (Isomer 2) | terpene/terpenoid |
| 2,8-Epithio-cis-p-menthane | terpene/terpenoid |
| 2,8-Epoxyamorpha-4,7(11)-diene | terpene/terpenoid |
| 2a-Acetoxyamorpha-4,7(11)-diene | terpene/terpenoid |
| 2a-Hydroxy-1,8-cineol | terpene/terpenoid |
| 2a-Hydroxyamorpha-4,7(11)-diene | terpene/terpenoid |
| 2b-Acetoxyamorpha-4,7(11)-diene | terpene/terpenoid |
| 3-Acetoxy-b-ionone | terpene/terpenoid |
| 3-Acetoxyamorpha-4,7(11)-dien-8-one | terpene/terpenoid |
| 3-Acetoxytaylorione | terpene/terpenoid |
| 3-Allyl-1,4-dimethoxybenzene | terpene/terpenoid |
| 3-epi-African-5-ene | terpene/terpenoid |
| 3-Ethylacetophenone | terpene/terpenoid |
| 3-Ethylcyclohexanone | terpene/terpenoid |
| 3-exo-Acetoxyborneol | terpene/terpenoid |
| 3-exo-Acetoxybornyl acetate | terpene/terpenoid |
| 3-exo-Hydroxybornyl acetate | terpene/terpenoid |
| 3-Heptanol | terpene/terpenoid |
| 3-Hydroxy-4-methoxybenzyl alcohol | terpene/terpenoid |
| 3-Hydroxy-5,6-dihydro-b-ionone | terpene/terpenoid |
| 3-Hydroxy-b-ionone | terpene/terpenoid |
| 3-Hydroxybisabola-1(6),10-dien-2-one | terpene/terpenoid |
| 3-Methyl-4-(2,6,6-trimethylcyclohex-2-enyl)-but-3-en-2-one | terpene/terpenoid |
| 3-Methylbutanolide | terpene/terpenoid |
| 3-Methylbutyl angelate | terpene/terpenoid |
| 3-Methylbutyl isobutyrate | terpene/terpenoid |
| 3-Methylbutyl methacrylate | terpene/terpenoid |
| 3-Methylcyclohexanone | terpene/terpenoid |
| 3-Methylpentyl angelate | terpene/terpenoid |
| 3-Methylpentyl isobutyrate | terpene/terpenoid |
| 3-Octanol | terpene/terpenoid |
| 3-Octanone | terpene/terpenoid |
| 3-Phenylpropanol | terpene/terpenoid |
| 3-Thujene-10-al | terpene/terpenoid |
| 3,10-Dihydro-1,4-dimethylazulene | terpene/terpenoid |
| 3,15-a-Epoxy-4b-acetoxygymnomitrane | terpene/terpenoid |

TABLE 2-continued

| | |
|---|---|
| 3,15-b-Epoxy-4b-acetoxygymnomitrane | terpene/terpenoid |
| 3,4-Dimethoxybenzaldehyde | terpene/terpenoid |
| 3,4-Dimethoxybenzyl alcohol | terpene/terpenoid |
| 3,4-Dimethoxystyrene | terpene/terpenoid |
| 3,4-Dimethyl-5-pentyl-5H-furan-2-one | terpene/terpenoid |
| 3,4,5,6-Tetrahydro-1,4-dimethylazulene | terpene/terpenoid |
| 3,5-Dimethoxytoluene | terpene/terpenoid |
| 3,5,5-Trimethyl-4-methylenecyclohex-2-enone | terpene/terpenoid |
| 3,5,5-Trimethylcyclohex-3-enone | terpene/terpenoid |
| 3,6-Dimethyl-3-heptanol | terpene/terpenoid |
| 3,7-di-epi-Trifara-9,14-diene | terpene/terpenoid |
| 3,7-Dimethyl-3,7-dihydroxyoct-1-ene | terpene/terpenoid |
| 3(15)-Cedren-4-ol | terpene/terpenoid |
| 3a-Acetoxyamorpha-4,7(11)-diene | terpene/terpenoid |
| 3a-Acetoxybicyclogermacrene | terpene/terpenoid |
| 3a-Hydroxy-1,8-cineol | terpene/terpenoid |
| 3a-Hydroxyamorpha-4,7(11)-diene | terpene/terpenoid |
| 3b-Hydroxy-1,8-cineol | terpene/terpenoid |
| 4-(4-Hydroxyphenyl)-2-butanone | terpene/terpenoid |
| 4-(4-Hydroxyphenyl)-butan-2-ol | terpene/terpenoid |
| 4-(4-Methoxyphenyl)-butan-2-one | terpene/terpenoid |
| 4-Acetoxy-3-methoxy acetophenone | terpene/terpenoid |
| 4-Allyl-2,6-dimethoxyphenol | terpene/terpenoid |
| 4-Allyl-g-butanolide | terpene/terpenoid |
| 4-Butyl-3-methyl-g-butanolide | terpene/terpenoid |
| 4-Dehydroviridiflorol | terpene/terpenoid |
| 4-Desmethylcaryophyll-8(14)-en-5-one | terpene/terpenoid |
| 4-epi-11-Noraristola-1,9,11-triene | terpene/terpenoid |
| 4-epi-11-Noraristola-1(10),11-diene | terpene/terpenoid |
| 4-epi-11-Noraristola-9,11-diene | terpene/terpenoid |
| 4-epi-Acorenone | terpene/terpenoid |
| 4-epi-b-Patchoulene | terpene/terpenoid |
| 4-epi-Cubebol | terpene/terpenoid |
| 4-epi-Maaliol | terpene/terpenoid |
| 4-epi-Marsupellol | terpene/terpenoid |
| 4-epi-Marsupellyl acetate | terpene/terpenoid |
| 4-Ethylacetophenone | terpene/terpenoid |
| 4-Ethylguiacol | terpene/terpenoid |
| 4-Ethylphenol | terpene/terpenoid |
| 4-Hydroxy-2-methylacetophenone | terpene/terpenoid |
| 4-Hydroxy-4-methylcyclohex-2-enone | terpene/terpenoid |
| 4-Hydroxy-b-ionone | terpene/terpenoid |
| 4-Hydroxybenzaldehyde | terpene/terpenoid |
| 4-Isopropylcyclohexanol (Isomer 1) | terpene/terpenoid |
| 4-Isopropylcyclohexanol (Isomer 2) | terpene/terpenoid |
| 4-Isopropylcyclohexanone | terpene/terpenoid |
| 4-Isopropylphenol | terpene/terpenoid |
| 4-Methoxyphenylacetaldehyde | terpene/terpenoid |
| 4-Methoxyphenylacetone | terpene/terpenoid |
| 4-Methoxyphenylethanol | terpene/terpenoid |
| 4-Methoxypropiophenone | terpene/terpenoid |
| 4-Methyl-2-buten-4-olide | terpene/terpenoid |
| 4-Methyl-3-heptanol | terpene/terpenoid |
| 4-Methyl-3-heptanone | terpene/terpenoid |
| 4-n-Propylanisol | terpene/terpenoid |
| 4-Nonanol | terpene/terpenoid |
| 4-Octanol | terpene/terpenoid |
| 4-Vinylanisol | terpene/terpenoid |
| 4,5-di-epi-Aristolochene | terpene/terpenoid |
| 4,5-Dihydro-b-caryophyllen-14-al (Isomer 1) | terpene/terpenoid |
| 4,5-Dihydro-b-caryophyllen-14-al (Isomer 2) | terpene/terpenoid |
| 4,5-Dihydroxy-3-methoxy-9,10-dihydrophenanthrene | terpene/terpenoid |
| 4,8-Dimethyl-1,3,7-nonatriene (Isomer 1) | terpene/terpenoid |
| 4,8-Dimethylnona-1,3,7-triene (Isomer 2) | terpene/terpenoid |
| 4,8-Dimethylnonanol | terpene/terpenoid |
| 4(15)-Dehydroglobulol | terpene/terpenoid |
| 4a-Hydroxygermacra-1(10),5-diene | terpene/terpenoid |
| 4a-Methyloctahydronaphthalen-2-one | terpene/terpenoid |
| 4aH,10aH-Guaia-1(5),6-diene | terpene/terpenoid |
| 4b-Acetoxygymnomitr-3(15)-ene | terpene/terpenoid |
| 4b,5b-Diacetoxygymnomitr-3(15)-ene | terpene/terpenoid |
| 4bH,10aH-Guaia-1(5),6-diene | terpene/terpenoid |
| 4bH,5aH-cis-Eudesm-6-en-11-ol | terpene/terpenoid |
| 5-Acetoxybornan-2-one | terpene/terpenoid |
| 5-Acetoxylinalool | terpene/terpenoid |
| 5-epi-Aristolochene | terpene/terpenoid |
| 5-epi-Laurene | terpene/terpenoid |
| 5-epi-Pinguisenol | terpene/terpenoid |
| 5-Ethyl-2-methyl-2-vinyltetrahydrofuran | terpene/terpenoid |
| 5-Ethylcyclopent-1-enecarbaldehyde | terpene/terpenoid |

TABLE 2-continued

| | |
|---|---|
| 5-Formyl-2-hydroxy-(3-hydroxy-3-methylbutyro)-phenone | terpene/terpenoid |
| 5-Formyl-2-hydroxy-(3-methylbutyro)-phenone | terpene/terpenoid |
| 5-Guaiene-11-ol | terpene/terpenoid |
| 5-Hydroxymarsupellol | terpene/terpenoid |
| 5-Hydroxymarsupellyl acetate | terpene/terpenoid |
| 5-Methylcyclohex-2-en-1-one | terpene/terpenoid |
| 5-Methylfurfural | terpene/terpenoid |
| 5-Methylheptan-2,4-dione | terpene/terpenoid |
| 5-Methyloctahydrofuro[3,2-b]oxepine | terpene/terpenoid |
| 5-Pentyl-3,4,5-trimethyl-5H-furan-2-one | terpene/terpenoid |
| 5,5-Dimethyl-1-vinylbicyclo-[2.1.1]hexane | terpene/terpenoid |
| 5,5-Dimethylbut-3-enolide | terpene/terpenoid |
| 5,5-Dimethylcyclohex-2-en-1,4-dione | terpene/terpenoid |
| 5,6-Dehydroalaskene | terpene/terpenoid |
| 5,6-Dihydro-1,4-dimethylazulene | terpene/terpenoid |
| 5,7-Dimethylocta-l,6-diene | terpene/terpenoid |
| 5,8-Cyclocaryophyllan-4-ol | terpene/terpenoid |
| 5,8a-Dimethyl-3,4,4a,7,8,8a-hexahydro-1H-naphthalen-2-one | terpene/terpenoid |
| 5,9-Epoxyamorpha-3,7(11)-diene | terpene/terpenoid |
| 5b-Acetoxy-gymnomitr-3(15)-ene | terpene/terpenoid |
| 6-Acetoxy-p-menta-1,8-diene | terpene/terpenoid |
| 6-Acetoxy-p-mentha-1(7),8-diene (Isomer 1) | terpene/terpenoid |
| 6-Acetoxy-p-mentha-1(7),8-diene (Isomer 2) | terpene/terpenoid |
| 6-Camphenone | terpene/terpenoid |
| 6-epi-a-Cubebene | terpene/terpenoid |
| 6-epi-b-Cubebene | terpene/terpenoid |
| 6-epi-Cubenol | terpene/terpenoid |
| 6-Ethyl-2-methyl-2,3-dihydro-4H-pyran-2-one | terpene/terpenoid |
| 6-Hexyl-5,6-dihydropyran-2-one | terpene/terpenoid |
| 6-Himachalen-9b-ol | terpene/terpenoid |
| 6-Methoxythymol isobutyrate | terpene/terpenoid |
| 6-Methyl-2-heptanol | terpene/terpenoid |
| 6-Methyl-6-(3-methylphenyl)-2-heptanone | terpene/terpenoid |
| 6-Methylhept-5-en-2-ol (Sulcatol) | terpene/terpenoid |
| 6-Methylhept-5-en-2-one | terpene/terpenoid |
| 6-Methylhept-5-enal | terpene/terpenoid |
| 6-Methylheptan-2,4-dione | terpene/terpenoid |
| 6,10-Epoxybisabol-2-en-12-al | terpene/terpenoid |
| 6,10-Epoxybisabol-3-en-12-al | terpene/terpenoid |
| 6,10,14-Trimethylpentadecan-2-one | terpene/terpenoid |
| 6,11-Epoxyeudesmane | terpene/terpenoid |
| 6,11-Epoxyisodaucane | terpene/terpenoid |
| 6,7-seco-Eudesm-7(11)-en-6-al | terpene/terpenoid |
| 6a-Hydroxyeudesm-11-ene | terpene/terpenoid |
| 6a-Hydroxygermacra-1(10),4-diene | terpene/terpenoid |
| 6b-Acetoxyeudesm-4(15)-en-7b-ol | terpene/terpenoid |
| 6b-Hydroxyeudesm-11-ene | terpene/terpenoid |
| 7-Acetoxyelema-1,3-dien-8-ol | terpene/terpenoid |
| 7-Acetoxyelema-1,3,8-triene | terpene/terpenoid |
| 7-epi-1,2-Dehydrosesquicineole | terpene/terpenoid |
| 7-epi-a-Cedrene | terpene/terpenoid |
| 7-epi-a-Eudesmol | terpene/terpenoid |
| 7-epi-a-Selinene | terpene/terpenoid |
| 7-epi-b-Bisabolol | terpene/terpenoid |
| 7-epi-Bisabol-1-one | terpene/terpenoid |
| 7-epi-Bourbon-3-ene 5,11-oxide | terpene/terpenoid |
| 7-epi-Cadina-1(10),11-diene | terpene/terpenoid |
| 7-epi-Eremophila-1(10),8,11-triene | terpene/terpenoid |
| 7-epi-Helifolene | terpene/terpenoid |
| 7-epi-Sesquithujene | terpene/terpenoid |
| 7-Hydroxyeudesm-4-en-6-one | terpene/terpenoid |
| 7-Hydroxyhotrienol | terpene/terpenoid |
| 7,10-Anhydro-11,12-dihydrochiloscypholone | terpene/terpenoid |
| 7,11-Dimethylheptadecane | terpene/terpenoid |
| 7,11-Epoxymegastigm-5-en-9-one | terpene/terpenoid |
| 7,14-Anhydroamorpha-4,9-diene | terpene/terpenoid |
| 7,8-Dehydro-a-acoradiene | terpene/terpenoid |
| 7,8-Dihydro-b-ionol | terpene/terpenoid |
| 7,8-Dihydro-b-ionone | terpene/terpenoid |
| 7aH-Silphiperfol-5-ene | terpene/terpenoid |
| 7aH,10bH-Cadina-1(6),4-diene | terpene/terpenoid |
| 7b-Hydroxyamorpha-4,11-diene | terpene/terpenoid |
| 7bH-Silphiperfol-5-ene | terpene/terpenoid |
| 7bH,10bH-Cadina-1(6),4-diene | terpene/terpenoid |
| 8-Acetoxyelemol | terpene/terpenoid |
| 8-Dehydrothymol isobutyrate | terpene/terpenoid |
| 8-Hydroxybicyclogermacrene | terpene/terpenoid |
| 8-Hydroxylinalool | terpene/terpenoid |

TABLE 2-continued

| | |
|---|---|
| 8-Hydroxylinalyl 2-methylbutyrate | terpene/terpenoid |
| 8-Hydroxylinalyl isobutyrate | terpene/terpenoid |
| 8-Hydroxylinalyl propionate | terpene/terpenoid |
| 8-Hydroxylinalyl tiglate | terpene/terpenoid |
| 8,14-Cedrane oxide | terpene/terpenoid |
| 8,9-Dehydrothymol | terpene/terpenoid |
| 8,9-Dehydrothymol acetate | terpene/terpenoid |
| 8,9-Didehydrocycloisolongifolene | terpene/terpenoid |
| 8,9-Epoxyselina-4,11-diene | terpene/terpenoid |
| 8a-Hydroxyeudesma-3,11-diene | terpene/terpenoid |
| 8bH-Cedran-9-one | terpene/terpenoid |
| 9-epi-Polygodial | terpene/terpenoid |
| 9-epi-Sclarene | terpene/terpenoid |
| 9a-Hydroxyamorpha-4,7(11)-diene | terpene/terpenoid |
| 9a,11-Epoxy-1bH,5aH,7bH,9bH-guaia-3,10(14)-diene | terpene/terpenoid |
| a-Acoradiene | terpene/terpenoid |
| a-Acorenol | terpene/terpenoid |
| a-Agarofuran | terpene/terpenoid |
| a-Alasken-6-ol | terpene/terpenoid |
| a-Alasken-8-ol | terpene/terpenoid |
| a-Alaskene | terpene/terpenoid |
| a-Alaskene-8-ol | terpene/terpenoid |
| a-Ambrinol (Isomer 1) | terpene/terpenoid |
| a-Ambrinol (Isomer 2) | terpene/terpenoid |
| a-Amorphene | terpene/terpenoid |
| a-Barbatenal | terpene/terpenoid |
| a-Barbatene | terpene/terpenoid |
| a-Bisabolol | terpene/terpenoid |
| a-Bourbonene | terpene/terpenoid |
| a-Bulnesene | terpene/terpenoid |
| a-Cadinene | terpene/terpenoid |
| a-Cadinol | terpene/terpenoid |
| a-Calacorene | terpene/terpenoid |
| a-Campholenal | terpene/terpenoid |
| a-Campholenic acid | terpene/terpenoid |
| a-Campholenol | terpene/terpenoid |
| a-Campholenyl formate | terpene/terpenoid |
| a-Cedrene | terpene/terpenoid |
| a-Cedrene oxide | terpene/terpenoid |
| a-Chamigrene | terpene/terpenoid |
| a-Copaen-8-ol | terpene/terpenoid |
| a-Copaene | terpene/terpenoid |
| a-Corocalen | terpene/terpenoid |
| a-Costol | terpene/terpenoid |
| a-Cubebene | terpene/terpenoid |
| a-Cuparenone | terpene/terpenoid |
| a-Cuprenene | terpene/terpenoid |
| a-Cyclocitral | terpene/terpenoid |
| a-Cyperone | terpene/terpenoid |
| a-Dehydroelsholtzia ketone | terpene/terpenoid |
| a-Duprezianene | terpene/terpenoid |
| a-Elemene | terpene/terpenoid |
| a-Eudesmol | terpene/terpenoid |
| a-Fenchene | terpene/terpenoid |
| a-Fenchol | terpene/terpenoid |
| a-Funebrene | terpene/terpenoid |
| a-Gorgonene | terpene/terpenoid |
| a-Guaiene | terpene/terpenoid |
| a-Guaiol | terpene/terpenoid |
| a-Gurjunene | terpene/terpenoid |
| a-Helmiscapene | terpene/terpenoid |
| a-Herbertenol | terpene/terpenoid |
| a-Himachalene | terpene/terpenoid |
| a-Humulene | terpene/terpenoid |
| a-Ionone | terpene/terpenoid |
| a-Ionone epoxide (Isomer 1) | terpene/terpenoid |
| a-Ionone epoxide (Isomer 2) | terpene/terpenoid |
| a-Isocomene | terpene/terpenoid |
| a-Longipinene | terpene/terpenoid |
| a-Maalinene | terpene/terpenoid |
| a-Microbiotene | terpene/terpenoid |
| a-Muurolene | terpene/terpenoid |
| a-Neocallitropsene | terpene/terpenoid |
| a-Neoclovene | terpene/terpenoid |
| a-Panasinsene | terpene/terpenoid |
| a-Patchoulene | terpene/terpenoid |
| a-Phellandrene | terpene/terpenoid |
| a-Pinene | terpene/terpenoid |
| a-Pinene epoxide (Isomer 1) | terpene/terpenoid |
| a-Pinene epoxide (Isomer 2) | terpene/terpenoid |

TABLE 2-continued

| | |
|---|---|
| a-Pinguisene | terpene/terpenoid |
| a-Santalene | terpene/terpenoid |
| a-Santalol acetate | terpene/terpenoid |
| a-Selinene | terpene/terpenoid |
| a-Sinensal | terpene/terpenoid |
| a-Taylorione | terpene/terpenoid |
| a-Terpinene | terpene/terpenoid |
| a-Terpineol | terpene/terpenoid |
| a-Terpinyl acetate | terpene/terpenoid |
| a-Thujene | terpene/terpenoid |
| a-Thujone | terpene/terpenoid |
| a-Turmerone | terpene/terpenoid |
| a-Vetispirene | terpene/terpenoid |
| a-Vetivone | terpene/terpenoid |
| a-Ylangene | terpene/terpenoid |
| Abieta-7,13-diene | terpene/terpenoid |
| Abieta-8(14),13(15)-diene | terpene/terpenoid |
| Abietal | terpene/terpenoid |
| Abietatriene | terpene/terpenoid |
| Acetophenone | terpene/terpenoid |
| Acetoxycedren-13-ol | terpene/terpenoid |
| Aciphyllene | terpene/terpenoid |
| Acora-2,4(15)-dien-11-ol | terpene/terpenoid |
| Acora-3,10(14)-diene | terpene/terpenoid |
| Acora-3,5-dien-l l-ol | terpene/terpenoid |
| Acora-3,5-diene | terpene/terpenoid |
| Acora-3,7(11)-dien-6-ol | terpene/terpenoid |
| Acora-3,7(11)-dien-8-one | terpene/terpenoid |
| Acora-3,9-diene | terpene/terpenoid |
| Acora-7(11),9-dien-2-one | terpene/terpenoid |
| Acorenol | terpene/terpenoid |
| Acorenol B | terpene/terpenoid |
| Acorenone | terpene/terpenoid |
| Acorenone B | terpene/terpenoid |
| Acutifolene A | terpene/terpenoid |
| Acutifolene B | terpene/terpenoid |
| Africa-1,5-diene | terpene/terpenoid |
| African-1-ene | terpene/terpenoid |
| African-2-ene | terpene/terpenoid |
| African-2(6)-ene | terpene/terpenoid |
| African-3-ene | terpene/terpenoid |
| African-3(15)-ene | terpene/terpenoid |
| African-5-ene | terpene/terpenoid |
| Africanone | terpene/terpenoid |
| Agarospirol | terpene/terpenoid |
| Alantolactone | terpene/terpenoid |
| Albanone | terpene/terpenoid |
| Albene | terpene/terpenoid |
| Albicanol | terpene/terpenoid |
| Alismol | terpene/terpenoid |
| allo-Aromadendr-9-ene | terpene/terpenoid |
| allo-Aromadendra-4(15),10(14)-diene | terpene/terpenoid |
| allo-Aromadendrene | terpene/terpenoid |
| allo-Aromadendrene epoxide | terpene/terpenoid |
| allo-Davanone | terpene/terpenoid |
| allo-Himachalol | terpene/terpenoid |
| allo-Isolongifolene | terpene/terpenoid |
| allo-Ocimene | terpene/terpenoid |
| Allyl-2,4-di-acetoxybenzene | terpene/terpenoid |
| Amberone | terpene/terpenoid |
| Ambrettolide | terpene/terpenoid |
| Ambrox | terpene/terpenoid |
| Amorph-4-en-10a-ol | terpene/terpenoid |
| Amorpha-2,4,7(11)-triene | terpene/terpenoid |
| Amorpha-4-en-7-ol | terpene/terpenoid |
| Amorpha-4,11-diene | terpene/terpenoid |
| Amorpha-4,7-dien-11-ol | terpene/terpenoid |
| Amorpha-4,7(11)-dien-2-one | terpene/terpenoid |
| Amorpha-4,7(11)-dien-3-one | terpene/terpenoid |
| Amorpha-4,7(11)-dien-8-one | terpene/terpenoid |
| Amorpha-4,7(11)-diene | terpene/terpenoid |
| Amorpha-4,9-dien-14-al | terpene/terpenoid |
| Amorpha-4,9-dien-2-ol | terpene/terpenoid |
| Anastreptene | terpene/terpenoid |
| Anhydroencecalinol | terpene/terpenoid |
| Aphidicol-15-ene | terpene/terpenoid |
| Aphidicol-16-ene | terpene/terpenoid |
| Apiol | terpene/terpenoid |
| ar-Bisabolol | terpene/terpenoid |
| ar-Curcumen-15-al | terpene/terpenoid |

TABLE 2-continued

| | |
|---|---|
| ar-Curcumen-7-ol | terpene/terpenoid |
| ar-Curcumene | terpene/terpenoid |
| ar-Himachalene | terpene/terpenoid |
| ar-Tenuifolene | terpene/terpenoid |
| ar-Turmerone | terpene/terpenoid |
| Aristol-1(10)-en-12-al | terpene/terpenoid |
| Aristol-1(10)-en-12-ol | terpene/terpenoid |
| Aristola-1(10),8-diene | terpene/terpenoid |
| Aristolene | terpene/terpenoid |
| Aristolochene | terpene/terpenoid |
| Aromadendr-9-ene | terpene/terpenoid |
| Aromadendra-1(10),3-diene | terpene/terpenoid |
| Aromadendra-1(10),4-diene | terpene/terpenoid |
| Aromadendra-1(10),4(15)-diene | terpene/terpenoid |
| Aromadendra-4,10(14)-diene | terpene/terpenoid |
| Aromadendra-4,9-diene | terpene/terpenoid |
| Aromadendra-4(15),10(14)-dien-1-ol | terpene/terpenoid |
| Aromadendran-12-ol | terpene/terpenoid |
| Aromadendran-14-ol | terpene/terpenoid |
| Aromadendran-5-ol | terpene/terpenoid |
| Aromadendrene | terpene/terpenoid |
| Artedouglasia oxide A | terpene/terpenoid |
| Artedouglasia oxide B | terpene/terpenoid |
| Artedouglasia oxide C | terpene/terpenoid |
| Artedouglasia oxide D | terpene/terpenoid |
| Artemiseol | terpene/terpenoid |
| Artemisia alcohol | terpene/terpenoid |
| Artemisia ketone | terpene/terpenoid |
| Artemisiatriene | terpene/terpenoid |
| Artemisylacetate | terpene/terpenoid |
| Asterisca-3(15),6-diene | terpene/terpenoid |
| Atractylone | terpene/terpenoid |
| Atranol | terpene/terpenoid |
| Avocadynofuran | terpene/terpenoid |
| Axenol (Gleenol) | terpene/terpenoid |
| Axinyssene | terpene/terpenoid |
| b-Acoradiene | terpene/terpenoid |
| b-Acorenol | terpene/terpenoid |
| b-Alaskene | terpene/terpenoid |
| b-Atlantol (Isomer 1) | terpene/terpenoid |
| b-Atlantol (Isomer 2) | terpene/terpenoid |
| b-Barbatene | terpene/terpenoid |
| b-Bazzanene | terpene/terpenoid |
| b-Bisabolene | terpene/terpenoid |
| b-Bisabolol | terpene/terpenoid |
| b-Bourbonene | terpene/terpenoid |
| b-Bulnesene | terpene/terpenoid |
| b-Cadinene | terpene/terpenoid |
| b-Calacorene | terpene/terpenoid |
| b-Caryophyllene oxide | terpene/terpenoid |
| b-Cedrene | terpene/terpenoid |
| b-Cedrene epoxide | terpene/terpenoid |
| b-Chamigrene | terpene/terpenoid |
| b-Citronellene | terpene/terpenoid |
| b-Copaene | terpene/terpenoid |
| b-Costol | terpene/terpenoid |
| b-Cubebene | terpene/terpenoid |
| b-Curcumene | terpene/terpenoid |
| b-Cyclocitral | terpene/terpenoid |
| b-Duprezianene | terpene/terpenoid |
| b-Elemene | terpene/terpenoid |
| b-Eudesmol | terpene/terpenoid |
| b-Funebrene | terpene/terpenoid |
| b-Funebrene epoxide | terpene/terpenoid |
| b-Gorgonene | terpene/terpenoid |
| b-Helmiscapene | terpene/terpenoid |
| b-Herbertenol | terpene/terpenoid |
| b-Himachalene | terpene/terpenoid |
| b-Himachalene epoxide | terpene/terpenoid |
| b-Himachalol | terpene/terpenoid |
| b-Ionol | terpene/terpenoid |
| b-Ionone | terpene/terpenoid |
| b-Ionone epoxide | terpene/terpenoid |
| b-Irone | terpene/terpenoid |
| b-Isocomene | terpene/terpenoid |
| b-Isolongibornene | terpene/terpenoid |
| b-Longipinene | terpene/terpenoid |
| b-Maaliene | terpene/terpenoid |
| b-Microbiotene | terpene/terpenoid |
| b-n-Octyl-g-butanolide | terpene/terpenoid |

TABLE 2-continued

| | |
|---|---|
| b-Neoclovene | terpene/terpenoid |
| b-Oplopenone | terpene/terpenoid |
| b-Panasinsen-5a-ol | terpene/terpenoid |
| b-Panasinsene | terpene/terpenoid |
| b-Patchoulene | terpene/terpenoid |
| b-Phellandrene | terpene/terpenoid |
| b-Phenylethanol | terpene/terpenoid |
| b-Pinene | terpene/terpenoid |
| b-Pinene epoxide | terpene/terpenoid |
| b-Pinene epoxide (Isomer) | terpene/terpenoid |
| b-Pinguisene | terpene/terpenoid |
| b-Santalene | terpene/terpenoid |
| b-Santalol acetate | terpene/terpenoid |
| b-Selinene | terpene/terpenoid |
| b-Sesquifenchene | terpene/terpenoid |
| b-Sesquiphellandrene | terpene/terpenoid |
| b-Sesquiphellandrone | terpene/terpenoid |
| b-Sinensal | terpene/terpenoid |
| b-Spathulene | terpene/terpenoid |
| b-Terpineol | terpene/terpenoid |
| b-Thujaplicine | terpene/terpenoid |
| b-Thujone | terpene/terpenoid |
| b-Vetispirene | terpene/terpenoid |
| b-Vetivenene | terpene/terpenoid |
| b-Ylangene | terpene/terpenoid |
| Benzaldehyde | terpene/terpenoid |
| Benzoic acid | terpene/terpenoid |
| Benzyl 2-methylbutyrate | terpene/terpenoid |
| Benzyl 3-methylbutyrate | terpene/terpenoid |
| Benzyl acetate | terpene/terpenoid |
| Benzyl alcohol | terpene/terpenoid |
| Benzyl benzoate | terpene/terpenoid |
| Benzyl butanoate | terpene/terpenoid |
| Benzyl formate | terpene/terpenoid |
| Benzyl propionate | terpene/terpenoid |
| Benzyl salicylate | terpene/terpenoid |
| Benzyl acetone | terpene/terpenoid |
| Bergaptene | terpene/terpenoid |
| Betaer-13-ene | terpene/terpenoid |
| Beyerene | terpene/terpenoid |
| Bicyclo-4(15)-oppositene | terpene/terpenoid |
| Bicycloax-3-ene | terpene/terpenoid |
| Bicycloax-4(15)-ene | terpene/terpenoid |
| Bicycloelemene | terpene/terpenoid |
| Bicyclogermacren-14-al | terpene/terpenoid |
| Bicyclogermacrene | terpene/terpenoid |
| Bicyclohumulenone | terpene/terpenoid |
| Bicycloopposit-4-ene | terpene/terpenoid |
| Bicyclosesquiphellandrene | terpene/terpenoid |
| Bisabol-1-one | terpene/terpenoid |
| Bisabola-1,3,5,11-tetraene | terpene/terpenoid |
| Bisabola-1,3,5,7-tetraene | terpene/terpenoid |
| Bisabola-1,3,5,7(14)-tetraene | terpene/terpenoid |
| Bisabola-1,3(15),10-trien-9-ol (Isomer 1) | terpene/terpenoid |
| Bisabola-1,3(15),10-trien-9-ol (Isomer 2) | terpene/terpenoid |
| Bisabola-1(6),2,10Z-trien-12-al | terpene/terpenoid |
| Bisabola-2,10-diene 1,9-oxide | terpene/terpenoid |
| Bisabola-2,7(Z),10(Z)-triene-13-ol | terpene/terpenoid |
| Bisabolol oxide A | terpene/terpenoid |
| Bisabolol oxide B | terpene/terpenoid |
| Bisabolone oxide A | terpene/terpenoid |
| Bisacumol (Isomer 1) | terpene/terpenoid |
| Bisacumol (Isomer 2) | terpene/terpenoid |
| Borneol | terpene/terpenoid |
| Bornyl acetate | terpene/terpenoid |
| Bourbon-11-ene | terpene/terpenoid |
| Bourbon-7-ene | terpene/terpenoid |
| Bourbon-7(11)-ene | terpene/terpenoid |
| Brachyl oxide | terpene/terpenoid |
| Brachylaenalone A | terpene/terpenoid |
| Brachylaenalone B | terpene/terpenoid |
| Brasila-1,10-diene | terpene/terpenoid |
| Brasila-1(6),5(10)-diene | terpene/terpenoid |
| Brasila-5,10-diene | terpene/terpenoid |
| Brasila-5(10),6-diene | terpene/terpenoid |
| Bryopterine A | terpene/terpenoid |
| Bulnesol | terpene/terpenoid |
| Butyl angelate | terpene/terpenoid |
| Butyl benzoate | terpene/terpenoid |
| Butylphthalide | terpene/terpenoid |

TABLE 2-continued

| | |
|---|---|
| Cabreuva oxide A | terpene/terpenoid |
| Cabreuva oxide B | terpene/terpenoid |
| Cabreuva oxide C | terpene/terpenoid |
| Cabreuva oxide D | terpene/terpenoid |
| Cadalene | terpene/terpenoid |
| Cadin-1(10)-ene 5,11-oxide | terpene/terpenoid |
| Cadina-1,4-diene | terpene/terpenoid |
| Cadina-1(10),11-diene | terpene/terpenoid |
| Cadina-1(10),3,7(11)-triene | terpene/terpenoid |
| Cadina-1(10),4-dien-8a-ol | terpene/terpenoid |
| Cadina-1(10),4-dien-8a-ol | terpene/terpenoid |
| Cadina-1(10),7(11)-diene | terpene/terpenoid |
| Cadina-3,5-diene | terpene/terpenoid |
| Cadina-4,10(14)-dien-1a-ol | terpene/terpenoid |
| Cadina-4,11-dien-15-al | terpene/terpenoid |
| Cadina-4,11-dien-15-ol | terpene/terpenoid |
| Cadina-4,11-diene | terpene/terpenoid |
| Calarene | terpene/terpenoid |
| Camphene | terpene/terpenoid |
| Camphene hydrate | terpene/terpenoid |
| Camphor | terpene/terpenoid |
| Caparapidiol | terpene/terpenoid |
| Caparratriene | terpene/terpenoid |
| Capnell-9(12)-ene | terpene/terpenoid |
| Cara-2,4-diene | terpene/terpenoid |
| Carota-5,8-diene | terpene/terpenoid |
| Carotol | terpene/terpenoid |
| Carquejyl acetate | terpene/terpenoid |
| Carvacrol | terpene/terpenoid |
| Carvacrol methyl ether | terpene/terpenoid |
| Carvone | terpene/terpenoid |
| Carvone hydrate | terpene/terpenoid |
| Carvone hydrate acetate | terpene/terpenoid |
| Carvotanacetone | terpene/terpenoid |
| Caryolan-1-ol | terpene/terpenoid |
| Caryophylla-3(15),7(14)-dien-6-ol | terpene/terpenoid |
| Caryophyllan-2,6-a-oxide | terpene/terpenoid |
| Caryophyllen-2,6-b-oxide | terpene/terpenoid |
| Caryophyllene oxide | terpene/terpenoid |
| Cascarilladiene | terpene/terpenoid |
| Cedrenone | terpene/terpenoid |
| Cedrol | terpene/terpenoid |
| Cedryl acetate | terpene/terpenoid |
| Cembrene | terpene/terpenoid |
| Cembrene A | terpene/terpenoid |
| Cembrene C | terpene/terpenoid |
| Cembrenol | terpene/terpenoid |
| Chalcograne (Isomer 1) | terpene/terpenoid |
| Chalcograne (Isomer 2) | terpene/terpenoid |
| Chamazulene | terpene/terpenoid |
| Chavibetol (m-Eugenol) | terpene/terpenoid |
| Chavibetyl acetate | terpene/terpenoid |
| Chavicol | terpene/terpenoid |
| Chavicol acetate | terpene/terpenoid |
| Chenopodene | terpene/terpenoid |
| Chiloscyphone | terpene/terpenoid |
| Chloranthalactone A | terpene/terpenoid |
| Chloroatranol | terpene/terpenoid |
| Chrysanthenone | terpene/terpenoid |
| Chrysanthenone epoxide | terpene/terpenoid |
| cis- or trans-Linalool oxide (pyranoid) | terpene/terpenoid |
| cis- or trans-Linalool oxide (pyranoid) | terpene/terpenoid |
| cis-10-Hydroxycalamenene | terpene/terpenoid |
| cis-2-Hydroxycalamenene | terpene/terpenoid |
| cis-5-Hydroxycalamenene | terpene/terpenoid |
| cis-8-Acetylthio-p-menthan-3-one | terpene/terpenoid |
| cis-8-Mercapto-p-menthan-3-one | terpene/terpenoid |
| cis-a-Bergamotene | terpene/terpenoid |
| cis-a-Irone | terpene/terpenoid |
| cis-Anethol | terpene/terpenoid |
| cis-b-Elemene | terpene/terpenoid |
| cis-b-Guaiene | terpene/terpenoid |
| cis-b-Terpineol | terpene/terpenoid |
| cis-Cadina-4,6-dien-11-ol | terpene/terpenoid |
| cis-Calamenene | terpene/terpenoid |
| cis-Carveol | terpene/terpenoid |
| cis-Carvyl acetate | terpene/terpenoid |
| cis-Carvyl propionate | terpene/terpenoid |
| cis-Chrysanthemol | terpene/terpenoid |
| cis-Chrysanthenol | terpene/terpenoid |
| cis-Chrysanthenyl acetate | terpene/terpenoid |
| cis-Davanone | terpene/terpenoid |
| cis-Dihydrocarvone | terpene/terpenoid |
| cis-Dihydrocarvone epoxide | terpene/terpenoid |
| cis-Dihydromultifidene | terpene/terpenoid |
| cis-Dihydroroseoxide | terpene/terpenoid |
| cis-Dracunculifoliol | terpene/terpenoid |
| cis-Dracunculifolione | terpene/terpenoid |
| cis-Epoxypseudoisoeugenyl-2-methyl butyrate | terpene/terpenoid |
| cis-Ethyl chrysanthemate | terpene/terpenoid |
| cis-Eudesma-4,11-dien-8-ol | terpene/terpenoid |
| cis-Eudesma-4(15),11-dien-5-ol | terpene/terpenoid |
| cis-Eudesma-6,11-diene | terpene/terpenoid |
| cis-g-Irone | terpene/terpenoid |
| cis-Hormosirene | terpene/terpenoid |
| cis-Isopulegone | terpene/terpenoid |
| cis-Limonene oxide | terpene/terpenoid |
| cis-Linalool oxide (furanoid) | terpene/terpenoid |
| cis-Methyl dihydrojasmonate | terpene/terpenoid |
| cis-Muurola-3,5-diene | terpene/terpenoid |
| cis-Muurola-4(15),5-diene | terpene/terpenoid |
| cis-Myrtanol | terpene/terpenoid |
| cis-p-Menth-2-en-1-ol | terpene/terpenoid |
| cis-p-Mentha-1(7),8-dien-2-ol | terpene/terpenoid |
| cis-p-Mentha-2,8-dien-1-ol | terpene/terpenoid |
| cis-Pinane | terpene/terpenoid |
| cis-Pinocarvyl acetate | terpene/terpenoid |
| cis-Piperitol | terpene/terpenoid |
| cis-Pulegol | terpene/terpenoid |
| cis-Rose oxide | terpene/terpenoid |
| cis-Sabinene hydrat acetate | terpene/terpenoid |
| cis-Sabinene hydrate | terpene/terpenoid |
| cis-Sesquisabinenhydrate | terpene/terpenoid |
| cis-Spiroether | terpene/terpenoid |
| cis-Thiorose oxide | terpene/terpenoid |
| cis-Thujol | terpene/terpenoid |
| cis-Totarol | terpene/terpenoid |
| cis-Verbenol | terpene/terpenoid |
| cis-Verbenyl acetate | terpene/terpenoid |
| Citronellal | terpene/terpenoid |
| Citronellol | terpene/terpenoid |
| Citronellyl acetate | terpene/terpenoid |
| Citronellyl butyrate | terpene/terpenoid |
| Citronellyl formate | terpene/terpenoid |
| Citronellyl propionate | terpene/terpenoid |
| Clovene | terpene/terpenoid |
| Clovenol | terpene/terpenoid |
| Conocephalenol | terpene/terpenoid |
| Copaborneol | terpene/terpenoid |
| Copaen-15-ol | terpene/terpenoid |
| Copalol | terpene/terpenoid |
| Coronarin E | terpene/terpenoid |
| Costunolide | terpene/terpenoid |
| Coumarin | terpene/terpenoid |
| Crispatanolide | terpene/terpenoid |
| Crocetane | terpene/terpenoid |
| Cryptone | terpene/terpenoid |
| Cubeb-11-ene | terpene/terpenoid |
| Cubeban-11-ol | terpene/terpenoid |
| Cubebol | terpene/terpenoid |
| Cubenol | terpene/terpenoid |
| Cuparene | terpene/terpenoid |
| Cuparophenol | terpene/terpenoid |
| Curcerenone | terpene/terpenoid |
| Curcuphenol | terpene/terpenoid |
| Cyclo-b-ionone | terpene/terpenoid |
| Cyclobazzanene | terpene/terpenoid |
| Cyclocolorenone | terpene/terpenoid |
| Cyclofarnesa-5(14),8,10-triene | terpene/terpenoid |
| Cyclomyltaylan-15-ol | terpene/terpenoid |
| Cyclomyltaylane | terpene/terpenoid |
| Cyclooctatetraene | terpene/terpenoid |
| Cyclosativene | terpene/terpenoid |
| Cycloseychellene | terpene/terpenoid |
| Cymen-8-ol | terpene/terpenoid |
| Cymen-9-ol | terpene/terpenoid |
| Cyperadiene | terpene/terpenoid |
| Cyperadione | terpene/terpenoid |
| Cyperenal | terpene/terpenoid |
| Cyperene | terpene/terpenoid |

TABLE 2-continued

| | |
|---|---|
| Cyperene epoxide | terpene/terpenoid |
| Cyperol | terpene/terpenoid |
| Cyperotundone | terpene/terpenoid |
| Cyprotene | terpene/terpenoid |
| D 2-Carene | terpene/terpenoid |
| D 3-Carene | terpene/terpenoid |
| d-Amorphene | terpene/terpenoid |
| d-Cadinene | terpene/terpenoid |
| d-Cuprenene | terpene/terpenoid |
| d-Decanolide | terpene/terpenoid |
| d-Dodecanolide | terpene/terpenoid |
| d-Elemene | terpene/terpenoid |
| d-Heptanolide | terpene/terpenoid |
| d-Hexaolide | terpene/terpenoid |
| d-Jasmolactone | terpene/terpenoid |
| d-Nonanolide | terpene/terpenoid |
| d-Octanolide | terpene/terpenoid |
| d-Patchoulene | terpene/terpenoid |
| d-Selinene | terpene/terpenoid |
| d-Terpineol | terpene/terpenoid |
| d-Tetradecalactone | terpene/terpenoid |
| d-Tridecanolide | terpene/terpenoid |
| d-Undecanolide | terpene/terpenoid |
| D7,8-ar-Himachalene | terpene/terpenoid |
| D7(14)-ar-Himachalene | terpene/terpenoid |
| Dactylol | terpene/terpenoid |
| Dauca-3,8-diene | terpene/terpenoid |
| Dauca-8,11-diene | terpene/terpenoid |
| Daucalene | terpene/terpenoid |
| Daucene | terpene/terpenoid |
| Davana ether | terpene/terpenoid |
| Davana ether (Isomer) | terpene/terpenoid |
| Davanafuran | terpene/terpenoid |
| Dec-9-en-1-ol | terpene/terpenoid |
| Deca-2,4-dienal | terpene/terpenoid |
| Decanoic acid | terpene/terpenoid |
| Dehydrocostunolide | terpene/terpenoid |
| Dehydroelsholtzia ketone | terpene/terpenoid |
| Dehydrogeosmin | terpene/terpenoid |
| Dehydrolinalool | terpene/terpenoid |
| Dehydropinguisenol | terpene/terpenoid |
| Dehydrosabinaketone | terpene/terpenoid |
| Dehydrosesquicineol | terpene/terpenoid |
| Dehydrosesquicineyl-12-ol | terpene/terpenoid |
| Deodarone | terpene/terpenoid |
| Deoxopinguisone | terpene/terpenoid |
| Desmarestene | terpene/terpenoid |
| Desmethoxyencecalin | terpene/terpenoid |
| Di-(2-hydroxypropyl)-ether | terpene/terpenoid |
| Di-n-propyl disulfide | terpene/terpenoid |
| Di-n-propyl tetrasulfide | terpene/terpenoid |
| Di-n-propyl trisulfide | terpene/terpenoid |
| Dictyopterene A | terpene/terpenoid |
| Dictyotene | terpene/terpenoid |
| Diethylphthalate | terpene/terpenoid |
| Dihydro-ar-turmerone | terpene/terpenoid |
| Dihydroactinidiolide | terpene/terpenoid |
| Dihydroagarofuran | terpene/terpenoid |
| Dihydrobryopterine A | terpene/terpenoid |
| Dihydrocarveol (Isomer 1) | terpene/terpenoid |
| Dihydrocarveol (Isomer 2) | terpene/terpenoid |
| Dihydrocarveol (Isomer 3) | terpene/terpenoid |
| Dihydrocarveol acetate (Isomer 2) | terpene/terpenoid |
| Dihydrocarveol acetate (Isomer 2) | terpene/terpenoid |
| Dihydrocarveol acetate (Isomer 2) | terpene/terpenoid |
| Dihydrochiloscypholone | terpene/terpenoid |
| Dihydrocolumellarine | terpene/terpenoid |
| Dihydrodehydrocostus lactone | terpene/terpenoid |
| Dihydrodiplophylline | terpene/terpenoid |
| Dihydroedulan | terpene/terpenoid |
| Dihydrofrullanolide | terpene/terpenoid |
| Dihydroisoalantolactone | terpene/terpenoid |
| Dihydrojasmone | terpene/terpenoid |
| Dihydrolinalool | terpene/terpenoid |
| Dihydromayurone | terpene/terpenoid |
| Dihydromyrcenol | terpene/terpenoid |
| Dihydronaginata ketone | terpene/terpenoid |
| Dihydrosesquicineol | terpene/terpenoid |
| Dihydrotagetone | terpene/terpenoid |
| Dillether | terpene/terpenoid |

TABLE 2-continued

| | |
|---|---|
| Dimethyl trisulfide | terpene/terpenoid |
| Dimethyl-tetrasulfide | terpene/terpenoid |
| Diosphenol | terpene/terpenoid |
| Diplophylline | terpene/terpenoid |
| Docosanal | terpene/terpenoid |
| Dodecanal | terpene/terpenoid |
| Dodecanol | terpene/terpenoid |
| Dodecyl acetate | terpene/terpenoid |
| Dolabella-6,10,15-triene | terpene/terpenoid |
| Dolabradiene | terpene/terpenoid |
| Dotriacontane | terpene/terpenoid |
| Drim-8-en-7-one | terpene/terpenoid |
| Drim-8-ene | terpene/terpenoid |
| Drim-8(12)-ene | terpene/terpenoid |
| Drimenene | terpene/terpenoid |
| Drimenol | terpene/terpenoid |
| e-Amorphene | terpene/terpenoid |
| e-Cadinene | terpene/terpenoid |
| e-Cuprenene | terpene/terpenoid |
| e-Muurolene | terpene/terpenoid |
| e-Patchoulene | terpene/terpenoid |
| Ectocarpene | terpene/terpenoid |
| Eicosanal | terpene/terpenoid |
| Elema-1,3-dien-7-ol | terpene/terpenoid |
| Elema-1,3,7-triene | terpene/terpenoid |
| Elema-1,3,7(11),8-tetraene | terpene/terpenoid |
| Elemenone | terpene/terpenoid |
| Elemicine | terpene/terpenoid |
| Elemol | terpene/terpenoid |
| Elsholtzia ketone | terpene/terpenoid |
| Encecalin | terpene/terpenoid |
| endo-Brevicomin | terpene/terpenoid |
| endo-Isocamphanyl acetate | terpene/terpenoid |
| ent-Diplophyllolide | terpene/terpenoid |
| epi-b-Santalene | terpene/terpenoid |
| epi-Cyclosantalal | terpene/terpenoid |
| epi-Methyljasmonate | terpene/terpenoid |
| epi-Zonarene | terpene/terpenoid |
| Epicurcerenone | terpene/terpenoid |
| Eremoligenol | terpene/terpenoid |
| Eremophila-1(10),11-dien-9b-ol | terpene/terpenoid |
| Eremophila-1(10),6-diene | terpene/terpenoid |
| Eremophila-1(10),7-diene | terpene/terpenoid |
| Eremophila-1(10),7(11)-diene | terpene/terpenoid |
| Eremophila-1(10),8,11-triene | terpene/terpenoid |
| Eremophilene | terpene/terpenoid |
| Erythrodiene | terpene/terpenoid |
| Estragol (Methylchavicol) | terpene/terpenoid |
| Ethyl 2-methylbutyrate | terpene/terpenoid |
| Ethyl 2-phenylhexanoate | terpene/terpenoid |
| Ethyl benzoate | terpene/terpenoid |
| Ethyl decanoate | terpene/terpenoid |
| Ethyl geranate | terpene/terpenoid |
| Ethyl hexadecanoate | terpene/terpenoid |
| Ethyl nerolat | terpene/terpenoid |
| Ethyl p-methoxybenzoate | terpene/terpenoid |
| Ethyl palmitate | terpene/terpenoid |
| Ethyl salicylate | terpene/terpenoid |
| Ethylbenzene | terpene/terpenoid |
| Eudesm-11-en-4a-ol | terpene/terpenoid |
| Eudesm-3-en-6-ol | terpene/terpenoid |
| Eudesm-3-en-7-ol | terpene/terpenoid |
| Eudesm-3-ene 6,7-oxide | terpene/terpenoid |
| Eudesm-3,11-dien-5-ol | terpene/terpenoid |
| Eudesm-4-en-6-one | terpene/terpenoid |
| Eudesm-4-en-7-ol | terpene/terpenoid |
| Eudesm-4(15)-en-6-ol | terpene/terpenoid |
| Eudesm-4(15)-en-7-ol | terpene/terpenoid |
| Eudesm-4(15)en-6-one | terpene/terpenoid |
| Eudesm-7(11)-en-4a-ol | terpene/terpenoid |
| Eudesma-1,4(15),11-triene | terpene/terpenoid |
| Eudesma-2,4,11-triene | terpene/terpenoid |
| Eudesma-2,4(15),11-triene | terpene/terpenoid |
| Eudesma-3,11-dien-2-one | terpene/terpenoid |
| Eudesma-3,11-dien-8-one | terpene/terpenoid |
| Eudesma-3,5,11-triene | terpene/terpenoid |
| Eudesma-3,7(11)-dien-8-one | terpene/terpenoid |
| Eudesma-4,11-dien-9-one | terpene/terpenoid |
| Eudesma-4(15),11-dien-5-ol | terpene/terpenoid |
| Eudesma-4(15),11-dien-8-one | terpene/terpenoid |

TABLE 2-continued

| | |
|---|---|
| Eudesma-4(15),7-dien-1b-ol | terpene/terpenoid |
| Eudesma-4(15),7(11)-dien-8-one | terpene/terpenoid |
| Eudesma-4(15),7(11),9-trien-12-olide | terpene/terpenoid |
| Eudesma-5,7(11)-diene | terpene/terpenoid |
| Eugenitine | terpene/terpenoid |
| Eugenol | terpene/terpenoid |
| Eupatoriochromene | terpene/terpenoid |
| exo-Isocamphanyl acetate | terpene/terpenoid |
| Falcarinol | terpene/terpenoid |
| Falcarinone | terpene/terpenoid |
| Farnesal (Isomer 1) | terpene/terpenoid |
| Farnesal (Isomer 2) | terpene/terpenoid |
| Farnesal (Isomer 3) | terpene/terpenoid |
| Farnesane | terpene/terpenoid |
| Farnesol (Isomer 1) | terpene/terpenoid |
| Farnesol (Isomer 2) | terpene/terpenoid |
| Fenchone | terpene/terpenoid |
| Fenchyl acetate | terpene/terpenoid |
| Fenchyl acetate (Isomer) | terpene/terpenoid |
| Ferulyl angelate | terpene/terpenoid |
| Flavesone | terpene/terpenoid |
| Fokienol | terpene/terpenoid |
| Folifolone | terpene/terpenoid |
| Fragranol | terpene/terpenoid |
| Fragranyl acetate | terpene/terpenoid |
| Frontaline | terpene/terpenoid |
| Frullanolide | terpene/terpenoid |
| Fukinanolide | terpene/terpenoid |
| Furanoelemene | terpene/terpenoid |
| Furanoeremophilene | terpene/terpenoid |
| Furanoeremophilone | terpene/terpenoid |
| Furanoeudesm-1,3-diene | terpene/terpenoid |
| Furanogermacrene | terpene/terpenoid |
| Furanogermenone | terpene/terpenoid |
| Furomyrcenol | terpene/terpenoid |
| Furopelargone A | terpene/terpenoid |
| Fusicocca-2,5-diene | terpene/terpenoid |
| Fusicocca-3,5-diene | terpene/terpenoid |
| g-Amorphene | terpene/terpenoid |
| g-Bicyclofarnesal | terpene/terpenoid |
| g-Bicyclohomofarnesal | terpene/terpenoid |
| g-Cadinene | terpene/terpenoid |
| g-Calacorene | terpene/terpenoid |
| g-Costol | terpene/terpenoid |
| g-Cuprenene | terpene/terpenoid |
| g-Curcumen-15-al | terpene/terpenoid |
| g-Curcumene | terpene/terpenoid |
| g-Decanolide | terpene/terpenoid |
| g-Dodecanolide | terpene/terpenoid |
| g-Elemene | terpene/terpenoid |
| g-Eudesmol | terpene/terpenoid |
| g-Guaiene | terpene/terpenoid |
| g-Gurjunene | terpene/terpenoid |
| g-Heptanolide | terpene/terpenoid |
| g-Hexanolide | terpene/terpenoid |
| g-Himachalene | terpene/terpenoid |
| g-Humulene | terpene/terpenoid |
| g-Maaliene | terpene/terpenoid |
| g-Muurolene | terpene/terpenoid |
| g-n-Tetradecyl-g-butanolide | terpene/terpenoid |
| g-Nonanolide | terpene/terpenoid |
| g-Octanolide | terpene/terpenoid |
| g-Palmitolactone | terpene/terpenoid |
| g-Patchoulene | terpene/terpenoid |
| g-Terpinene | terpene/terpenoid |
| g-Terpineol | terpene/terpenoid |
| g-Tetradecanolide | terpene/terpenoid |
| g-Undecanolide | terpene/terpenoid |
| g-Vetivenene | terpene/terpenoid |
| Galaxolide | terpene/terpenoid |
| Geijerene | terpene/terpenoid |
| Geosmin | terpene/terpenoid |
| Geranial | terpene/terpenoid |
| Geraniol | terpene/terpenoid |
| Geranyl 2-methylbutyrate | terpene/terpenoid |
| Geranyl acetate | terpene/terpenoid |
| Geranyl butyrate | terpene/terpenoid |
| Geranyl crotonate | terpene/terpenoid |
| Geranyl formate | terpene/terpenoid |
| Geranyl propionate | terpene/terpenoid |

TABLE 2-continued

| | |
|---|---|
| Geranyl tiglate | terpene/terpenoid |
| Geranylacetone | terpene/terpenoid |
| Geranyllinalool | terpene/terpenoid |
| Germacra-4(15),5,10(14)-trien-1a-ol | terpene/terpenoid |
| Germacrene A | terpene/terpenoid |
| Germacrene B | terpene/terpenoid |
| Germacrene D | terpene/terpenoid |
| Germacrone | terpene/terpenoid |
| Ginsenol | terpene/terpenoid |
| Ginsensene | terpene/terpenoid |
| Globulol | terpene/terpenoid |
| Gorgon-11-en-4-ol | terpene/terpenoid |
| Gorgona-1,4(15),11-triene | terpene/terpenoid |
| Grandisol | terpene/terpenoid |
| Grimaldone | terpene/terpenoid |
| Guaia-1(10),11-diene | terpene/terpenoid |
| Guaia-3,10(14)-dien-6,12-olide | terpene/terpenoid |
| Guaia-3,10(14)-diene 5,11-oxide | terpene/terpenoid |
| Guaia-3,7(11),10(14)-trien-6,12-olide | terpene/terpenoid |
| Guaia-3,9-diene 5,11-oxide | terpene/terpenoid |
| Guaia-6,10(14)-diene-4b-ol | terpene/terpenoid |
| Guaia-6,9-dien-4b-ol | terpene/terpenoid |
| Guaia-6,9-diene | terpene/terpenoid |
| Guaia-9,11-diene | terpene/terpenoid |
| Guaiazulene | terpene/terpenoid |
| Guaioxide | terpene/terpenoid |
| Gymnomitr-3-en-15-ol | terpene/terpenoid |
| Gymnomitr-3(15)-en-12-al | terpene/terpenoid |
| Gymnomitr-3(15)-en-12-oic acid | terpene/terpenoid |
| Gymnomitr-3(15)-en-4-one | terpene/terpenoid |
| Gymnomitr-3(15)-en-4a-ol | terpene/terpenoid |
| Gymnomitr-3(15)-en-4b-ol | terpene/terpenoid |
| Gymnomitr-3(15)-en-5b-ol | terpene/terpenoid |
| Gymnomitra-3(15),4-diene | terpene/terpenoid |
| Gymnomitran-4-one | terpene/terpenoid |
| Gymnomitrol | terpene/terpenoid |
| Gymnomitrol acetate | terpene/terpenoid |
| Gymnomitrone | terpene/terpenoid |
| Helifolen-12-al (syn-syn-syn) | terpene/terpenoid |
| Helifolene | terpene/terpenoid |
| Helminthogermacrene | terpene/terpenoid |
| Heptacosane | terpene/terpenoid |
| Herbertene | terpene/terpenoid |
| Hex-5-en-1-ol | terpene/terpenoid |
| Hex-5-en-3-ol | terpene/terpenoid |
| Hexadecanal | terpene/terpenoid |
| Hexadecyl acetate | terpene/terpenoid |
| Hexyl acetate | terpene/terpenoid |
| Hexyl hexanoate | terpene/terpenoid |
| Heyderiol | terpene/terpenoid |
| Hinesene | terpene/terpenoid |
| Hinesol | terpene/terpenoid |
| Hirsutene | terpene/terpenoid |
| Homovanilline alcohol | terpene/terpenoid |
| Hotrienol | terpene/terpenoid |
| Humulene epoxide 1 | terpene/terpenoid |
| Humulene epoxide 2 | terpene/terpenoid |
| Humulene epoxide 3 | terpene/terpenoid |
| Hydrocinnamyl acetate | terpene/terpenoid |
| Hydroxycitronellal | terpene/terpenoid |
| Incensol acetate | terpene/terpenoid |
| Incensole | terpene/terpenoid |
| Indole | terpene/terpenoid |
| Ipsdienol | terpene/terpenoid |
| Ipsenol | terpene/terpenoid |
| Ishwarane | terpene/terpenoid |
| Iso-a-humulene | terpene/terpenoid |
| Iso-b-elemene | terpene/terpenoid |
| Iso-g-bisabolene | terpene/terpenoid |
| Isoabienol | terpene/terpenoid |
| Isoacorone | terpene/terpenoid |
| Isoafricanol | terpene/terpenoid |
| Isoalantolactone | terpene/terpenoid |
| Isoascaridol | terpene/terpenoid |
| Isobarbatene | terpene/terpenoid |
| Isobazzanene | terpene/terpenoid |
| Isobicyclogermacrene | terpene/terpenoid |
| Isoborneol | terpene/terpenoid |
| Isobornyl acetate | terpene/terpenoid |
| Isobornyl butyrate | terpene/terpenoid |

TABLE 2-continued

| | |
|---|---|
| Isobornyl formate | terpene/terpenoid |
| Isobornyl isobutyrate | terpene/terpenoid |
| Isobornyl isovalerate | terpene/terpenoid |
| Isobornyl propionate | terpene/terpenoid |
| Isobutyl angelate | terpene/terpenoid |
| Isocalamenene | terpene/terpenoid |
| Isocaryophyllen-14-al (b-Betulenal) | terpene/terpenoid |
| Isocaryophyllene | terpene/terpenoid |
| Isocembrene | terpene/terpenoid |
| Isochrysanthenone | terpene/terpenoid |
| Isocyclobazzanene | terpene/terpenoid |
| Isocyperol | terpene/terpenoid |
| Isodauca-4,6-diene | terpene/terpenoid |
| Isodauca-4,7(14)-diene | terpene/terpenoid |
| Isodauca-6,9-diene | terpene/terpenoid |
| Isodavanone | terpene/terpenoid |
| Isoeugenitine | terpene/terpenoid |
| Isogeranial | terpene/terpenoid |
| Isogermacrene A | terpene/terpenoid |
| Isogermacrene D | terpene/terpenoid |
| Isogermafurenolide | terpene/terpenoid |
| Isogymnomitrol | terpene/terpenoid |
| Isohibaene | terpene/terpenoid |
| Isohumbertiol B | terpene/terpenoid |
| Isohumbertiol D (Isomer 1) | terpene/terpenoid |
| Isohumbertiol D (Isomer 2) | terpene/terpenoid |
| Isoitalicene epoxide | terpene/terpenoid |
| Isoledene | terpene/terpenoid |
| Isolepidozene | terpene/terpenoid |
| Isolongifolene | terpene/terpenoid |
| Isolongifolol | terpene/terpenoid |
| Isomenthol | terpene/terpenoid |
| Isomenthone | terpene/terpenoid |
| Isomenthyl acetate | terpene/terpenoid |
| Isonaviculol | terpene/terpenoid |
| Isoneral | terpene/terpenoid |
| Isopatchoula-3,5-diene | terpene/terpenoid |
| Isoperillene | terpene/terpenoid |
| Isophorone | terpene/terpenoid |
| Isophyllocladene | terpene/terpenoid |
| Isophytol | terpene/terpenoid |
| Isopimara-7,15-diene | terpene/terpenoid |
| Isopimara-8,15-diene | terpene/terpenoid |
| Isopimara-8,15-diene | terpene/terpenoid |
| Isopimara-8(14),15-diene | terpene/terpenoid |
| Isopinguisanine | terpene/terpenoid |
| Isopinocampheol | terpene/terpenoid |
| Isopinocamphone | terpene/terpenoid |
| Isopiperitenone | terpene/terpenoid |
| Isopulegol | terpene/terpenoid |
| Isopulegol acetate (Isomer 1) | terpene/terpenoid |
| Isopulegol acetate (Isomer 2) | terpene/terpenoid |
| Isorotundene | terpene/terpenoid |
| Isorotundenol | terpene/terpenoid |
| Isosaccogynol | terpene/terpenoid |
| Isosaccogynone | terpene/terpenoid |
| Isosativene | terpene/terpenoid |
| Isospathulenol | terpene/terpenoid |
| Isotheaspirane (Isomer 1) | terpene/terpenoid |
| Isotheaspirane (Isomer 1) | terpene/terpenoid |
| Isothujol | terpene/terpenoid |
| Isovalencenol | terpene/terpenoid |
| Isozierene | terpene/terpenoid |
| Italicen-13-al | terpene/terpenoid |
| Italicen-13-ol | terpene/terpenoid |
| Italicen-4-one | terpene/terpenoid |
| Italicene | terpene/terpenoid |
| Italicene epoxide | terpene/terpenoid |
| Italicene ether | terpene/terpenoid |
| Jaeschkeanadiol | terpene/terpenoid |
| Junenol | terpene/terpenoid |
| Karahanaenone | terpene/terpenoid |
| Kessane | terpene/terpenoid |
| Khusien-12-al | terpene/terpenoid |
| Khusienol acetate | terpene/terpenoid |
| Khusimol | terpene/terpenoid |
| Khusiol | terpene/terpenoid |
| Khusol | terpene/terpenoid |
| Labda-7,13,14-triene | terpene/terpenoid |
| Labda-7,14-dien-13-ol | terpene/terpenoid |

TABLE 2-continued

| | |
|---|---|
| Labda-8(17),14-dien-6,13-diol | terpene/terpenoid |
| Laciniata furanone H | terpene/terpenoid |
| Lactarazulene | terpene/terpenoid |
| Lactarovioline | terpene/terpenoid |
| Lanceol oxide | terpene/terpenoid |
| Lanciniata furanone F | terpene/terpenoid |
| Laurene | terpene/terpenoid |
| Laurenene | terpene/terpenoid |
| Lavandulol | terpene/terpenoid |
| Lavandulyl acetate | terpene/terpenoid |
| Lavender lactone | terpene/terpenoid |
| Ledene | terpene/terpenoid |
| Ledol | terpene/terpenoid |
| Lemnalol | terpene/terpenoid |
| Lemnalone | terpene/terpenoid |
| Lepidozenal | terpene/terpenoid |
| Leptospermone | terpene/terpenoid |
| Libocedrol | terpene/terpenoid |
| Lilac alcohol (2R,2'R,5'S) | terpene/terpenoid |
| Lilac alcohol (2R,2'S,5'S)) | terpene/terpenoid |
| Lilac alcohol (2S,2'S,5'S) | terpene/terpenoid |
| Lilac aldehyde (2R,2'R,5'S) | terpene/terpenoid |
| Lilac aldehyde (2R,2'S,5'S) | terpene/terpenoid |
| Lilac aldehyde (2S,2'S,5'S) | terpene/terpenoid |
| Limonen-10-ol | terpene/terpenoid |
| Limonene | terpene/terpenoid |
| Linalool | terpene/terpenoid |
| Linalyl acetate | terpene/terpenoid |
| Lineatine | terpene/terpenoid |
| Longiborneol | terpene/terpenoid |
| Longicamphenilol | terpene/terpenoid |
| Longicamphenilone | terpene/terpenoid |
| Longicyclene | terpene/terpenoid |
| Longifolene | terpene/terpenoid |
| Longifolol | terpene/terpenoid |
| Longipin-3-en-10-ol | terpene/terpenoid |
| Longipinanol | terpene/terpenoid |
| Longipinanol, high temp. | terpene/terpenoid |
| Lowry's phenol | terpene/terpenoid |
| Lyral | terpene/terpenoid |
| Lyral (Isomer) | terpene/terpenoid |
| m-Camphorene | terpene/terpenoid |
| m-Cresol | terpene/terpenoid |
| m-Cymene | terpene/terpenoid |
| Maali-1,3-diene | terpene/terpenoid |
| Maali-4(15)-en-1-ol | terpene/terpenoid |
| Maalian-5-ol | terpene/terpenoid |
| Maaliol | terpene/terpenoid |
| Maalioxide | terpene/terpenoid |
| Manool | terpene/terpenoid |
| Manool oxide | terpene/terpenoid |
| Marsupellone | terpene/terpenoid |
| Marsupellyl acetate | terpene/terpenoid |
| Massoialactone | terpene/terpenoid |
| Melanene | terpene/terpenoid |
| Menth-1-en-9-ol | terpene/terpenoid |
| Menth-2-en-1,4-diol | terpene/terpenoid |
| Menthofuran | terpene/terpenoid |
| Menthol | terpene/terpenoid |
| Menthone | terpene/terpenoid |
| Menthothiophene | terpene/terpenoid |
| Menthyl acetate | terpene/terpenoid |
| Menthyl formate | terpene/terpenoid |
| Methallyl angelate | terpene/terpenoid |
| Methyl 10-methyldodecanoate | terpene/terpenoid |
| Methyl 11-methyltridecanoate | terpene/terpenoid |
| Methyl 2-(2-methylbutyroxy)-3-methylpentanoate | terpene/terpenoid |
| Methyl 2-hydroxy-4-methoxy-6-methylbenzoate | terpene/terpenoid |
| Methyl 2-hydroxydodecanoate | terpene/terpenoid |
| Methyl 2-hydroxyhexanoate | terpene/terpenoid |
| Methyl 2-hydroxyisopentanoate | terpene/terpenoid |
| Methyl 2-hydroxypentanoate | terpene/terpenoid |
| Methyl 2-hydroxytetradecanoate | terpene/terpenoid |
| Methyl 2-methylbutyrate | terpene/terpenoid |
| Methyl 2-methyldodecanoate | terpene/terpenoid |
| Methyl 2-methylhexadecanoate | terpene/terpenoid |
| Methyl 2-methylpentadecanoate | terpene/terpenoid |
| Methyl 2-methyltetradecanoate | terpene/terpenoid |
| Methyl 2-methylundecanoate | terpene/terpenoid |
| Methyl 2-octynoate | terpene/terpenoid |

TABLE 2-continued

| | |
|---|---|
| Methyl 2,4-Dimethoxy-6-methylbenzoate | terpene/terpenoid |
| Methyl 3-(4-methoxyphenyl)-propionate | terpene/terpenoid |
| Methyl 3-ethyl-4-methylpentanoate | terpene/terpenoid |
| Methyl 3-methylfuroate | terpene/terpenoid |
| Methyl 3-methylorsellinate | terpene/terpenoid |
| Methyl 3-methylpentanoate | terpene/terpenoid |
| Methyl 3-methylpentanoate | terpene/terpenoid |
| Methyl 3-phenylpropanoate | terpene/terpenoid |
| Methyl 3,4,6-trimethoxy-2-methylbenzoate | terpene/terpenoid |
| Methyl 3,5-dimethoxyphenylacetate | terpene/terpenoid |
| Methyl 3,7-dimethyloctanoate | terpene/terpenoid |
| Methyl 4-Hydroxy-3-methoxy-5-(1,1-dimethylprop-2-enyl)-benzoate | terpene/terpenoid |
| Methyl 4-hydroxybenzoate | terpene/terpenoid |
| Methyl 4-hydroxymandelate | terpene/terpenoid |
| Methyl 4-methoxymandelate | terpene/terpenoid |
| Methyl 4-methoxyphenylacetate | terpene/terpenoid |
| Methyl 4-methylhexanoate | terpene/terpenoid |
| Methyl 6-Hydroxy-2-methyl-3,4-methylendioxybenzoate | terpene/terpenoid |
| Methyl 6-Methoxy-2-methyl-3,4-methylendioxybenzoate | terpene/terpenoid |
| Methyl a-cyclogeranate | terpene/terpenoid |
| Methyl anthranilate | terpene/terpenoid |
| Methyl arachidate | terpene/terpenoid |
| Methyl arachidonate | terpene/terpenoid |
| Methyl behenate | terpene/terpenoid |
| Methyl benzoate | terpene/terpenoid |
| Methyl citronellate | terpene/terpenoid |
| Methyl decanoate | terpene/terpenoid |
| Methyl dodecanoate | terpene/terpenoid |
| Methyl elaidate | terpene/terpenoid |
| Methyl erucate | terpene/terpenoid |
| Methyl geranate | terpene/terpenoid |
| Methyl heneicosanoate (C-21) | terpene/terpenoid |
| Methyl heptadecanoate | terpene/terpenoid |
| Methyl hexanoate | terpene/terpenoid |
| Methyl jasmonate | terpene/terpenoid |
| Methyl lignocerate | terpene/terpenoid |
| Methyl linoleate | terpene/terpenoid |
| Methyl linolenate | terpene/terpenoid |
| Methyl linolenate | terpene/terpenoid |
| Methyl madelate | terpene/terpenoid |
| Methyl myristate | terpene/terpenoid |
| Methyl myristoleate | terpene/terpenoid |
| Methyl n-propyl disulfide | terpene/terpenoid |
| Methyl n-propyl trisufide | terpene/terpenoid |
| Methyl nerolate | terpene/terpenoid |
| Methyl nervonate | terpene/terpenoid |
| Methyl nonanoate | terpene/terpenoid |
| Methyl norpinguisonate | terpene/terpenoid |
| Methyl o-methoxybenzoate | terpene/terpenoid |
| Methyl octanoate | terpene/terpenoid |
| Methyl oleate | terpene/terpenoid |
| Methyl p-methoxybenzoate | terpene/terpenoid |
| Methyl palmitate | terpene/terpenoid |
| Methyl palmitoleate | terpene/terpenoid |
| Methyl pentadecanoate | terpene/terpenoid |
| Methyl perillate | terpene/terpenoid |
| Methyl phenyl acetate | terpene/terpenoid |
| Methyl salicylate | terpene/terpenoid |
| Methyl stearate | terpene/terpenoid |
| Methyl trans-Dihydrojasmonate | terpene/terpenoid |
| Methyl tricosanoate | terpene/terpenoid |
| Methyl tridecanoate | terpene/terpenoid |
| Methyl undecanoate | terpene/terpenoid |
| Methyl eugenol | terpene/terpenoid |
| Microbiotol | terpene/terpenoid |
| Mintoxide | terpene/terpenoid |
| Mintsulphide | terpene/terpenoid |
| Modhephene | terpene/terpenoid |
| Moskachane B | terpene/terpenoid |
| Moskachane D | terpene/terpenoid |
| Muurol-4-en-3,8-dione | terpene/terpenoid |
| Muurol-4-en-6a-ol | terpene/terpenoid |
| Muurola-3,7(11)-dien-1-ol | terpene/terpenoid |
| Muurola-4,10(14)-dien-1-ol | terpene/terpenoid |
| Muurola-4,10(14)-dien-8a-ol | terpene/terpenoid |
| Muurola-4,10(14)-dien-8b-ol | terpene/terpenoid |
| Muurola-4,11-diene | terpene/terpenoid |

TABLE 2-continued

| | |
|---|---|
| Muurolan-4,7-oxide | terpene/terpenoid |
| Myli-4(15)-en-3-one | terpene/terpenoid |
| Myli-4(15)-ene | terpene/terpenoid |
| Mylian-3-one | terpene/terpenoid |
| Myliol | terpene/terpenoid |
| Myltayl-4-ene | terpene/terpenoid |
| Myltayl-4(12)-ene | terpene/terpenoid |
| Myltaylenol | terpene/terpenoid |
| Myrcene | terpene/terpenoid |
| Myristicine | terpene/terpenoid |
| Myrtenal | terpene/terpenoid |
| Myrtenol | terpene/terpenoid |
| Myrtenyl acetate | terpene/terpenoid |
| Myrtenyl methyl ether | terpene/terpenoid |
| N-2-[(4-Hydroxyphenyl)-ethyl]-tiglamide | terpene/terpenoid |
| N-Acetyl methyl anthranilate | terpene/terpenoid |
| n-Butyl butyrate | terpene/terpenoid |
| n-Decanal | terpene/terpenoid |
| n-Decane | terpene/terpenoid |
| n-Decyl acetate | terpene/terpenoid |
| n-Decyl butanoate | terpene/terpenoid |
| n-Docosane (C-22) | terpene/terpenoid |
| n-Dodecane | terpene/terpenoid |
| n-Dodecanoic acid | terpene/terpenoid |
| n-Eicosane (C-20) | terpene/terpenoid |
| n-Heneicosane (C-21) | terpene/terpenoid |
| n-Heptadecanal | terpene/terpenoid |
| n-Heptadecane | terpene/terpenoid |
| n-Heptanal | terpene/terpenoid |
| n-Heptyl butanoate | terpene/terpenoid |
| n-Hexacosane (C-26) | terpene/terpenoid |
| n-Hexadecane | terpene/terpenoid |
| n-Hexadecanoic acid | terpene/terpenoid |
| n-Hexyl 2-methylbutanoate | terpene/terpenoid |
| n-Hexyl butanoate | terpene/terpenoid |
| N-Methyl methyl anthranilate | terpene/terpenoid |
| n-Nonanal | terpene/terpenoid |
| n-Nonane | terpene/terpenoid |
| n-Nonanol | terpene/terpenoid |
| n-Nonyl acetate | terpene/terpenoid |
| n-Octadecane | terpene/terpenoid |
| n-Octanal | terpene/terpenoid |
| n-Octanoic acid | terpene/terpenoid |
| n-Octyl butanoate | terpene/terpenoid |
| n-Octyl hexanoate | terpene/terpenoid |
| n-Pentacosane (C-25) | terpene/terpenoid |
| n-Pentadecane | terpene/terpenoid |
| n-Pentylbenzene | terpene/terpenoid |
| n-Propyl 4-hydroxybenzoate | terpene/terpenoid |
| n-Tetracosane (C-24) | terpene/terpenoid |
| n-Tetradecane | terpene/terpenoid |
| n-Tetradecanoic acid | terpene/terpenoid |
| n-Tricosane (C-23) | terpene/terpenoid |
| n-Tridecanal | terpene/terpenoid |
| n-Tridecane | terpene/terpenoid |
| n-Undecane | terpene/terpenoid |
| Naginata ketone alcohol | terpene/terpenoid |
| Nardosina-1(10),11-diene | terpene/terpenoid |
| Nardosina-7,9-dien-11-ol | terpene/terpenoid |
| Nardosina-7,9,11-triene | terpene/terpenoid |
| Nardosina-9,11-diene | terpene/terpenoid |
| Naviculol | terpene/terpenoid |
| Neoiso-isopulegol | terpene/terpenoid |
| Neoiso-isopulegol acetate | terpene/terpenoid |
| Neoisomenthol | terpene/terpenoid |
| Neoisopulegol | terpene/terpenoid |
| Neoisothujol | terpene/terpenoid |
| Neomenthol | terpene/terpenoid |
| Neomenthyl acetate | terpene/terpenoid |
| Neopetasone | terpene/terpenoid |
| Neophytadiene (Isomer 1) | terpene/terpenoid |
| Neophytadiene (Isomer 2) | terpene/terpenoid |
| Neophytadiene (Isomer 3) | terpene/terpenoid |
| Neothujol | terpene/terpenoid |
| Neotrifaradiene | terpene/terpenoid |
| Nepetalacton (Isomer 2) | terpene/terpenoid |
| Nepetalactone (Isomer 1) | terpene/terpenoid |
| Neral | terpene/terpenoid |
| Nerol | terpene/terpenoid |
| Nerol oxide | terpene/terpenoid |

TABLE 2-continued

| | |
|---|---|
| Neryl acetate | terpene/terpenoid |
| Neryl formate | terpene/terpenoid |
| Neryl isobutyrate | terpene/terpenoid |
| Neryl acetone | terpene/terpenoid |
| Nerylpropionate | terpene/terpenoid |
| Non-l-en-3-ol | terpene/terpenoid |
| Non-1-ene | terpene/terpenoid |
| Nona-2,4-dienal | terpene/terpenoid |
| Nonadecane | terpene/terpenoid |
| Nonanoic acid | terpene/terpenoid |
| Nootkatene | terpene/terpenoid |
| Nootkatone | terpene/terpenoid |
| Nordavanone | terpene/terpenoid |
| Norpatchoulenol | terpene/terpenoid |
| Norpinguisone | terpene/terpenoid |
| Norrotundene | terpene/terpenoid |
| o-Anisaldehyde | terpene/terpenoid |
| o-Cresol | terpene/terpenoid |
| o-Cymene | terpene/terpenoid |
| o-Cymenene | terpene/terpenoid |
| o-Guiacol | terpene/terpenoid |
| Oct-1-en-3-yl butyrate | terpene/terpenoid |
| Oct-3-en-1-ol (Isomer 1) | terpene/terpenoid |
| Oct-3-en-1-ol (Isomer 2) | terpene/terpenoid |
| Octadecanal | terpene/terpenoid |
| Octadecanoic acid | terpene/terpenoid |
| Octadecyl acetate | terpene/terpenoid |
| Octyl acetate | terpene/terpenoid |
| Opposita-4(15),11-diene | terpene/terpenoid |
| Opposita-4(15),7-diene | terpene/terpenoid |
| Oreodaphnenol | terpene/terpenoid |
| Osmorhizol | terpene/terpenoid |
| Oxidocadalene | terpene/terpenoid |
| Oxidohimachalene | terpene/terpenoid |
| Oxidoselina-1,3,7(11)-trien-8-one | terpene/terpenoid |
| Oxoisoambrox | terpene/terpenoid |
| Oxoisophorone | terpene/terpenoid |
| p-Anisaldehyde | terpene/terpenoid |
| p-Camphorene | terpene/terpenoid |
| p-Cresol | terpene/terpenoid |
| p-Cymene | terpene/terpenoid |
| p-Cymenene | terpene/terpenoid |
| p-Ethylanisol | terpene/terpenoid |
| p-Isopropylbenzaldehyd | terpene/terpenoid |
| p-Isopropylbenzyl alcohol | terpene/terpenoid |
| p-Menth-1-en-9-al (Isomer 1) | terpene/terpenoid |
| p-Menth-1-en-9-al (Isomer 2) | terpene/terpenoid |
| p-Menth-1-ene | terpene/terpenoid |
| p-Mentha-1,3,8-triene | terpene/terpenoid |
| p-Mentha-1,5-diene-8-ol | terpene/terpenoid |
| p-Mentha-2,4(8)-diene | terpene/terpenoid |
| p-Mentha-3,8-diene | terpene/terpenoid |
| p-Methylacetophenone | terpene/terpenoid |
| p-Methylanisol | terpene/terpenoid |
| Pacifigorgia-1,10-diene | terpene/terpenoid |
| Pacifigorgia-1(6),10-diene | terpene/terpenoid |
| Pacifigorgia-1(9),10-diene | terpene/terpenoid |
| Pacifigorgia-2,10-diene | terpene/terpenoid |
| Pacifigorgia-2(10),11-diene | terpene/terpenoid |
| Pacifigorgia-6,10-diene | terpene/terpenoid |
| Pacifigorgiol | terpene/terpenoid |
| Palustrol | terpene/terpenoid |
| Panaginsene | terpene/terpenoid |
| Panaxene | terpene/terpenoid |
| Patchenol | terpene/terpenoid |
| Patchoula-2,4(15)-diene | terpene/terpenoid |
| Patchouli alcohol | terpene/terpenoid |
| Peculiaroxide | terpene/terpenoid |
| Pentadecanal | terpene/terpenoid |
| Pentadecanoic acid | terpene/terpenoid |
| Pentalenene | terpene/terpenoid |
| Perfora-1,7-diene | terpene/terpenoid |
| Perilla alcohol | terpene/terpenoid |
| Perilla aldehyde | terpene/terpenoid |
| Perillene | terpene/terpenoid |
| Petasitene | terpene/terpenoid |
| Pethybrene | terpene/terpenoid |
| Peucedanin | terpene/terpenoid |
| Phantolide | terpene/terpenoid |
| Phenylacetaldehyde | terpene/terpenoid |
| Phenylacetonitrile | terpene/terpenoid |
| Phenylethyl benzoate | terpene/terpenoid |
| Phenylethyl phenylacetate | terpene/terpenoid |
| Phenylethyl propionate | terpene/terpenoid |
| Phenylethyl tiglate | terpene/terpenoid |
| Photocitral A | terpene/terpenoid |
| Photocitral B | terpene/terpenoid |
| Photosantalol | terpene/terpenoid |
| Phyllocladene | terpene/terpenoid |
| Phytane | terpene/terpenoid |
| Phytol | terpene/terpenoid |
| Pimara-8,15-diene | terpene/terpenoid |
| Pimara-8(14),15-diene | terpene/terpenoid |
| Pinguisanene | terpene/terpenoid |
| Pinguisanine | terpene/terpenoid |
| Pinguisone | terpene/terpenoid |
| Pinocamphone | terpene/terpenoid |
| Pinocarvone | terpene/terpenoid |
| Piperitenone | terpene/terpenoid |
| Piperitenone oxide | terpene/terpenoid |
| Piperiton epoxid | terpene/terpenoid |
| Piperitone | terpene/terpenoid |
| Piperonal | terpene/terpenoid |
| Pityol | terpene/terpenoid |
| Plagiochilide | terpene/terpenoid |
| Plagiochiline H | terpene/terpenoid |
| Plagiochilline T | terpene/terpenoid |
| Plagiochilline U | terpene/terpenoid |
| Plagiooxide | terpene/terpenoid |
| Platyphyllol | terpene/terpenoid |
| Pogostol | terpene/terpenoid |
| Polygodial | terpene/terpenoid |
| Porosadienol | terpene/terpenoid |
| Pregeijerene | terpene/terpenoid |
| Premnaspirodiene | terpene/terpenoid |
| Prenyllimonene (Isomer 1) | terpene/terpenoid |
| Prenyllimonene (Isomer 2) | terpene/terpenoid |
| Presilphiperfol-1-ene | terpene/terpenoid |
| Presilphiperfol-7-ene | terpene/terpenoid |
| Presilphiperfolane-9a-ol | terpene/terpenoid |
| Prezizaene | terpene/terpenoid |
| Pristane | terpene/terpenoid |
| Propyl benzoate | terpene/terpenoid |
| Protoillud-6-ene | terpene/terpenoid |
| Pseudodiosphenol | terpene/terpenoid |
| Pseudowiddrene | terpene/terpenoid |
| Puleganolide (Isomer 1) | terpene/terpenoid |
| Puleganolide (Isomer 2) | terpene/terpenoid |
| Pulegone | terpene/terpenoid |
| Pulegone epoxide | terpene/terpenoid |
| Rearrangement product from Grimaldone | terpene/terpenoid |
| Rimuene | terpene/terpenoid |
| Rosa-5,15-diene | terpene/terpenoid |
| Rosefuran | terpene/terpenoid |
| Rosefuran epoxide | terpene/terpenoid |
| Rosifoliol | terpene/terpenoid |
| Rotundene | terpene/terpenoid |
| S,S-Dimethyl dithiocarbonate | terpene/terpenoid |
| Sabina ketone | terpene/terpenoid |
| Sabinene | terpene/terpenoid |
| Saccogynol | terpene/terpenoid |
| Safranal | terpene/terpenoid |
| Safrol | terpene/terpenoid |
| Salicylaldehyde | terpene/terpenoid |
| Salviadienol | terpene/terpenoid |
| Salvial-4(14)-en-1-one | terpene/terpenoid |
| Sandela | terpene/terpenoid |
| Sandvicene | terpene/terpenoid |
| Santene | terpene/terpenoid |
| Santolina alcohol | terpene/terpenoid |
| Santolinatriene | terpene/terpenoid |
| Sarisane | terpene/terpenoid |
| Sativene | terpene/terpenoid |
| Scapanol | terpene/terpenoid |
| Sclarene | terpene/terpenoid |
| Sclareol | terpene/terpenoid |
| Sclareolide | terpene/terpenoid |
| Scopoletine | terpene/terpenoid |
| Selina-1,3,7(11)-trien-8-one | terpene/terpenoid |
| Selina-2,4-diene | terpene/terpenoid |

TABLE 2-continued

| | |
|---|---|
| Selina-3,5-diene | terpene/terpenoid |
| Selina-3,6-diene | terpene/terpenoid |
| Selina-3,7-diene | terpene/terpenoid |
| Selina-3,7(11)-diene | terpene/terpenoid |
| Selina-4,11-diene | terpene/terpenoid |
| Selina-4,7-diene | terpene/terpenoid |
| Selina-4(15),11-dien-8-ol | terpene/terpenoid |
| Selina-4(15),5-diene | terpene/terpenoid |
| Selina-4(15),6-diene | terpene/terpenoid |
| Selina-4(15),7-diene | terpene/terpenoid |
| Selina-4(15),7,11-triene | terpene/terpenoid |
| Selina-4(15),7(11)-diene | terpene/terpenoid |
| Selina-5,11-diene | terpene/terpenoid |
| Sencyunolide | terpene/terpenoid |
| Sesamol | terpene/terpenoid |
| Sesquichamaenol | terpene/terpenoid |
| Sesquicineol | terpene/terpenoid |
| Sesquisabinene A | terpene/terpenoid |
| Sesquisabinene B | terpene/terpenoid |
| Sesquithujene | terpene/terpenoid |
| Seudenol | terpene/terpenoid |
| Seychellene | terpene/terpenoid |
| Silphin-1-ene | terpene/terpenoid |
| Silphiperfol-5-en-3-one | terpene/terpenoid |
| Silphiperfol-6-ene | terpene/terpenoid |
| Silphiperfola-5,7(14)-diene | terpene/terpenoid |
| Silphiperfolene-5-ol | terpene/terpenoid |
| Smyrnicordifuran | terpene/terpenoid |
| Spathulenol | terpene/terpenoid |
| Spirolepechinene | terpene/terpenoid |
| Spirovetiva-1(10),6-diene | terpene/terpenoid |
| Spirovetiva-1(10),7(11)-diene | terpene/terpenoid |
| Stema-13-ene | terpene/terpenoid |
| Striatene | terpene/terpenoid |
| Striatol | terpene/terpenoid |
| syn-Copalol | terpene/terpenoid |
| Syringa aldehyde | terpene/terpenoid |
| T-Cadinol | terpene/terpenoid |
| T-Muurolol | terpene/terpenoid |
| Tamariscene | terpene/terpenoid |
| Tamariscol | terpene/terpenoid |
| Taylocyclan | terpene/terpenoid |
| Taylofuran | terpene/terpenoid |
| Taylorione | terpene/terpenoid |
| Taynudol | terpene/terpenoid |
| Tenuifolene | terpene/terpenoid |
| Terpinen-4-ol | terpene/terpenoid |
| Terpinen-4-ol acetate | terpene/terpenoid |
| Terpinolene | terpene/terpenoid |
| Tetradecanal | terpene/terpenoid |
| Tetradecyl acetate | terpene/terpenoid |
| Theaspirane (Isomer 1) | terpene/terpenoid |
| Theaspirane (Isomer 2) | terpene/terpenoid |
| Thuja-2,4(10)-diene | terpene/terpenoid |
| Thujopsa-3-one | terpene/terpenoid |
| Thujopsadiene | terpene/terpenoid |
| Thujopsan-2a-ol | terpene/terpenoid |
| Thujopsane-2b-ol | terpene/terpenoid |
| Thujopsene | terpene/terpenoid |
| Thymohydroquinone | terpene/terpenoid |
| Thymol | terpene/terpenoid |
| Thymol acetate | terpene/terpenoid |
| Thymol isobutyrate | terpene/terpenoid |
| Thymol methyl ether | terpene/terpenoid |
| Thymoquinone | terpene/terpenoid |
| Tonalide | terpene/terpenoid |
| Torilenol | terpene/terpenoid |
| Trachylobane | terpene/terpenoid |
| trans-10-Hydroxycalamenene | terpene/terpenoid |
| trans-2-Hydroxycalamenene | terpene/terpenoid |
| trans-4,8a-Dimethyl-4a,5-epoxydecaline | terpene/terpenoid |
| trans-6-Hydroxyisocalamenene | terpene/terpenoid |
| trans-6,6,10-Trimethyl-2-decalone | terpene/terpenoid |
| trans-8-Acetylthio-p-mentan-3-one | terpene/terpenoid |
| trans-8-Mercapto-p-menthan-3-one | terpene/terpenoid |
| trans-a-Bergamotene | terpene/terpenoid |
| trans-Anethol | terpene/terpenoid |
| trans-Arbusculone | terpene/terpenoid |
| trans-b-Bergamotene | terpene/terpenoid |
| trans-Bisabola-1(6),10-dien-2,3-diol | terpene/terpenoid |

TABLE 2-continued

| | |
|---|---|
| trans-Calamenene | terpene/terpenoid |
| trans-Carveol | terpene/terpenoid |
| trans-Carvone epoxide | terpene/terpenoid |
| trans-Carvyl acetate | terpene/terpenoid |
| trans-Carvyl propionate | terpene/terpenoid |
| trans-Chrysanthemol | terpene/terpenoid |
| trans-Chrysanthenol | terpene/terpenoid |
| trans-Chrysanthenyl acetate | terpene/terpenoid |
| trans-Dauca-4(11),7-diene | terpene/terpenoid |
| trans-Dauca-4(11),8-diene | terpene/terpenoid |
| trans-Dihydrocarvone | terpene/terpenoid |
| trans-Dihydrocarvone epoxide | terpene/terpenoid |
| trans-Dihydromultifidene | terpene/terpenoid |
| trans-Dihydroroseoxide | terpene/terpenoid |
| trans-Dracunculifoliol | terpene/terpenoid |
| trans-Epoxypseudoisoeugenol tiglate | terpene/terpenoid |
| trans-Epoxypseudoisoeugenyl-2-methylbutyrate | terpene/terpenoid |
| trans-Ethyl chrysanthemate | terpene/terpenoid |
| trans-Eudesma-3,5-diene | terpene/terpenoid |
| trans-Hormosirene | terpene/terpenoid |
| trans-Isolimonene | terpene/terpenoid |
| trans-Isopulegone | terpene/terpenoid |
| trans-Limonene oxide | terpene/terpenoid |
| trans-Linalool oxide acetate | terpene/terpenoid |
| trans-Linalooloxide (furanoid) | terpene/terpenoid |
| trans-Myrtanol | terpene/terpenoid |
| trans-p-Menth-2-en-1-ol | terpene/terpenoid |
| trans-p-Menth-2-en-1-ol | terpene/terpenoid |
| trans-p-Mentha-1(7),8-dien-2-ol | terpene/terpenoid |
| trans-p-Mentha-2,8-dien-1-ol | terpene/terpenoid |
| trans-Pinane | terpene/terpenoid |
| trans-Pinocarveol | terpene/terpenoid |
| trans-Pinocarvyl acetate | terpene/terpenoid |
| trans-Pinocarvyl formate | terpene/terpenoid |
| trans-Piperitol | terpene/terpenoid |
| trans-Rose oxide | terpene/terpenoid |
| trans-Sabinen hydrate acetate | terpene/terpenoid |
| trans-Sabinene hydrate | terpene/terpenoid |
| trans-Sabinol | terpene/terpenoid |
| trans-Sabinyl acetate | terpene/terpenoid |
| trans-Sesquisabinen hydrate | terpene/terpenoid |
| trans-Spiroether | terpene/terpenoid |
| trans-Thiorose oxide | terpene/terpenoid |
| trans-Totarol | terpene/terpenoid |
| trans-Verbenol | terpene/terpenoid |
| Traseolide | terpene/terpenoid |
| Trichocoleine | terpene/terpenoid |
| Trichodiene | terpene/terpenoid |
| Tricyclene | terpene/terpenoid |
| Tridensenal | terpene/terpenoid |
| Tridensenone | terpene/terpenoid |
| Tridenson | terpene/terpenoid |
| Trifara-9,14-diene | terpene/terpenoid |
| Trinoranastreptene | terpene/terpenoid |
| Tritomarene | terpene/terpenoid |
| Tuberolactone | terpene/terpenoid |
| Umbellulone | terpene/terpenoid |
| Undeca-1,3,5-triene (Isomer 1) | terpene/terpenoid |
| Undecanal | terpene/terpenoid |
| Undecanoic acid | terpene/terpenoid |
| Valenca-2,9,11-triene | terpene/terpenoid |
| Valencene | terpene/terpenoid |
| Valeranone | terpene/terpenoid |
| Valerena-4,7(11)-diene | terpene/terpenoid |
| Valerenal | terpene/terpenoid |
| Valerenic acid | terpene/terpenoid |
| Valerianol | terpene/terpenoid |
| Valpara-2,15-diene | terpene/terpenoid |
| Vanilline | terpene/terpenoid |
| Ventricos-7(13)-ene | terpene/terpenoid |
| Verbenene | terpene/terpenoid |
| Verbenone | terpene/terpenoid |
| Verticilla-4(20),7,11-triene | terpene/terpenoid |
| Veticadine oxide | terpene/terpenoid |
| Vetiselinol | terpene/terpenoid |
| Vetivazulene | terpene/terpenoid |
| Vinylguaiacol | terpene/terpenoid |
| Viridene | terpene/terpenoid |
| Viridiflorol | terpene/terpenoid |
| Viscida-4,9,14-triene | terpene/terpenoid |

TABLE 2-continued

| | |
|---|---|
| Vulgarone A | terpene/terpenoid |
| w-Amorphene | terpene/terpenoid |
| w-Cadinene | terpene/terpenoid |
| Widdrol | terpene/terpenoid |
| Xanthorhizol | terpene/terpenoid |
| Ylanga-2,4(15)-diene | terpene/terpenoid |
| Yomogialcohol | terpene/terpenoid |
| Z-Cinnamaldehyde | terpene/terpenoid |
| Zierene | terpene/terpenoid |
| Zingiberene | terpene/terpenoid |
| Zingiberenol | terpene/terpenoid |
| Zizaene | terpene/terpenoid |
| Zizaenic acid | terpene/terpenoid |
| Zizanol | terpene/terpenoid |
| Zonarene | terpene/terpenoid |

TABLE 3

| | |
|---|---|
| Agarwood | essential oil |
| Ajowan | essential oil |
| ambrette | essential oil |
| Amyris | essential oil |
| Amyris | essential oil |
| Anethi | essential oil |
| angelica archangelica | essential oil |
| angelica glauca | essential oil |
| Arnica | essential oil |
| artemisia annua | essential oil |
| artemisia tridentata ambrette | essential oil |
| artemisia vestata | essential oil |
| ashwaghanda | essential oil |
| bay laurel | essential oil |
| beeswax absolute | essential oil |
| benzoin | essential oil |
| bergamot | essential oil |
| bergamot mint | essential oil |
| black currant bud absolute | essential oil |
| black pepper | essential oil |
| blood orange | essential oil |
| blue lotus absolute | essential oil |
| blue lotus absolute | essential oil |
| blue tansy | essential oil |
| Boronia | essential oil |
| buchu betulina | essential oil |
| buchu crenulata | essential oil |
| Bulgarian | essential oil |
| butter CO2 | essential oil |
| cade | essential oil |
| Cajeput | essential oil |
| Calamus | essential oil |
| Cannabis | essential oil |
| cape chamomile | essential oil |
| cape may | essential oil |
| cape snowbush | essential oil |
| caraway | essential oil |
| caraway CO2 | essential oil |
| cardamom | essential oil |
| cardamom CO2 | essential oil |
| carnation absolute | essential oil |
| carrot | essential oil |
| Carvacrol | essential oil |
| cassia CO2 | essential oil |
| cedarwood | essential oil |
| cedarwood absolute | essential oil |
| cedarwood Atlas | essential oil |
| cedarwood Himalayan | essential oil |
| cedarwood Texas | essential oil |
| cedarwood Virginia | essential oil |
| celery seed | essential oil |
| chamomile blue | essential oil |
| chamomile blue CO2 | essential oil |
| chamomile Roman | essential oil |
| champaca absolute | essential oil |
| champaca absolute red | essential oil |
| champaca CO2 | essential oil |
| choya loban | essential oil |
| cilantro | essential oil |

TABLE 3-continued

| | |
|---|---|
| cinnamon bark | essential oil |
| cinnamon leaf | essential oil |
| cistus | essential oil |
| Citronella | essential oil |
| clary sage | essential oil |
| clary sage | essential oil |
| clary sage absolute | essential oil |
| clove bud | essential oil |
| clove leaf | essential oil |
| cocoa bean absolute | essential oil |
| cocoa bean absolute organic | essential oil |
| coconut pulp CO2 | essential oil |
| coffee bean CO2 | essential oil |
| cognac green | essential oil |
| cognac white | essential oil |
| copaiba balsam | essential oil |
| coriander | essential oil |
| Coriander | essential oil |
| coriander seed | essential oil |
| coriander seed CO2 | essential oil |
| cumin black CO2 | essential oil |
| curry leaf | essential oil |
| cypress | essential oil |
| cypress blue | essential oil |
| davana | essential oil |
| desert sage | essential oil |
| Douglas fir | essential oil |
| Elemi | essential oil |
| eucalyptus blue gum | essential oil |
| eucalyptus calophylla | essential oil |
| eucalyptus citriodora | essential oil |
| eucalyptus dives | essential oil |
| eucalyptus globulus | essential oil |
| eucalyptus lemon | essential oil |
| eucalyptus macarthurii | essential oil |
| eucalyptus malee | essential oil |
| eucalyptus radiata | essential oil |
| eucalyptus sideroxylon | essential oil |
| eucalyptus sieberi | essential oil |
| eucalyptus smithii | essential oil |
| Fennel | essential oil |
| fenugreek CO2 | essential oil |
| fir balsam | essential oil |
| fir balsam absolute | essential oil |
| fir balsam organic | essential oil |
| fir Siberian | essential oil |
| fragonia {TM} | essential oil |
| frangiapani absolute | essential oil |
| frankincense carterii | essential oil |
| frankincense CO2 | essential oil |
| frankincense CO2 India | essential oil |
| frankincense frereana | essential oil |
| frankincense frereana organic | essential oil |
| frankincense negleta | essential oil |
| frankincense Omangalangal CO2 | essential oil |
| frankincense papyrifera | essential oil |
| frankincense sacra | essential oil |
| frankincense serrata | essential oil |
| frankincense Somalia | essential oil |
| galanga CO2 | essential oil |
| galbanum CO2 | essential oil |
| galbanum CO2 | essential oil |
| Geranium | essential oil |
| geranium absolute | essential oil |
| geranium Africa organic | essential oil |
| geranium Egypt organic | essential oil |
| Ginger | essential oil |
| ginger CO2 | essential oil |
| ginger fresh | essential oil |
| grapefruit | essential oil |
| grapefruit organic | essential oil |
| grapefruit pink | essential oil |
| grapefruit white | essential oil |
| hay absolute | essential oil |
| Helichrysum | essential oil |
| helichrysum arenarium | essential oil |
| helichrysum bractiferium | essential oil |
| helichrysum gymnocephalum | essential oil |
| helichrysum Italicum | essential oil |
| helichrysum odorattisum | essential oil |

TABLE 3-continued

| | |
|---|---|
| helichrysum organic | essential oil |
| helichrysum orientale | essential oil |
| helichrysum petiolare | essential oil |
| helichrysum pumilum | essential oil |
| helichrysum sanguineum | essential oil |
| helichrysum splendium | essential oil |
| hemp | essential oil |
| hinoki wood | essential oil |
| holy basil | essential oil |
| hyssop decumbens | essential oil |
| immortelle absolute | essential oil |
| Indian basil | essential oil |
| innula | essential oil |
| Intermedia | essential oil |
| jasmine absolute Egypt | essential oil |
| jasmine absolute India | essential oil |
| jasmine grandiflorum absolute | essential oil |
| jasmine organic extract | essential oil |
| jasmine sambac absolute | essential oil |
| juniper berry | essential oil |
| juniper berry CO2 | essential oil |
| juniper berry CO2 organic | essential oil |
| juniper berry organic | essential oil |
| juniper leaf | essential oil |
| katafray | essential oil |
| khella | essential oil |
| khella organic | essential oil |
| Kunzea | essential oil |
| Labdanum | essential oil |
| labdanum absolute | essential oil |
| labdanum absolute clear | essential oil |
| labdanum CO2 | essential oil |
| Lanyana | essential oil |
| Laurel | essential oil |
| Lavandin | essential oil |
| lavandin grosso | essential oil |
| lavandula antinea | essential oil |
| lavandula nimmoi | essential oil |
| lavandula stoechas | essential oil |
| lavandula x | essential oil |
| lavender | essential oil |
| lavender absolute | essential oil |
| lavender English | essential oil |
| lavender French | essential oil |
| lavender grosso | essential oil |
| lavender Kashmir | essential oil |
| lavender latifolia | essential oil |
| lavender Seville | essential oil |
| lavender spike | essential oil |
| leaf organic | essential oil |
| leleshwa | essential oil |
| Lemon | essential oil |
| lemon myrtle | essential oil |
| Lemon organic | essential oil |
| lemon tea tree | essential oil |
| lemon verbena | essential oil |
| Lemongrass | essential oil |
| Lemongrass | essential oil |
| lemongrass organic | essential oil |
| lemongrass wild | essential oil |
| Lime | essential oil |
| lime distilled | essential oil |
| lime expressed | essential oil |
| linden blossom CO2 | essential oil |
| lippia javanica | essential oil |
| Liquidambar | essential oil |
| Litsea Cubeba | essential oil |
| lovage | essential oil |
| mandarin | essential oil |
| mandarin green | essential oil |
| mandarin red | essential oil |
| mandarin yellow | essential oil |
| manuka | essential oil |
| manuka wild | essential oil |
| marjoram | essential oil |
| marjoram organic | essential oil |
| marjoram sweet | essential oil |
| mastic leaf | essential oil |
| mimosa absolute | essential oil |
| Mugwort | essential oil |

TABLE 3-continued

| | |
|---|---|
| Myrrh | essential oil |
| Myrrh | essential oil |
| myrrh CO2 | essential oil |
| Myrtle | essential oil |
| nagarmotha | essential oil |
| nartjie | essential oil |
| Neroli | essential oil |
| neroli absolute | essential oil |
| neroli Egypt | essential oil |
| Neroli Morocco | essential oil |
| neroli Tunisia | essential oil |
| niaouli | essential oil |
| oak moss | essential oil |
| oakmoss absolute | essential oil |
| ocimum gratissimum | essential oil |
| opoponax | essential oil |
| orange blood | essential oil |
| orange essence | essential oil |
| Orange sweet | essential oil |
| orange wild | essential oil |
| oregano | essential oil |
| oregano organic | essential oil |
| Orris butter | essential oil |
| orris root | essential oil |
| osmanthus absolute | essential oil |
| Palmarosa | essential oil |
| palmarosa Nepal | essential oil |
| palmarosa organic | essential oil |
| patchouli | essential oil |
| patchouli dark | essential oil |
| patchouli wild | essential oil |
| pepper black | essential oil |
| pepper pink | essential oil |
| peppermint | essential oil |
| peppermint | essential oil |
| peppermint | essential oil |
| peppermint France | essential oil |
| Peppermint India | essential oil |
| peppermint organic | essential oil |
| peppermint U.S.A. | essential oil |
| Peru balsam | essential oil |
| petitgrain | essential oil |
| petitgrain absolute | essential oil |
| petitgrain bigarade | essential oil |
| petitgrain mandarin | essential oil |
| petitgrain sur fleur | essential oil |
| petitgrain sur fleurs | essential oil |
| pine Scotch | essential oil |
| pine wild | essential oil |
| pink lotus absolute | essential oil |
| pink pepper | essential oil |
| Pink peppercorn | essential oil |
| Plai | essential oil |
| raspberry seed CO2 | essential oil |
| ravensara | essential oil |
| Ravintsara | essential oil |
| ravintsara organic | essential oil |
| rhododendron | essential oil |
| Rosalina | essential oil |
| rose absolute | essential oil |
| rose absolute Bulgaria | essential oil |
| rose absolute Egypt | essential oil |
| rose absolute Morocco | essential oil |
| rose CO2 | essential oil |
| rose CO2 organic | essential oil |
| rose de mai | essential oil |
| rose de mai organic extract | essential oil |
| rose essential oil | essential oil |
| rose geranium | essential oil |
| rose leaf absolute | essential oil |
| rose leaf concrete | essential oil |
| rose otto | essential oil |
| rose otto Bulgaria organic | essential oil |
| rose otto Bulgaria organic | essential oil |
| rose otto Turkey | essential oil |
| rose otto white | essential oil |
| rose petal concrete | essential oil |
| rosemary et cineole | essential oil |
| rosemary et cineole organic | essential oil |
| rosemary Spanish | essential oil |

TABLE 3-continued

| | |
|---|---|
| rosemary Tuscan blue | essential oil |
| rosemary verbenone | essential oil |
| Rosewood | essential oil |
| rosewood leaf | essential oil |
| ruby red | essential oil |
| sage | essential oil |
| sage Dalmation | essential oil |
| sage white | essential oil |
| sandalwood | essential oil |
| sandalwood Australia | essential oil |
| sandalwood India | essential oil |
| sandalwood New Caledonia | essential oil |
| sandalwood nut | essential oil |
| sandalwood organic | essential oil |
| sandalwood Royal Hawaiian | essential oil |
| sea buckthorn | essential oil |
| Siberian fir wild | essential oil |
| Spearmint | essential oil |
| spearmint organic | essential oil |
| spearmint USA organic | essential oil |
| spikenard | essential oil |
| spruce absolute black | essential oil |
| spruce Eastern hemlock | essential oil |
| star anise | essential oil |
| tagetes | essential oil |
| tagetes absolute | essential oil |
| Tangerine | essential oil |
| tangerine | essential oil |
| tansy blue | essential oil |
| tea tree | essential oil |
| thyme | essential oil |
| thyme linalool | essential oil |
| thyme red | essential oil |
| thyme thymol | essential oil |
| tobacco absolute | essential oil |
| tonka bean absolute | essential oil |
| tonka bean butter | essential oil |
| tuberose absolute | essential oil |
| Tulip absolute | essential oil |
| tulip tree absolute | essential oil |
| tulsi | essential oil |
| turmeric CO2 | essential oil |
| turmeric CO2 organic | essential oil |
| turmeric organic | essential oil |
| valerian | essential oil |
| vanilla absolute | essential oil |
| vanilla CO2 | essential oil |
| vanilla CO2 | essential oil |
| vanilla oleoresin | essential oil |
| verbena lemon | essential oil |
| vetiver | essential oil |
| vetiver Haiti | essential oil |
| vetiver India | essential oil |
| vetiver Java | essential oil |
| vetiver Madagascar | essential oil |
| violet leaf absolute | essential oil |
| white ginger lily absolute | essential oil |
| white lotus absolute | essential oil |
| wintergreen | essential oil |
| yarrow blue | essential oil |
| ylang ylang 1 | essential oil |
| ylang ylang 2 | essential oil |
| ylang ylang 3 | essential oil |
| ylang ylang absolute | essential oil |
| ylang ylang complete | essential oil |
| ylang ylang extra | essential oil |
| ylang ylang fine | essential oil |
| yuzu zdravetz | essential oil |

TABLE 4

| | |
|---|---|
| Adrenic acid (AdA) | fatty acid |
| Alpha-linolenic acid (ALA) | fatty acid |
| Arachidic acid | fatty acid |
| Behenic acid | fatty acid |
| Bosseopentaenoic acid | fatty acid |
| Butyric acid | fatty acid |
| Capric acid | fatty acid |
| Caproic acid | fatty acid |
| Caprylic acid | fatty acid |
| Carboceric acid | fatty acid |
| Catalpic acid | fatty acid |
| Ceroplastic acid | fatty acid |
| Cerotic acid | fatty acid |
| Cervonic acid | fatty acid |
| Cervonic acid | fatty acid |
| Conjugated Linolenic Acids | fatty acid |
| Crotonic acid | fatty acid |
| Di-unsaturated fatty acid | fatty acid |
| Dihomo-gamma-linolenic acid (DGLA) | fatty acid |
| Dihomo-γ-linolenic acid | fatty acid |
| Docosadienoic acid | fatty acid |
| Docosahexaenoic acid (DHA, Cervonic acid) | fatty acid |
| Docosapentaenoic acid (DPA, Clupanodonic acid) | fatty acid |
| Docosatetraenoic acid | fatty acid |
| Eicosadienoic acid | fatty acid |
| Eicosapentaenoic acid (EPA, Timnodonic acid) | fatty acid |
| Eicosatetraenoic acid (ETA) | fatty acid |
| Eicosenoic acid | fatty acid |
| Elaidic acid | fatty acid |
| Eleostearic acid | fatty acid |
| Enanthic acid | fatty acid |
| Erucic acid | fatty acid |
| Gadoleic acid | fatty acid |
| Gamma-linolenic acid (GLA) | fatty acid |
| Geddic acid | fatty acid |
| Gondoic acid | fatty acid |
| Heneicosapentaenoic acid (HPA) | fatty acid |
| Heneicosylic acid | fatty acid |
| Hentriacontylic acid | fatty acid |
| Heptatriacontylic acid | fatty acid |
| Hexa-unsaturated fatty acids | fatty acid |
| Hexadecatrienoic acid (HTA) | fatty acid |
| Hexatriacontylic acid | fatty acid |
| Jacaric acid | fatty acid |
| Lacceroic acid | fatty acid |
| Lauric acid | fatty acid |
| Lignoceric acid | fatty acid |
| Linoleic acid | fatty acid |
| Linolelaidic acid | fatty acid |
| Linolenic acid | fatty acid |
| Margaric acid | fatty acid |
| Mead acid | fatty acid |
| Melissic acid | fatty acid |
| Mono-unsaturated fatty acid | fatty acid |
| Montanic acid | fatty acid |
| Myristic acid | fatty acid |
| Myristoleic | fatty acid |
| Nervonic acid | fatty acid |
| Nonacosylic acid | fatty acid |
| Nonadecylic acid | fatty acid |
| Nonatriacontylic acid | fatty acid |
| Octatriacontylic acid | fatty acid |
| Oleic acid | fatty acid |
| Ozubondo acid | fatty acid |
| Palmitic acid | fatty acid |
| Palmitoleic acid | fatty acid |
| Paullinic acid | fatty acid |
| Pelargonic acid | fatty acid |
| Pentacosylic acid | fatty acid |
| Pentaunsaturated fatty acids | fatty acid |
| Pinolenic acid | fatty acid |
| Propionic acid | fatty acid |
| Psyllic acid | fatty acid |
| Punicic acid | fatty acid |
| Rumelenic acid | fatty acid |
| Rumenic acid | fatty acid |
| Sapienic acid | fatty acid |
| Sardine acid | fatty acid |
| Sciadonic acid | fatty acid |
| Stearic acid | fatty acid |
| Stearidonic acid | fatty acid |
| Stearidonic acid | fatty acid |
| Stearidonic acid (SDA) | fatty acid |
| Tetra-unsaturated fatty acids | fatty acid |
| Tetracontylic acid | fatty acid |
| Tetracosahexaenoic acid (Nisinic acid) | fatty acid |

TABLE 4-continued

| | |
|---|---|
| Tetracosanolpentaenoic acid | fatty acid |
| Tri-unsaturated fatty acids | fatty acid |
| Tricosylic acid | fatty acid |
| Tridecylic acid | fatty acid |
| Undecylic acid | fatty acid |
| Vaccenic acid | fatty acid |
| Valeric acid | fatty acid |
| α-Calendic acid | fatty acid |
| α-Eleostearic acid | fatty acid |
| α-Linolenic acid | fatty acid |
| α-Parinaric acid | fatty acid |
| β-Calendic acid | fatty acid |
| β-Eleostearic acid | fatty acid |
| β-Parinaric acid | fatty acid |
| γ-Linolenic acid | fatty acid |

In some aspects, contemplated mineral pitch resin products can comprise all cannabinoids. In some contemplated aspects, the mineral pitch resin products can comprise between 1-2, between 1-4, between 1-6, between 1-8, between 1-10, between 4-8, between 5-10, between 1-15, between 5-15, or each of the cannabinoids set forth in Table 1.

In some contemplated aspects, the primary cannabinoid present in the mineral pitch resin product is CBD. In some aspects, the ratio of CBD to other cannabinoids in the mineral pitch resin product may be between 1/10000000 to 99.99/100. In some exemplary aspects, a ready to consume mineral pitch resin products can comprise between 1-100 mg of CBD per 500 mg of the resin product, for example between 20-25 mg of CBD per 500 mg of the resin product (about 5% by weight). But it is contemplated that any suitable cannabinoids may be present in the products in any suitable amounts (e.g., 1-all cannabinoids present in an amount of between 0.000001-1%, between 1-15%, between 1-10%, between 3-8%, or between 0.01 to 99.99% by weight).

Additionally or alternatively, contemplated mineral pitch resin products may comprise any suitable amounts of at least one of terpenes and terpenoids, saturated, monounsaturated and polyunsaturated fatty acids, and essential oils that may be introduced for aromatics and targeted olfactory effect. A truly remarkable aspect of the invention, is that the Applicant was able to observe quick changes in brain frequencies through EEG simply through allowing the test subjects smell the novel shilajit resin with various combinations of ingredients added for aromatics and predetermined olfactory effect. Delta, Theta, Alpha and Beta waves can be changed quickly and effectively to reach desired states of the mind, moods, and even changes in the physiology of the body.

Exemplary methods of manufacturing improved mineral pitch resin products with cannabinoids are described herein.

Example Method 1

A flow chart of an exemplary method 100 of the disclosure is set forth in FIG. 1. Method 100 can comprise an initial step of selecting an area 105 for identifying shilajit bearing rock.

In some embodiments, areas with Cannabis flora for are selected, for example, wherein some or all areas within 1-1,000 meters of natural vegetation of Cannabis/Hemp fauna are identified.

While scouting for the raw material deposits one may optionally record the proximity of cannabis and/or other vegetation to the shilajit bearing rock. The process is high labor and documentation intensive and generally requires knowledge of botany as well as understanding of how to identify shilajit bearing rock ready for harvest. It is contemplated that one may optionally search for evidence of a minimum number of mature cannabis and/or other specific plants within a predetermined proximity of the mineral pitch deposit (e.g., at least 10 mature cannabis plants in proximity of maximum hundred yards away from the mineral pitch deposit) when scouting for suitable raw material deposits. Any evidence that the cannabis plants have been growing in the area for multiple years may be beneficial in identifying a quality raw material as it is likely that natural humification and microbial re-fermentation were taking place for years in such cases, and that metabolites in some form have been deposited into parts of the mineral pitch bearing rock.

Once the raw shilajit bearing rock/stone material has been identified (which may optionally be tested for the authenticity of genuine shilajit bearing rock/stone in the field), the shilajit bearing rock/stone may be collected in accordance with step 110.

Exemplary methods for identifying and processing/collecting genuine raw material are described in detail in U.S. Pat. Nos. 10,967,004 and 10,130,656, which are incorporated by reference in their entireties.

This pitch may be found in stones, which can be found in proximity to mountain slopes facing the sun with proximity of vegetation within one to five (1-5) kilometers. Such stones or formations can be found in the mountain crevices, caves, and the raw resin deposits sometimes may have an appearance of dark gooey matter oozing out of rocks. Visually the raw resin deposits may appear as a part of the crevice, but if extracted, may be 1 to up to 150 cm in depth, and may be mixed with surrounding rock, sand, pebble, residuals of local plants.

Measuring the identified raw material may be done with simple measuring tape or a ruler. To measure the depth of how deep the deposit in the stones are in a crevice or a rock, a measuring rod with a scale may be used, which allows to identify the depth of the stone. The color of the raw material can range from very dark brown, to red, yellow and shades of white. The presence of white indicates that microorganisms beneficial to the raw material will be properly populated and have processed the matter. Such microorganisms include simple yeasts and aerobic bacteria, which creates multiple metabolites that give the resin its health properties.

In order to determine if the raw material is suitable, it may be tested in the field. In some aspects, the material may be tested for the presence of glycine prior to collection. In some aspects, the material may be tested for the presence of above a threshold amount of glycine (e.g., at least 0.1%, at least 1%, at least 3, at least 5%, at least 10%, at least 15%, at least 25% or even more glycine). In order to be suitable for collection, the material will preferably contain some glycine. Once the raw material is identified the exterior layer may be grated off (e.g., an exterior layer having a depth of between 0.1-10 cm, between 0.1-7 cm, between 0.1-5 cm, between 1-5 cm, between 1-3 cm), and a selected amount of raw material may be taken for testing. The collected raw material may be mixed in predetermined quantities with water and triketohydrindene monohydrate or other reagent suitable for testing for presence of glycine. In some contemplated aspects, a preferred ratio for testing the raw material is one part raw material to one part monohydrate to eight parts water. The mixture may be boiled and then cooled down (e.g., boiled for 5-30 min and cooled down for 5-30 min). Once fully settled, the solution generally has a color ranging from blue to purple. The ideal raw material has a color in the blue violet range, which is indicative of a good amount of glycine being present. This basic initial test suffices for identification of glycine in the raw material amino acids. Later, once the material has been harvested and processed, the presence of Glycine may be reconfirmed with more accurate quantitative and qualitative methods which include High-Performance Liquid Chromatography (HPLC) or infrared (IR) spectrography or any conventional United States Pharmacopeial Convention (USP) accepted method. It may be at this stage that the raw material is deemed suitable for collection and further processing. The raw material can simply be picked by hand or extracted with pickaxes or any firm objects that may separate it from the rock, stone or location.

Conventionally, when one collects shilajit bearing rock, the material is commingled, and often no attention is given to the smaller lots as they are seen as not economically viable to collect and transport. Here, it is contemplated that any raw material deposit, for example, lots ranging from 50 g up to 500 kg or more can be collected, separated and stored differently within containers, for example, containers or compartments which allow no more than 1 kg of total weight of the stored material. It is contemplated that any suitable number of lots (e.g., 100-10,000) can be collected and the containers can be marked with the exact GPS location of collection. Each lot can be kept separate and not mixed, for example, until a later step in the method (e.g., after testing each lot for a threshold amount of glycine and/or cannabinoids or other components). Where one is collecting material that exceeds the weight that selected containers or compartments may hold, the shilajit bearing rock may be cut into smaller pieces which can fit into the containers or compartments (e.g., the 1 kg compartments or containers). The raw material separation may take place from top to bottom, and from the sides to center. Such a method for cutting is novel for the collection of shilajit raw material. The reason for cutting in this manner is to create separation of layers which formed over time, and where deposits of cannabinoids, minerals, and metabolites may have taken place over time. Further, during processing and testing of the resin cutting and collection process described herein should allow for identification of the parts which contain the most of the desired material, its depth or location within the larger deposit, and for proper extraction.

Another contemplated step of this exemplary method is to transport the material to the production facility for lab testing. Once collected the raw resin material may be placed in one or more coolers, for example, a thermo electric cooler or coolers, which maintain internal temperatures lower than 39 degrees Celsius. The coolers may be transported to a facility where the air is continuously purified of environmental pollutants, airborne microbes, dust particles, aerosol particles, and any chemical vapors. In this controlled manufacturing environment, or clean room, the air at any time adjacent to the resin may have minimal or no particles in the air. This may be achieved through controlled enclosures and proper air filtration. The temperature of one or more of the manufacturing space, the vessel, tank or other device in which the resin is being processed, and the resin may advantageously be kept at or under 39 degrees Celsius at all times. In some embodiments, once materials are removed from the containers, they may be tested for the presence of major and minor cannabinoids and glycine, and/or any other suitable components, in accordance with step 115. The positive identification of a desired glycine content, a desired cannabinoid content, and/or a desired content of any other component could optionally be performed at any point. The positive identification of a suitable amount of glycine and a suitable amounts of cannabinoids may be a combination desired for the raw material to manufacture mineral pitch resin products described herein. However, it should be appreciated that some contemplated methods do not require that the raw material contain any cannabinoids.

Each available lot may be tested as set forth in step 115. In some embodiments, each lot can be tested for a combination of at least three major cannabinoids, 1 minor cannabinoid, and naturally containing glycine. Lots which include at least three major cannabinoids, 1 minor cannabinoid, and naturally containing glycine may be further processed while lots that do not may be discarded or set aside. Lots separation may be maintained. Additionally or alternatively, the lots which have shown similar characteristics at this point either can be further processed separately or together (two or more lots).

Once removed from the containers (and optionally tested), the raw resin material may be grated and/or washed, in accordance with step 120. In some embodiments, the raw resin materials be briefly washed off or immersed in up to 99% pure $CH_3CH_2OH$ (ethanol) in possible combination with H20, or in another suitable solution or liquid. In some embodiments, the external layer(s) containing impurities may be removed with a sharp object like a chisel or a grater or any object with similar or identical functions. Once the external layers are removed the material may be washed or placed into food grade alcohol or any other suitable solution or liquid. Lot separation may be maintained in the same manner the lots were maintained prior to step 120.

Further dissolution, in accordance with step 125, of the previously qualified material may take place. In some embodiments, raw material can be dissolved in water not exceeding 39 degrees Celsius, and dissolution of material may be expedited by agitating at various RPMs ranging from 0.1 up to 25,000 RPMs. Such water may be considered sterile and contain less than 0.25 USP Endotoxin unit per ml with any microscopically detectable particles absent. Initially the water may contain under 10 ppm, under 5 ppm, under 1 ppm, under 0.1 ppm of dissolved solids, or even less. The material may be combined with water in proportions necessary to turn the combination into a free-flowing liquid. Lot separation may be maintained in the same manner the lots were maintained prior to step 125.

In some embodiments, different types of water can be used depending on the type of processed resin which is desired. Minerals, herbal extracts and biologically active substances may be added to the water. The water used may be from sources from specific locations which were previously global positioning system (GPS) identified, the water can be passed through a magnetic field of 1 to 20000 Gauss, or exposed to sound frequencies from 0.1 to 10,000 HZ (e.g., 5 Hz, 7.83 Hz, 3-25 Hz, 3-50 Hz, 432 Hz, 528 Hz, 80-900 Hz, 2,000-2,200 Hz). The material and water may be present in any suitable ratio. The raw resin material may further be dissolved by letting it dissolve passively or agitating it mechanically with any immersed tool that moves at speeds of, for example, less or equal to 0.1 rpm.

Next the solution may be filtered, in accordance with step 130. In some embodiments, the solution may be filtered through various filters under pressure, for example through multiple size filters, optionally from higher pore size to smaller pores size. Filters may range from several millimeters down to several microns. This procedure eliminates undesired pebble, sand, sediment, fiber, and large particles. Eventually the solution will pass passively or under pressure through a filter with a pore size equal or possible even less than 0.03 microns. This allows for the filtrate to come out that later will result into manufacturing of highly bioavailable resin, with particles eliminated, which cannot be easily absorbed by the human body. This procedure may require pressure in order to properly filter out the particles not desired due to the lack of bioavailability and manage the production time for the resin. The pressure may be produced either mechanically by a piston or similar device, or gas such as compressed air. Pressure in such case may be sufficient to effectively push the solution through the numerous filter, the pressure being equal (passive) or above 1 psi and up to 14.7 psi or even higher if the technical capability permits. The process may be repeated multiple times. Dissolution and filtration may be repeated up to 50 times with different amounts of water solvent, agitation and filtration. Lot separation may be maintained as was maintained prior to dissolution and/or filtration.

At any stage before, during or after the filtration process, herbal extracts or minerals can be added to the solution in any form, as could cannabinoids in any form as further described below, and/or Essential oils, terpenes, terpenoids, and/or saturated, monounsaturated and/or polyunsaturated fatty acids. These ingredients can be added to the point of emulsification of the resin with such ingredients. Due to the fact that the resin improves effect of herbs on the body, it can be beneficial to combine the resin and the herbal extracts, essential oils, fatty acids, cannabinoids, terpenes, and/or terpenoids. Extracts can be received through different processes, and can be introduced in form of liquid, powder, oil, solid and semisolid extracts (or any other forms of extracts) to the resin. It can be important that the extracts are clearly identified for active ingredients and their levels of actives. This can be done separately through any conventionally recognized process described in USP or any other pharmacopeia monographs or technical literature. Such extracts may be received either through simple extraction of liquids, oils, or resins of the herb, or in rare cases synthesis, or through any recognized process such as infusion, decoctions, maceration, digestion, expression, percolation, enfleurage, oil expression, steam distillation, solvent extraction, fractional distillation, phytonic extraction, synthesis, microorganism and gas type of extractions. Minerals also obtained through any conventional and described in USP or any other process or pharmacopeia or technical process may be added. The material may be filtered from 2 to 50 times in order to remove all of the impurities. In some embodiments, lot separation is maintained once filtered.

In some embodiments, the temperature is kept under 39 degrees Celsius during storage. In some embodiments, the temperature is kept under 39 degrees Celsius during the steps of transport, lab testing, liquifying, agitating, and filtering. Further details regarding the collecting, transporting, lab testing, and processing are described in U.S. Pat. Nos. 10,967,004 and 10,130,656.

The moisture may be removed from the processed material lots (i.e., dissolved, filtered, and subjected to agitation, magnetic, sound and light frequencies) to a predetermined residual moisture level, in accordance with step 135. The solution can be churned or left idle during the process with or without the occasional churning. Material may be further processed through a high pressure homogenizer, a high speed mixer or alternative, or continuous milling process which results in high uniformity and minimal particulate size of 1-10 nm within the particulate within the resulting material. What matters is that a sufficient amount of shear force is applied for long enough period of time to create emulsification of normally immiscible materials. If separation or poor plasticity or solubility of resin and along with other ingredients is observed, one may repeat homogenization/emulsification passes 2 up to 100 times in order to reach desired effect. The vessel with the solution may be actively (by contact) or passively (leaving by a heat source) heated to allow the moisture to escape from the solutions and concentrate it to a solid or a semisolid. In order to speed up the removal of moisture one may introduce an air flow from any source and ensure that the moisture can escape from the filtrate into the air or a special space. Another method to remove the excess moisture is via a vacuum. The vessel with resin may be placed a vacuum chamber, the vessel may be heating, and the resin may be slowly churned or mechanically agitated, causing the moisture to escape leaving the resin. Moisture can be measured at any time with a basic moisture meter equipped with a moisture sensor methods that can be used are gravimetric, coulometric, microwave resonance, Karl Fischer, infrared, conductive. The final resin may have a moisture level of between 1 and 25 percent.

The remaining slurry-like or resinous material may be tested, in accordance with step 140, for presence of all major and minor cannabinoids, terpenes, terpenoids, fatty acids, essential oils, and/or content of glycine. Lots that fail a testing formula (e.g., do not have glycine and at least one of a cannabinoid; do not have all major+at least 1 minor cannabinoid and glycine) may be discarded. Lots that pass the test and are similar in the qualitative and quantitative content of one or more of major and minor cannabinoids, terpenes, and terpenoids can be combined in order to create a master lot. For example, lots that have all major+at least 1 minor cannabinoid, glycine, and are over 90% similar in the amount and identity of tested ingredients may be combined through mixing to achieve uniformity. As another example, lots that have at least 1%, at least 2%, at least 5% glycine and are over 90% similar in the amount and identity of cannabinoids, terpenes and/or terpenoids may be combined through mixing to achieve uniformity.

The master lots may then be placed in cold/hot storage, in accordance with step 145. In some aspects, the master lots may be placed in cold/hot storage for a period of 10 to 365 days, or even longer, where the temperature can be changed from −40 Celsius to +39 degrees Celsius. In some embodiments, the master lots are placed in cold/hot storage where the temperature will be changed periodically (e.g., at least daily, at least every other day, at least once a week) from at least −20 degrees Celsius to at least 20 degrees Celsius. In some methods, the temperature is changed periodically from at least −35 degrees Celsius to at least 35 degrees Celsius, or from about −40 Celsius to about 39 Celsius. As used herein, the terms "about" and "approximately" mean within +10%. For example, about 10 degrees Celsius means between 9-11 degrees Celsius. The material may be observed to ensure that no separation of material takes place, specifically separation of solids and oils, or liquid parts and oils, solids and water. Lots where no separation (or no separation visible to the naked eye) is observed may be (optionally tested and) packaged, while lots where separation is observed may be discarded or set aside.

Contemplated methods can comprise a step of fingerprinting lots, as set forth in step 150. In some embodiments, each lot is profiled for identity and potency through comprehensive testing for glycine and at least one additional ingredient and/or type of ingredient (e.g., cannabinoids). For example, a lot can be tested for the presence and/or amount of one or more of glycine, cannabinoids, fatty acids, essential oils, terpenes, and/or terpenoids. For example, a lot can be tested for the presence and/or amount of one or more of glycine and cannabinoids. For example, a lot can be tested for the presence and amount of glycine, and the presence and amount of one or more types of cannabinoids (e.g., CBD content). For example, a lot can be tested for the presence and/or amount of one or more of glycine, cannabinoids, and fatty acids. For example, a lot can be tested for the presence and/or amount of one or more of glycine, cannabinoids, terpenes, and terpenoids. For example, a lot can be tested for the presence and/or amount of one or more of glycine, cannabinoids, fatty acids, terpenes, and terpenoids. This "fingerprint" of each lot can be documented for further calculations or use.

Contemplated methods can comprise a step of combining lots, as set forth in step 155. In some embodiments, lots may be combined to achieve desired characteristics of glycine and at least one other ingredient (e.g., CBD) and/or type of ingredient (e.g., cannabinoids).

The resulting processed resin can be a high quality and pure mineral pitch, with enriching ingredients and very low levels of undesired impurities. It should be appreciated that desirable cannabinoids, fatty acids, terpenes, terpenoids, essential oils, extracts, minerals, etc. are not considered undesired impurities. This level of undesirable contaminants can be lower than majority of traditionally manufactured shilajit, mumie or any form of mineral pitch. The processed resin can also have a higher efficacy due to higher bioavailability due to very small size of the resin forming particles and high homogeneity of the resin with other ingredients. The resin may be tested for the levels of residual or absence of the contaminant levels, microbiological safety, moisture levels by mass ashes not soluble in 10% HCl acid, ashless humic acids and glycine. It can be tested by using USP testing procedures or other Pharmacopeia method.

Resulting resin from a properly conducted manufacturing process may have indicator equal or better than the following:

For Lead: 3 mg/kg
For Arsenic: 6 mg/kg
For Cadmium: 0.5 mg/kg
For mercury: 1 mg/kg
For microbiological pathogens: less than 10 GFU/g
Moisture Levels by mass: 0.001 up to 60%
Ashes not soluble in 10 HCl: not exceeding 1.6%
Ashless humic acids: no less than 5%
Glycine: no less than 1%

In some embodiments, the resulting resin can additionally comprise at least 1 fatty acid and at least 1 terpene and/or terpenoid.

In some embodiments, the resulting resin can additionally comprise 3 or more major cannabinoids, and at least 1 minor cannabinoid.

The resulting resin can be left as semisolid, or converted into liquid, solid or powder, in accordance with step 160, via at least one of adding moisture to, removing moisture from, and pulverizing the material. The resulting novel resin products can include numerous cannabinoids, fatty acids, terpenes, terpenoids, essential oils, and glycine.

In some aspects, the methods described herein as Example 1 can increase the natural cannabinoid content in mineral pitch resin, but can require excessive effort in the collection and identification of raw material. This limitation can be overcome by planting and proliferating desired plants in the proximity of shilajit bearing stone collection. One advantage of the methods of Example 1 is that the source of cannabinoids in the mineral pitch resin product manufactured can be highly bioavailable with the presence of naturally produced cannabinoid metabolites (unlike cannabinoid extracts with lower bioavailability).

The mineral pitch resin product, which can be a semisolid, liquid, solid or powder, can be repackaged, in accordance with step 165, for transportation and/or distribution. For transportation the resin may be packaged in containers that are completely opaque to light. In such state with no penetration of light the resin is in a "dormant" state and will indefinitely store and can be transported for an indefinitely long time. (wholesale packaging first phase)

A second exemplary (but non-limiting) method of packaging may be in the biophotonic glass. Biophotonics improves the properties of nutritives and will substantially improve the quality of the resin. Such glass with allow the permeation of the spectrum of light within the wavelength of about 315 to 450 nm, and frequency of the 668-789 THz, it also blocks the light in the spectrum of about 450 to 620 nm, and allows the light through in the range of about 620 to 750 nm. At this point the resin can be stored indefinitely and can be shelf/storage stable over indefinite period of time.

Example Method 2

Figure 2:
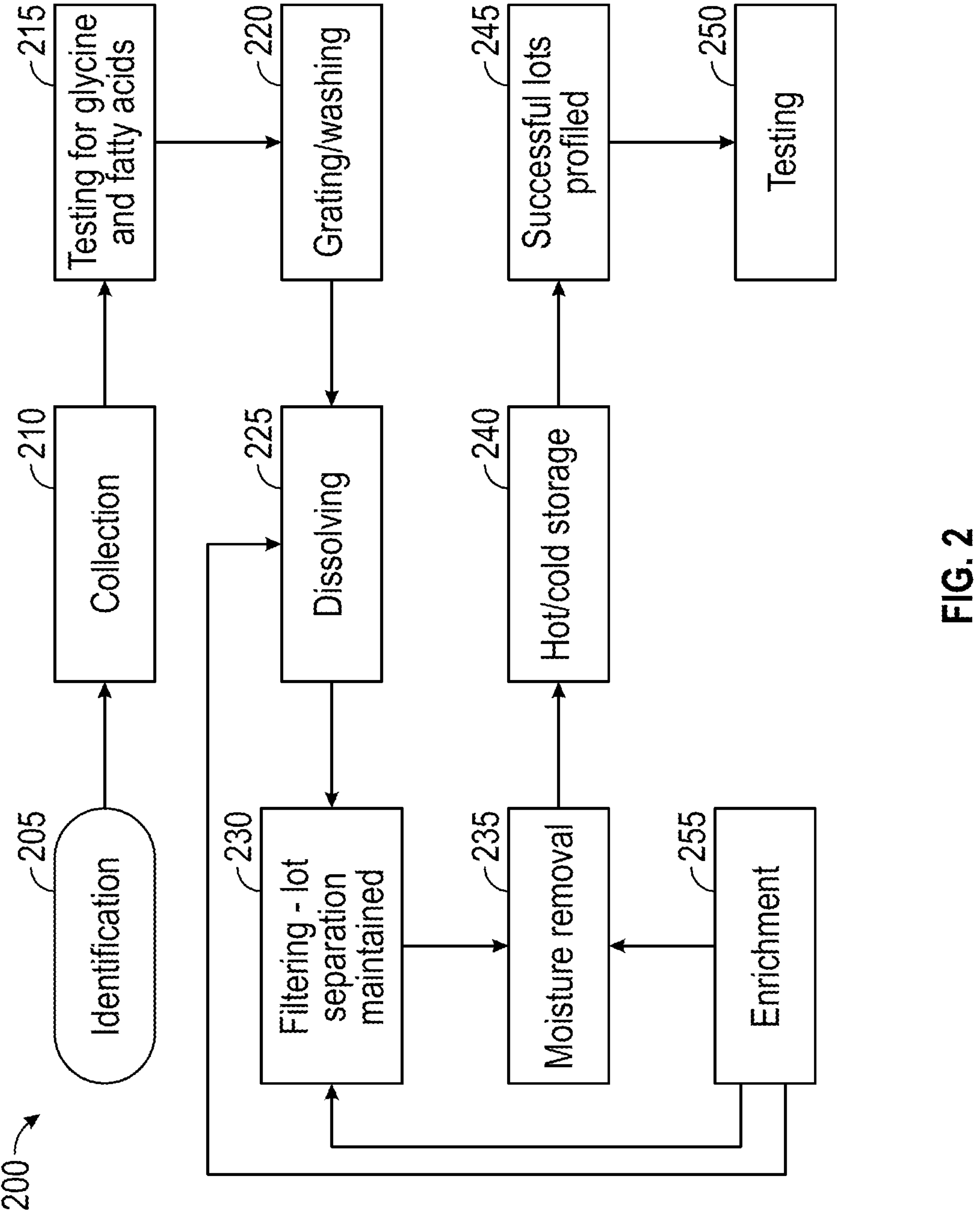
FIG. 2 is a flow diagram which shows steps and constituents in an exemplary method of creating mineral pitch resin combined with cannabinoids in form of oil optionally mixed with fatty acids, terpenes and/or terpenoids of fragrant essential oils, wherein the method demonstrates how to avoid separation of oils and resin.

A flow chart of another exemplary method 200 of the disclosure is set forth in FIG. 2. The steps of method 200 may include some or all of the steps of Example 1 methods, and cannabinoids, fatty acids, essential oils, terpenes, and/or terpenoids from any suitable source may be added during the production of mineral pitch resin products. Two of the challenges that are addressed with the methods of Example 2 stem from low bioavailability of certain forms of cannabinoids and oil soluble substances (e.g., oils) and the immiscibility of shilajit, which is a water-soluble substance, and various forms of cannabinoids, which often are oil-based substances.

A primary objective of the second embodiment is to create a stable mineral pitch resin, with homogeneous distribution of cannabinoids (and/or any oils and/or other ingredients) within the shilajit resin. The objective is reached by isolating raw material with high levels of saponin compounds and introducing of cannabinoids or any additional oils or oil soluble compounds into the resin at rates and pressure, torque or force, speeds that allow for emulsion formation without adding external emulsifiers. As described in Example method 1, high shear force, sufficient shear force application and number of passes will produce the desired outcome.

Methods of Example 2 generally start with the step of identifying shilajit bearing rock, in accordance with step 205. The preference for raw material collection may be given to areas with the highest amount of flora diversity in order to collect the highest number of diverse samples possible.

The material may be collected, in accordance with step 210. For example, the material may be collected in separate containers and all lots may be kept separated. A lot can be considered to be weight of material anywhere from 50 g to 500 kg. All collected lots can be marked with the exact GPS locations and precisely documented, for example, to identify locations that produce resin with desired emulsifier properties. The lots can be kept separate and mixing can be avoided.

According to step 215, each lot can be tested for the presence of glycine and fatty acids in order to verify authenticity and quality of the raw material of each lot. Once the identity of the material has been confirmed, the material can be processed into mineral pitch resin containing enhancing ingredients.

Detailed methods of how to manufacture mineral pitch of high quality is described in U.S. Pat. Nos. 10,967,004 and 10,130,656. One difference with the methods of Example 2 is that enhancing ingredients (e.g., cannabinoids in their various forms and oils) are introduced into the resin with varying amount of quantity and force.

The raw material can be slightly grated and washed off, for example, in food or pharmaceutical grade alcohol, in accordance with step 220. Separation of the lots can be maintained before, during and after step 220.

The raw material may be dissolved in water not exceeding 39 degrees Celsius, according to step 225. Dissolution of material may be expedited by agitating it at various RPMs ranging from 0.1 up to 25,000 RPMs. Prior to this point, at this point, or any time after this point, enriching ingredients (e.g., essential oils, cannabinoids, terpenes, terpenoids, fatty acids and/or various oils comprising of saturated, monounsaturated and polyunsaturated fatty acids) in any form can be added at any stage up to the stage of separation testing or even packaging, in accordance with step 255. The force applied to create the predetermined shear can range from 0.1 up to 100000 newtons, all depending on the amount and stage in which the raw material or resin is in.

The liquified material can be filtered through various filters under pressure, in accordance with step 230. Dissolution and filtration may be repeated several times (e.g., up to 50 times) with different amounts of water solvent, agitation, filtration or pressure. Lot separation can be maintained throughout step 230. Enrichment ingredients (e.g., Cannabinoids, terpenes, terpenoids, oils, and/or fatty acids in any form) can be added at any stage up to the stage of separation testing or even packaging, in accordance with step 255.

Once we obtained the final filtrate material, it may be an optimal time to introduce cannabinoids and oils into the filtrate lots. The number of lots at this point may count from a few up to several thousands and is dictated by economic and manufacturing feasibility. Cannabinoids and oils comprising fatty acids, terpenes and terpenoids in any form can be introduced into the filtrate. For example, cannabinoids in the form of oil, powder, solid, or semisolid can be added at any stage, at rates from 0.001 ml per second into the solution or resin. Other oils made of saturated monounsaturated and poly unsaturated fatty acids, terpenes and/or terpenoids may be introduced to improve resulting fragrance or properties of shilajit. The temperature can be maintained. A high RPM mixer or high pressure homogenizer as an alternative process can be used to emulsify or bond the shilajit material with cannabinoids and/or other enhancing ingredients. In some aspects cannabinoids and/or oils can be introduced at a rate starting from 0.1 mL per minute or reasonably higher multiplied by the factors of 2, whichever is reasonably appropriate for emulsification of the filtrate and cannabinoids and oils added to the filtrate. During the cannabinoids and oils introduction process turbulence, high shear and cavitation forces may be applied to the mixture at the rates of up to 25,000 RPMs or higher and 6000 bars or higher. The predetermined force of shear can range from 0.1 to 100000 newtons. The mixture may be maintained through chilling under a temperature lower than 39 degrees Celsius.

Moisture may be removed from the mixture down to a predetermined level, in accordance with step 235, resulting in filtered lots of predetermined residual moisture levels. In some embodiments, step 235 can result in various lots of liquid, semisolid, or solid material which can be pulverized. The material may then go to stability testing cold/hot storage, in accordance with step 240. The resulting lots can tested in a cold\hot storage for the period of 10 to 365 days, for example, as described in Example method 1. In some embodiments, hot/cold storage testing is done under conditions where temperature can be changed numerous times within 24-hour periods from hot and cold temperatures (e.g., from −40 Celsius to +39 Celsius). If excessive separation of oils is observed in any lot (or in some embodiment, if any separation of oil is observed in any lot with the naked eye), such lot may be discarded. If there is no visible separation (or no excessive visible separation) observed, this can be an indicator that a successful and stable emulsification and bonding took place and the resin now contains predetermined amounts of cannabinoids, terpenes, terpenoids, essential oils, and/or fatty acids.

GPS and proximity data of the successful lots can be profiled, in accordance with step 245, as locations of successful lots can signal unique emulsification properties of the raw material which resulted in homogenous resin as a liquid, solid or a semisolid.

The lots where no separation (or no excessive separation) was observed may be tested, in accordance with step 250, for the presence of glycine, and/or at least one of cannabinoids, terpenes, terpenoids and/or fatty acids from Tables 1-4.

The shilajit resin with cannabinoids terpenes, terpenoids, essential oils, and/or fatty acids that meet expectations may be packaged.

Example Method 3

Figure 3:
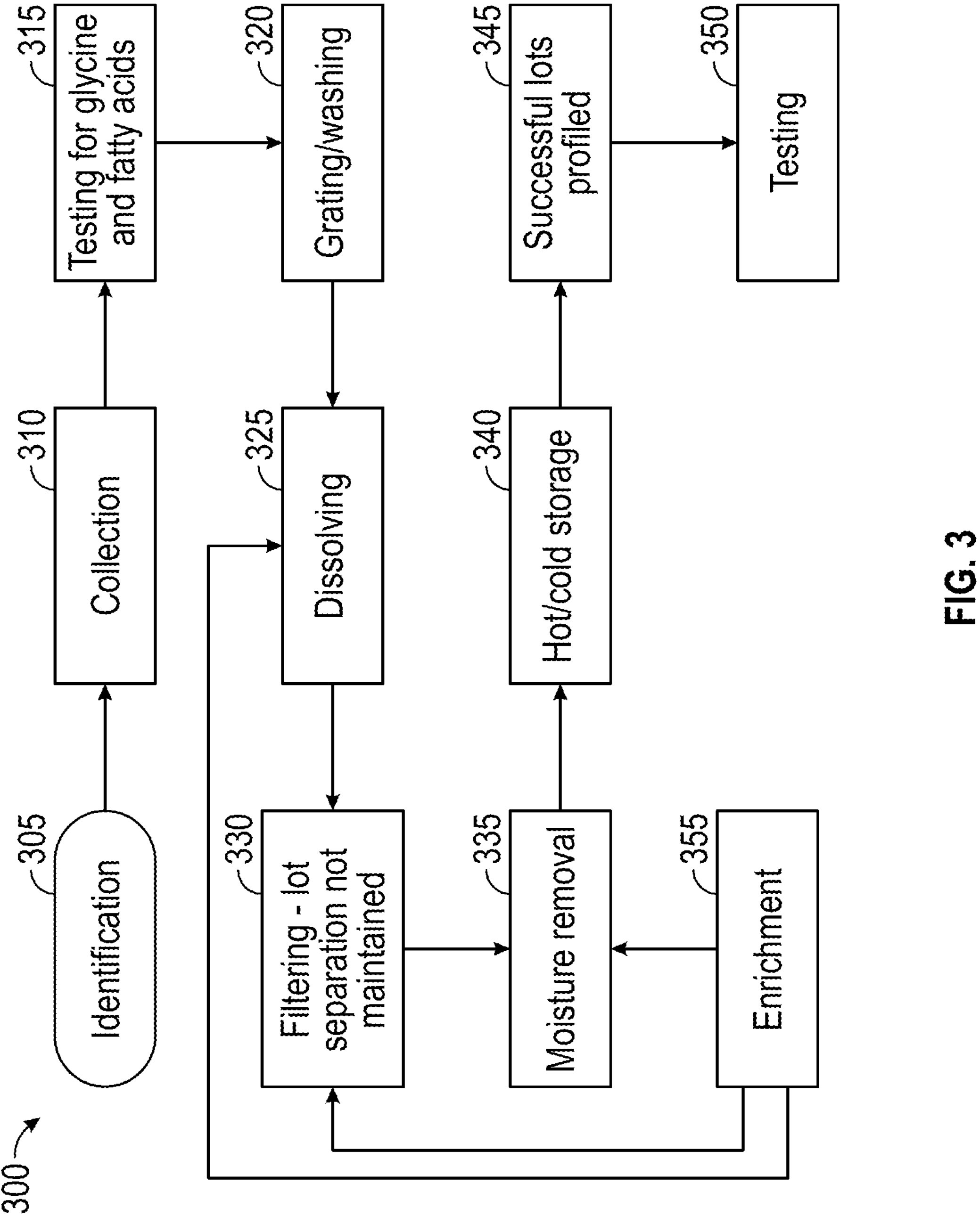
FIG. 3 is a flow diagram which shows steps and constituents in an exemplary method of creating mineral pitch resin combined with at least one of cannabinoids, terpenes, terpenoids, and fatty acids, for example, of fragrant essential oils, in the form of a liquid emulsion or dehydrated emulsion in the form of powder.

A flow chart of another exemplary method 300 of the disclosure is set forth in FIG. 3. The steps of method 300 may include some or all of the steps of Example methods 1 and 2, with a step of introducing terpenes, terpenoids, essential oils, and fatty acids into mineral pitch as an emulsion prepared separately and introduced at any stage of production, which may be necessary for production efficacy purposes. Not all resulting resins in the embodiment one and two will result in a desired profile of cannabinoids, terpenes, terpenoids, essential oils, and fatty acids, or will be absent of separation due to immiscible nature of shilajit resin and cannabinoids/fatty acids. Moreover, it is contemplated that steps of Example 3 may be beneficial when production has limiting factors due to absence of equipment, necessary energy or a time factor.

There are numerous ways to produce an emulsion of cannabinoids, terpenes, terpenoids, essential oils, fatty acids and water. This emulsion can be introduced at any stage of manufacturing as long as it is well agitated into the resin. The need for the emulsion is caused by absence saponins and polysaccharides in the resins, which may prevent the resin and cannabinoids/fatty acids to create a homogenous non-separating resin. In some aspects, a predetermined form of an emulsion, with a predetermined laser diffraction, dynamic light scattering and zeta potential, viscosity, phase equilibria, droplet size, stability, pH, etc., can be added at any stage of preparing the resin. The emulsion can be added in a liquid form, or with predetermined levels of moisture removed in form of a semisolid, solid or powder in order to create a homogenous mixture of the shilajit resin and the cannabinoids, fatty acids and/or other ingredients.

Optimal stages to introduce the emulsion into the resin include: When the liquefied material was dissolved in water; when the material was already filtered and is ready for dehumidification; or while the moisture is being removed from the filtrate. At any of the stages the combination of the resin and the emulsion may be agitated within the parameters described in Example 2. The temperature may be maintained under 39 degrees Celsius at all times.

Once the dehumidifier resin passed the hot/cold storage test as described in the Example 2, the resin may be tested for the presence of glycine, cannabinoids, terpenes, terpenoids, essential oils, and/or fatty acids. All as described in Examples 1 and 2. In some aspects, the resin can be considered ready for packaging if tests show the presence and identity of no less than three cannabinoids, terpenes, terpenoids, and/or essential oils, plus fatty acids and/or glycine.

Methods of Example 3 generally start with the step of identifying shilajit bearing rock, in accordance with step 305. The preference for raw material collection may be given to areas with the highest amount of flora diversity in order to collect the highest number of diverse samples possible.

The material may be collected, in accordance with step 310. For example, the material may be collected in separate containers and all lots may be kept separated. A lot can be considered to be weight of material anywhere from 50 g to 500 kg. All collected lots can be marked with the exact GPS locations and precisely documented, for example, to identify locations that produce resin with desired emulsifier properties. The lots can be kept separate and mixing can be avoided.

According to step 315, each lot can be tested for the presence of glycine and fatty acids in order to verify authenticity and quality of the raw material of each lot. Once the identity of the material has been confirmed, the material can be processed into mineral pitch resin containing enhancing ingredients.

Detailed methods of how to manufacture mineral pitch of high quality is described in U.S. Pat. Nos. 10,967,004 and 10,130,656. One difference with the methods of Example 3 is that enhancing ingredients (e.g., cannabinoids in their various forms and oils) are introduced into the resin with varying amount of quantity and force.

The raw material can be slightly grated and washed off, for example, in food or pharmaceutical grade alcohol, in accordance with step 320. Separation of the lots can be maintained before, during and after step 220.

The raw material may be dissolved in water not exceeding 39 degrees Celsius, according to step 325. Dissolution of material may be expedited by agitating it at various RPMs ranging from 0.1 up to 25,000 RPMs. Prior to this point, at this point, or any time after this point, enriching ingredients (e.g., essential oils, cannabinoids, terpenes, terpenoids, fatty acids and/or various oils comprising of saturated, monounsaturated and polyunsaturated fatty acids) in the form of an emulsion/dispersion can be added at any stage up to the stage of separation testing or even packaging, in accordance with step 355. The force applied to create the predetermined shear can range from 0.1 up to 100000 newtons, all depending on the amount and stage in which the raw material or resin is in.

The liquified material can be filtered through various filters under pressure, in accordance with step 330. Dissolution and filtration may be repeated several times (e.g., up to 50 times) with different amounts of water solvent, agitation, filtration or pressure. In some embodiments, lot separation does not need to be maintained throughout step 325 and/or 330. Enrichment ingredients (e.g., Cannabinoids, terpenes, terpenoids, oils, and/or fatty acids in any form) can be added at this stage, in accordance with step 355.

According to step 355, cannabinoids and oils comprising fatty acids, terpenes and terpenoids in the form of an emulsion/dispersion can be introduced into the filtrate. For example, cannabinoids in the form of an emulsion/dispersion can be added at any stage, at rates from 0.001 ml per second into the solution or resin. Other oils made of saturated monounsaturated and poly unsaturated fatty acids, terpenes and/or terpenoids may be introduced to improve resulting fragrance or properties of shilajit. The temperature can be maintained. A high RPM mixer or high pressure homogenizer as an alternative process can be used to emulsify or bond the shilajit material with cannabinoids and/or other enhancing ingredients. In some aspects cannabinoids and/or oils can be introduced at a rate starting from 0.1 mL per minute or reasonably higher multiplied by the factors of 2, whichever is reasonably appropriate for emulsification of the filtrate and cannabinoids and oils added to the filtrate. During the cannabinoids and oils introduction process turbulence, high shear and cavitation forces may be applied to the mixture at the rates of up to 25,000 RPMs or higher and 6000 bars or higher. The predetermined force of shear can range from 0.1 to 100000 newtons. The mixture may be maintained through chilling under a temperature lower than 39 degrees Celsius.

Moisture may be removed from the mixture down to a predetermined level, in accordance with step 335, resulting in filtered lots of predetermined residual moisture levels. In some embodiments, step 335 can result in various lots of liquid, semisolid, or solid material which can be pulverized. The material may then go to stability testing cold/hot storage, in accordance with step 340. The resulting lots can tested in a cold\hot storage for the period of 10 to 365 days, for example, as described in Example method 1. In some embodiments, hot/cold storage testing is done under conditions where temperature can be changed numerous times within 24-hour periods from hot and cold temperatures (e.g., from −40 Celsius to +39 Celsius). If excessive separation of oils is observed in any lot (or in some embodiment, if any separation of oil is observed in any lot with the naked eye), such lot may be discarded. If there is no visible separation (or no excessive visible separation) observed, this can be an indicator that a successful and stable emulsification and bonding took place and the resin now contains predetermined amounts of cannabinoids, terpenes, terpenoids, essential oils, and/or fatty acids.

GPS and proximity data of the successful lots can be profiled, in accordance with step 345, as locations of successful lots can signal unique emulsification properties of the raw material which resulted in homogenous resin as a liquid, solid or a semisolid.

The lots where no separation (or no excessive separation) was observed may be tested, in accordance with step 350, for the presence of glycine, and/or at least one of cannabinoids, terpenes, terpenoids and/or fatty acids from Tables 1-4.

The shilajit resin with cannabinoids terpenes, terpenoids, essential oils, and/or fatty acids that meet expectations may be packaged.

In some aspects of the Example methods 1-3 described herein, shilajit is maintained at or under 39 degrees Celsius throughout the process. The number of homogenization and emulsification passes depends on, for example, testing the physical properties of the resin. It may not be possible to establish separation immediately in the production, as the material must be tested later in the cold/hot storage. Nevertheless, some immediate indicators can be observed. For example, after stopping a churning or emulsification process within the temperature range of 35 to 39 degrees Celsius, the surface of the resin mass should be very smooth and have a shine, there should be no bubbles, the surface should be glossy and reflective to light. Another way to immediately gauge the quality of the resin is to spread it out around the area, for example, an area of approximately 12 by 12 inches and let it settle to a level. In good light, the material will be reflective to the point where one would be able to use it as a primitive mirror. If looking into it, one would not necessary see details of their face, but a silhouette of a face can be obviously visible. Another way to assess the quality of the resin comprises using a grindometer, wherein material properly homogenized and having required properties will be within 8 to 5 on the Hegman scale.

Applicant surprisingly discovered that the shilajit products manufactured according to the methods herein can stay emulsified on the shelves with no visible separation of oil and resin taking place. In some aspects, the shilajit product is a ready-to consume product that has no visible separation of oil and resin for at least 1 month, at least 2 months, at least 3 months, at least 4 months, at least 5 months, at least 6 months, at least 9 months, at least 1 year, at least 2 years, at least 3 years or even longer when stored at 25 degrees Celsius. In some aspects, the shilajit product is a ready-to consume product that has no visible separation of oil and resin for at least 1 month, at least 2 months, at least 3 months, at least 4 months, at least 5 months, at least 6 months, at least 9 months, at least 1 year, at least 2 years, at least 3 years or even longer when stored under normal storage conditions. In some aspects, the shilajit product is a ready to consume product that is within 8 to 5 on the Hegman scale when stored at 25 degrees Celsius for at least 1 month, at least 2 months, at least 3 months, at least 4 months, at least 5 months, at least 6 months, at least 9 months, at least 1 year, at least 2 years, at least 3 years or even longer. In some aspects, the shilajit product is a ready to consume product that is within 8 to 5 on the Hegman scale when stored under normal storage conditions for a shilajit resin product for at least 1 month, at least 2 months, at least 3 months, at least 4 months, at least 5 months, at least 6 months, at least 9 months, at least 1 year, at least 2 years, at least 3 years or even longer.

Example Compositions

While some exemplary compositions are provided herein, it should be appreciated that shilajit products of the disclosure can comprise shilajit and any combination of essential oils, fatty acids, terpenes, terpenoids, and/or cannabinoids in any suitable amounts. Further, ingredients from the different example compositions can be interchanged (e.g., replace one or more ingredients with one or more ingredients from another example composition), one or more ingredients from the example compositions can be removed, one or more ingredients can be added (e.g., an ingredient from another example composition and/or from Tables 1-4 can be added to the formulation), and/or adjusted (e.g., increase or decrease amount and/or concentration of one or more ingredients in the composition).

In some preferred embodiments, all of the ingredients in the shilajit product are natural. Additionally or alternatively, in some preferred embodiments, all of the ingredients in the shilajit product are full spectrum. Additionally or alternatively, in some preferred embodiments, all of the ingredients in the shilajit product are minimally processed. Additionally or alternatively, in some preferred embodiments, all of the ingredients in the shilajit product are non-synthetic.

It should be appreciated that in some contemplated embodiments, a shilajit product can comprise non-natural ingredient(s), ingredient(s) that are not full spectrum, ingredient(s) that are not minimally processed, and/or ingredient(s) that are synthetic.

In some aspects, each individual ingredient in a shilajit composition of the disclosure (including the Example Compositions provided herein) can be present in any suitable amount or concentration. For example, in some embodiments, each individual ingredient in a shilajit composition that is an enhancing ingredient and/or non-shilajit can be present in an amount that is between 0.0000001% and 10%, between 0.0000001% and 15%, between 0.0000001% and 20%, between 0.0000001% and 25%, or between 0.0000001% and 30% of the amount of shilajit in the composition, for example, by weight. In some aspects, shilajit can be present in any suitable amount in the shilajit composition, including for example, between 0.0000001% and 99% of the composition, between 0.1% and 99% of the composition, between 1% and 98% of the composition, between 1% and 95% of the composition, between 1% and 90% of the composition, between 10% and 85% of the composition, between 10% and 80% of the composition, between 20% and 75% of the composition, between 25% and 50% of the composition, between 25% and 99.9% of the composition, between 25% and 98% of the composition, between 50% and 95% of the composition, or between 75% and 90% of the composition, by weight. As enrichment of shilajit resin with one or more quality essential oils, fatty acids, terpenes, terpenoids and/or cannabinoids is expensive, some preferred compositions can maintain the amount of all enrichment ingredients (fatty acids, essential oils, terpenes, terpenoids, cannabinoids) to under 10 wt % of the composition. However, compositions comprising any suitable amounts of each of the enrichment ingredients are contemplated herein. For example, in some contemplated compositions (including the Example Compositions provided herein), the total amount of all enrichment ingredients (fatty acids, essential (or other desired) oils, terpenes, terpenoids, cannabinoids) is between 0.1-30 wt %, between 1-20 wt %, between 0.1-10 wt %, or between 0.1-15 wt % of the composition. In some contemplated compositions (including the Example Compositions provided herein), the total amount of all fatty acids present in the composition comprise between 0.1-30 wt %, between 1-20 wt %, between 0.1-10 wt %, or between 0.1-15 wt % of the composition. In some compositions (including the Example Compositions provided herein), the total amount of all fatty acids present in the composition comprise 0.000001-10 wt %, between 0.000001-7 wt %, between 0.000001-5 wt %, between 0.000001-2 wt %, between 0.000001-1 wt %, or between 0.000001-0.5 wt % of the composition. In some compositions (including the Example Compositions provided herein), each fatty acid (e.g., 1, 2, 3, 4, 5, between 1-100, between 1-50, between 1-25, between 1-15) present in the composition comprises 0.000001-10 wt %, between 0.000001-7 wt %, between 0.000001-5 wt %, between 0.000001-2 wt %, between 0.000001-1 wt %, or between 0.000001-0.5 wt % of the composition. In some contemplated compositions (including the Example Compositions provided herein), the total amount of all terpenes and/or terpenoids present in the composition comprise between 0.1-30 wt %, between 1-20 wt %, between 0.1-10 wt %, or between 0.1-15 wt % of the composition. In some compositions (including the Example Compositions provided herein), the total amount of all terpenes and/or terpenoids present in the composition comprise 0.000001-10 wt %, between 0.000001-7 wt %, between 0.000001-5 wt %, between 0.000001-2 wt %, between 0.000001-1 wt %, or between 0.000001-0.5 wt % of the composition. In some compositions (including the Example Compositions provided herein), each terpene (e.g., 1, 2, 3, 4, 5, between 1-100, between 1-50, between 1-25, between 1-15) present in the composition comprises 0.000001-10 wt %, between 0.000001-7 wt %, between 0.000001-5 wt %, between 0.000001-2 wt %, between 0.000001-1 wt %, or between 0.000001-0.5 wt % of the composition. In some compositions (including the Example Compositions provided herein), each terpenoid (e.g., 1, 2, 3, 4, 5, between 1-100, between 1-50, between 1-25, between 1-15) present in the composition comprises 0.000001-10 wt %, between 0.000001-7 wt %, between 0.000001-5 wt %, between 0.000001-2 wt %, between 0.000001-1 wt %, or between 0.000001-0.5 wt % of the composition. In some contemplated compositions (including the Example Compositions provided herein), the total amount of all essential oils present in the composition comprise between 0.1-30 wt %, between 1-20 wt %, between 0.1-10 wt %, or between 0.1-15 wt % of the composition. In some compositions (including the Example Compositions provided herein), the total amount of all essential oils present in the composition comprise 0.000001-10 wt %, between 0.000001-7 wt %, between 0.000001-5 wt %, between 0.000001-2 wt %, between 0.000001-1 wt %, or between 0.000001-0.5 wt % of the composition. In some compositions (including the Example Compositions provided herein), each essential oil (e.g., 1, 2, 3, 4, 5, between 1-100, between 1-50, between 1-25, between 1-15) present in the composition comprises 0.000001-10 wt %, between 0.000001-7 wt %, between 0.000001-5 wt %, between 0.000001-2 wt %, between 0.000001-1 wt %, or between 0.000001-0.5 wt % of the composition. In some contemplated compositions (including the Example Compositions provided herein), the total amount of all cannabinoids present in the composition comprise between 0.1-30 wt %, between 1-20 wt %, between 0.1-10 wt %, or between 0.1-15 wt % of the composition. In some compositions (including the Example Compositions provided herein), the total amount of all cannabinoids present in the composition comprise 0.000001-10 wt %, between 0.000001-7 wt %, between 0.000001-5 wt %, between 0.000001-2 wt %, between 0.000001-1 wt %, or between 0.000001-0.5 wt % of the composition. In some compositions (including the Example Compositions provided herein), each cannabinoid (e.g., 1, 2, 3, 4, 5, between 1-100, between 1-50, between 1-25, between 1-15) present in the composition comprises 0.000001-10 wt %, between 0.000001-7 wt %, between 0.000001-5 wt %, between 0.000001-2 wt %, between 0.000001-1 wt %, or between 0.000001-0.5 wt % of the composition.

It should be appreciated that shilajit resin can refer to, for example, shilajit resin according to the methods and products described herein (e.g., without addition of enrichment ingredients) and/or in international patent application PCT/US2017/019517, U.S. Pat. No. 10,967,004, or U.S. Pat. No. 10,130,656.

Example Composition A

Example Composition A comprises shilajit resin and the enrichment ingredients set forth in Table 5.

TABLE 5

| Ingredient | Type essential oils, fatty acids, terpenes/ terpenoids, cannabinoids |
|---|---|
| Adrenic acid (AdA) | Fatty acid |
| Agarwood | Essential oil |
| Alpha-linolenic acid (ALA) | Fatty acid |

TABLE 5-continued

| Ingredient | Type essential oils, fatty acids, terpenes/ terpenoids, cannabinoids |
|---|---|
| Amyris | Essential oil |
| Arachidic acid | Fatty acid |
| Behenic acid | Fatty acid |
| Bergamot | Essential oil |
| Bosseopentaenoic acid | Fatty acid |
| Butyric acid | Fatty acid |
| Cajeput | Essential oil |
| Capric acid | Fatty acid |
| Caproic acid | Fatty acid |
| Caprylic acid | Fatty acid |
| Carboceric acid | Fatty acid |
| Catalpic acid | Fatty acid |
| Ceroplastic acid | Fatty acid |
| Cerotic acid | Fatty acid |
| Cervonic acid | Fatty acid |
| Cervonic acid | Fatty acid |
| cistus ladanifer sp. | Essential oil |
| Conjugated Linolenic Acids | Fatty acid |
| Crotonic acid | Fatty acid |
| Di-unsaturated fatty acid | Fatty acid |
| Dihomo-gamma-linolenic acid (DGLA) | Fatty acid |
| Dihomo-γ-linolenic acid | Fatty acid |
| Docosadienoic acid | Fatty acid |
| Docosahexaenoic acid (DHA, Cervonicacid) | Fatty acid |
| Docosapentaenoic acid (DPA, Clupanodonic acid) | Fatty acid |
| Docosatetraenoic acid | Fatty acid |
| Eicosadienoic acid | Fatty acid |
| Eicosapentaenoic acid (EPA, Timnodonic acid) | Fatty acid |
| Eicosatetraenoic acid (ETA) | Fatty acid |
| Eicosenoic acid | Fatty acid |
| Elaidic acid | Fatty acid |
| Eleostearic acid | Fatty acid |
| fir balsam | Essential oil |
| leleshwa | Essential oil |
| petitgrain bigarade | Essential oil |
| pink pepper | Essential oil |
| ravintsara organic | Essential oil |
| sandalwood | Essential oil |
| spearmint organic | Essential oil |
| tangerine | Essential oil |
| tonka bean butter | Essential oil |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition A features numerous benefits to human health from the high-quality shilajit resin, cannabinoids, fatty acids, essential oils, terpenes, terpenoids, and/or essential fatty acids present therein. It is contemplated that certain combinations of the ingredients of Composition A can elicit synergistic effects on one or more of the benefits of such ingredients. Composition A can have, among others, one, some or all of the following benefits: healthier digestive system, spasm relief, pain relief, decreased risk of heart disease, healthier heart function, skin regeneration or improvement, slowing aging, alleviating anxiety, normalization of blood pressure, decrease blood lipids, support blood clotting factors, help provide a protective barrier against the environment in order to maintain good skin quality, improve skin hydration, soothe skin, regenerate skin, slow aging, alleviate anxiety, blood clotting support, blood vessel support, promote healthy inflammatory response, support digestive health, reduce inflammation, lower risk of diseases and promote overall health, antiseptic qualities, analgesic properties, treat skin wounds, treat inflammation, treat colds, strong antiviral and antimicrobial properties, antibacterial, antiviral, antifungal and anti-inflammatory properties (of saturated fatty acids), managing, preventing or treating yeast infections, skin conditions and digestive disorders, managing or reducing high cholesterol, disinfecting benefits, forms part in essential fatty acids needed to maintain a healthy heart, maintains cell membrane, and controls nutrient use and metabolism.

Example Composition B

Example Composition B can be an alternative to Example Composition A, and comprises shilajit resin and the enrichment ingredients set forth in Table 6.

TABLE 6

| Ingredients |
|---|
| Adrenic acid (AdA) |
| β-agarofuran, α-agarofuran, Nor-ketoagarofuran, Agarospirol, β-eudesmol, kusunol |
| Alpha-linolenic acid (ALA) |
| Valerianol, B-eudesmol, A-eudesmol, Elemol, Y-eudismol |
| Arachidic acid |
| Behenic acid |
| (R)-p-mentha-1,8-diene, citral, linalool, (R)-p-mentha-1,8-diene |
| Bosseopentaenoic acid |
| Butyric acid |
| 1.8 Cineole, limomene, alpha terpineol, Beta-Caryophyllene |
| Capric acid |
| Caproic acid |
| Caprylic acid |
| Carboceric acid |
| Catalpic acid |
| Ceroplastic acid |
| Cerotic acid |
| Cervonic acid |
| Cervonic acid |
| α-pinene, viridiflorol, borneol, trimethyl cyclohexanone, and camphene |
| Conjugated Linolenic Acids |
| Crotonic acid |
| Di-unsaturated fatty acid |
| Dihomo-gamma-linolenic acid (DGLA) |
| Dihomo-γ-linolenic acid |
| Docosadienoic acid |
| Docosahexaenoic acid (DHA, Cervonic acid) |
| Docosapentaenoic acid (DPA, Clupanodonic acid) |
| Docosatetraenoic acid |
| Eicosadienoic acid |
| Eicosapentaenoic acid (EPA, Timnodonic acid) |
| Eicosatetraenoic acid (ETA) |
| Eicosenoic acid |
| Elaidic acid |
| Eleostearic acid |
| β-pinene, Δ3-carene, bornyl acetate, α-terpineol, piperitone, thymol, caryophyllene, longifolene, β-bisabolene |
| Fenchol, 1,8-cineole, a-terpinol, a-pinene, trans-pinene hydrate, terpinen-4-ol, camphene |
| Linalyl acetate, Linalol, Citral, Geraniol, Limonene, Linalool |
| alpha-pinene, sabinene, beta-pinene, delta-3-carene, alpha-phellandrene, beta-phellandrene, and limonene |
| 1,8 cineole, Terpineol, pinenes |
| teresantol, β-Santalol, α-Cedrol, α-Santalol, α-Bergamotol, Nuciferol, cis-Lanceol, 5-Hydroxycalamenene, Camphene, α-Terpinene, α-Famesene, α-Santalene, α-Cedrene, α-Guaiene, β-Santalene, Germacrene B, α-Curcumene, Elixene, α-Bergamotene, Bicyclogermacrene, Acoradiene, γ-Elemene |
| Pinene, beta Pinene, Carvone, Cineole, Caryophyllene, Linalool, Limolene, Menthol, Myrcene |
| alpha-pinene, myrcene, d-limonene, linalool, terpineol, alpha-humulene, beta-caryophyllene, alpha-bisabolol, beta-pinene |
| Myrcene |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition B features numerous benefits to human health from the high-quality shilajit resin, cannabinoids, fatty acids, essential oils, terpenes, terpenoids, and/or essential fatty acids present therein. It is contemplated that certain combinations of the ingredients of Composition B can elicit synergistic effects on one or more of the benefits of such ingredients. Composition B can have, among others, one, some or all of the following benefits: healthier digestive system, spasm relief, pain relief, decreased risk of heart disease, healthier heart function, skin regeneration or improvement, slowing aging, alleviating anxiety, normalization of blood pressure, decrease blood lipids, support blood clotting factors, help provide a protective barrier against the environment in order to maintain good skin quality, improve skin hydration, soothe skin, regenerate skin, slow aging, alleviate anxiety, blood clotting support, blood vessel support, promote healthy inflammatory response, support digestive health, reduce inflammation, lower risk of diseases and promote overall health, antiseptic qualities, analgesic properties, treat skin wounds, treat inflammation, treat colds, strong antiviral and antimicrobial properties, antibacterial, antiviral, antifungal and anti-inflammatory properties (of saturated fatty acids), managing, preventing or treating yeast infections, skin conditions and digestive disorders, managing or reducing high cholesterol, disinfecting benefits, forms part in essential fatty acids needed to maintain a healthy heart, maintains cell membrane, and controls nutrient use and metabolism.

Example Composition C

Example Composition C comprises shilajit resin and the enrichment ingredients set forth in Table 7.

TABLE 7

| Ingredients |
|---|
| Ajwain |
| bay laurel |
| black pepper |
| Calamus |
| Corymbia calophylla |
| davana oil |
| Enanthic acid |
| Erucic acid |
| fragonia |
| Gadoleic acid |
| galanga |
| Gamma-linolenic acid (GLA) |
| Geddic acid |
| Glycine |
| Gondoic acid |
| Helichrysum |
| Heneicosapentaenoic acid (HPA) |
| Heneicosylic acid |
| Hentriacontylic acid |
| Heptatriacontylic acid |
| Hexa-unsaturated fatty acids |
| Hexadecatrienoic acid (HTA) |
| Hexatriacontylie acid |
| Indian basil |
| Jacaric acid |
| juniper berry |
| khella |
| Labdanum |
| Lacceroic acid |
| Lauric acid |

TABLE 7-continued

| Ingredients |
| --- |
| Lignoceric acid |
| Linoleic acid |
| Linolelaidic acid |
| Linolenic acid |
| mandarin orange-citrus |
| Margaric acid |
| Mead acid |
| Melissic acid |
| Mono-unsaturated fatty acid |
| Montanic acid |
| Myristic acid |
| Myristoleic |
| nagarmotha |
| Nervonic acid |
| Nonacosylic acid |
| Nonadecylic acid |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition C features numerous benefits to human health from the high-quality shilajit resin, cannabinoids, fatty acids, essential oils, terpenes, terpenoids, and/or essential fatty acids present therein. It is contemplated that certain combinations of the ingredients of Composition C can elicit synergistic effects on one or more of the benefits of such ingredients. Composition C can have, among others, one, some or all of the following benefits: antibacterial and antifungal properties, help lower blood pressure, relieve indigestion, ease indigestion and reduce flatulence, antiseptic and antibacterial properties for UTI, soothe sore throat, antioxidant levels support immunity, lower cholesterol, lower blood sugar levels, mild sedative, helps manage rheumatoid arthritis (e.g., easing symptom associated with rheumatoid arthritis, slow progression of rheumatoid arthritis), induces relaxation and sleep, helps with lung infections like bronchitis and tuberculosis, helps with UTI infections, calming effects lower stress and anxiety, antiviral, antimicrobial benefits for infections, relaxes breathing, improves wound healing, helps against common respiratory infections (e.g., prevents common respiratory infections, eases a symptom of common respiratory infections), help decrease stress, analgesic effects, rich source of antioxidants to support immunity, reduce pain and inflammation, helps improve fertility, antiviral, and antimicrobial properties help against infection, reduce systems of inflammation, promote wound healing, diuretic effects help manage arthritis (e.g., relieves pain from arthritis), help with gastrointestinal disorders (e.g., prevent, reduce symptom associated with gastrointestinal disorder), helps improve cardiovascular function with potent vasodilator effect, promote healthy cholesterol, protects against kidney stones, loosens chest congestion, prevents or reduces constipation, the drying agent helps stop bleeding from cuts, stimulates health growth, helps with indigestion, and helps manage obesity.

Example Composition D

Example Composition D can be an alternative to Example Composition C, and comprises shilajit resin and the enrichment ingredients set forth in Table 8.

TABLE 8

| Ingredients |
| --- |
| thymol, gammaterpene, orthocymene, heptaethylene, glycol, monododecyl ether, oleic acid, linoleic acid |
| eucalyptol, terpinyl acetate, sesquiterpenes, methyleugenol, alpha and beta pinenes, phellandrene, linalol, geraniol, terpineol, lauric acid |
| Pinene, caryophyllene |
| α-asarone, (E)-methylisoeugenol, methyleugenol, β-asarone, α-cedrene, camphor |
| davanone, linalool, dehydro-a-linalool, terpinen-4 oil, nordavanone (c11-terpenoid), devanafurans |
| alpha-pinene, beta-pinene, myrcene, 1,8-cineole, linalool, geraniol, terpinene4-ol, terpineol |
| 1,8-cineole, exo-2-hydroxy-1,8-cineole acetate, -caryophyllene, - and -pinenes, -bisabolene, chavicol, limonene, 4-terpineol, chavicol acetate, methyl eugenol |
| α-pinene, α-cedrene, aromadendrene, β-caryophyllenelimonene, limonene, neryl acetate, 2-methylcyclohexyl pentanoate, 2-methylcyclohexyl octanoate, geranyl acetate |
| limonene, camphor, beta-pinene, myrcene, sabinene |
| γ-pyrones, khellin, visnagin, visnaginone, ammiol, Khellinol, khellol, visammiol, khellinin, khellinone |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition D features numerous benefits to human health from the high-quality shilajit resin, cannabinoids, fatty acids, essential oils, terpenes, terpenoids, and/or essential fatty acids present therein. It is contemplated that certain combinations of the ingredients of Composition D can elicit synergistic effects on one or more of the benefits of such ingredients. Composition D can have, among others, one, some or all of the following benefits: antibacterial and antifungal properties, help lower blood pressure, relieve indigestion, ease indigestion and reduce flatulence, antiseptic and antibacterial properties for UTI, soothe sore throat, antioxidant levels support immunity, lower cholesterol, lower blood sugar levels, mild sedative, helps manage rheumatoid arthritis (e.g., easing symptom associated with rheumatoid arthritis, slow progression of rheumatoid arthritis), induces relaxation and sleep, helps with lung infections like bronchitis and tuberculosis, helps with UTI infections, calming effects lower stress and anxiety, antiviral, antimicrobial benefits for infections, relaxes breathing, improves wound healing, helps against common respiratory infections (e.g., prevents common respiratory infections, eases a symptom of common respiratory infections), help decrease stress, analgesic effects, rich source of antioxidants to support immunity, reduce pain and inflammation, helps improve fertility, antiviral, and antimicrobial properties help against infection, reduce systems of inflammation, promote wound healing, diuretic effects help manage arthritis (e.g., relieves pain from arthritis), help with gastrointestinal disorders (e.g., prevent, reduce symptom associated with gastrointestinal disorder), helps improve cardiovascular function with potent vasodilator effect, promote healthy cholesterol, protects against kidney stones, loosens chest congestion, prevents or reduces constipation, the drying agent helps stop bleeding from cuts, stimulates health growth, helps with indigestion, and helps manage obesity.

Example Composition E

Example Composition E comprises shilajit resin and the enrichment ingredients set forth in Table 9.

TABLE 9

| Ingredients |
|---|
| Anethi |
| orange |
| blue tansy |
| cade |
| desert sage |
| Fennel |
| frankincense carterii |
| Geranium |
| Nonatriacontylic acid |
| Octatriacontylic acid |
| Oleic acid |
| Ozubondo acid |
| Palmitic acid |
| Palmitoleic acid |
| Paullinic acid |
| Pelargonic acid |
| Pentacosylic acid |
| Pentaunsaturated fatty acids |
| peppermint |
| Pinolenic acid |
| Propionic acid |
| Psyllic acid |
| Punicic acid |
| Rosalina |
| Rumelenic acid |
| Rumenic acid |
| sage |
| Sapienic acid |
| Sardine acid |
| Sciadonic acid |
| Stearic acid |
| Stearidonic acid |
| Stearidonic acid |
| Stearidonic acid (SDA) |
| tagetes |
| Tetra-unsaturated fatty acids |
| Tetracontylic acid |
| Tetracosahexaenoic acid (Nisinic acid) |
| Tetracosanolpentaenoic acid |
| Tri-unsaturated fatty acids |
| Tricosylic acid |
| Tridecylic acid |
| turmeric organic |
| Undecylic acid |
| Vaccenic acid |
| Valeric acid |
| wintergreen |
| ylang ylang 1 |
| α-Calendic acid |
| α-Eleostearic acid |
| α-Linolenic acid |
| α-Parinaric acid |
| β-Calendic acid |
| β-Eleostearic acid |
| β-Parinaric acid |
| γ-Linolenic acid |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition E features numerous benefits to human health from the high-quality shilajit resin, cannabinoids, fatty acids, essential oils, terpenes, terpenoids, and/or essential fatty acids present therein. It is contemplated that certain combinations of the ingredients of Composition E can elicit synergistic effects on one or more of the benefits of such ingredients. Composition E can have, among others, one, some or all of the following benefits: helps against (e.g., prevents) loss of appetite, prevents flatulence, helps against digestive issues (e.g., prevents, relieves symptoms associated with), helps against UTI, flavonoids help reduce the risk of heart disease, rich source of antioxidants vitamins and minerals supports immunity and support against the development of serious diseases, antioxidant support immune system, anti-inflammatory properties, relieves skin issues and acne, helps against skin problems (e.g., reduces, relieves, prevents, treats) such as psoriasis, eczema, and seborrhea (which causes hair loss), provides antimicrobial and antiparasitic benefits, contains nutrients, and antioxidants ease menopause symptoms, reduces blood glucose levels, supports healthy cholesterol levels, supports healthy heart health, improve anemia, and anti-inflammatory property improve skin health, reduce inflammation from arthritis and arthritic pain, promote healthy gut function, improve asthma and bronchitis, reduce stress, reduce inflammation, antioxidants support the immune system, and antimicrobial properties promote a healthy response to infection, improve digestion and oral health, promote focus, lessen allergic reaction, antiviral properties help reduce flu and flu symptoms, ease body tension and headaches, provides a rich source of nutrients, minerals, and vitamins, antioxidants promote healthy aging and immune support, lower blood sugar level, promote health digestive health, relieves or prevents coughs and colds, ease sore eyes, anti-inflammatory action, antioxidant properties reduce oxidative damage, curcumin brain-boosting properties, increase stomach juices and improve digestion, ease muscle tension and pain, relaxes skin, has aphrodisiac effects, lowers blood pressure.

Example Composition F

Example Composition F can be an alternative to Example Composition E and/or Example Composition A, and comprises shilajit resin and the enrichment ingredients set forth in Table 10.

TABLE 10

| Ingredients |
|---|
| phellandrene, dill ether, limonene, p-cymene |
| beta-caryophyllene, trans-β-ocimene |
| Sabinene, camphor, myrcene, β-pinene, chamazulene |
| pinene, cadinene and cadinol; and phenols, such as guaiacol, p-cresol and viridiflorol |
| Camphor, α-Thujone, β-Thujone, 1,8-Cineole, and α-Pinene |
| trans-anethole, estragole, fenchone, α-pinene, phellandrine, camphene, dipentene, methyl chavicole-hydroxyphenylacetone, and limonene |
| α-pinene, α-thujene, limonene |
| citronellol, geraniol, geranyl formate, isomenthone, linalool, menthone |
| Nonatriacontylic acid |
| Octatriacontylic acid |
| Oleic acid |
| Ozubondo acid |
| Palmitic acid |
| Palmitoleic acid |
| Paullinic acid |
| Pelargonic acid |
| Pentacosylic acid |
| Pentaunsaturated fatty acids |
| menthol, menthone, menthofuran, isomenthone, (E)-caryophyllene, 1,8-cineole, linalool, limonene, carvone, pulegone and α-terpineol |
| Pinolenic acid |
| Propionic acid |
| Psyllic acid |
| Punicic acid |
| alpha-pinene, limonene, linanoool, cineole |
| Rumelenic acid |
| Rumenic acid |

TABLE 10-continued

| Ingredients |
|---|
| borneol, camphor, caryophyllene, cineole, elemene, humulene, ledene, pinene, and thujone |
| Sapienic acid |
| Sardine acid |
| Sciadonic acid |
| Stearic acid |
| Stearidonic acid |
| Stearidonic acid |
| Stearidonic acid (SDA) |
| ocimenes, limonene, terpinene, myrcene, α-pinene, β-pinene, (E)-β-ocimene. terpinolene |
| tagetone, dihydrotagetone, and tagetenone |
| Tetra-unsaturated fatty acids |
| Tetracontylic acid |
| Tetracosahexaenoic acid (Nisinic acid) |
| Tetracosanolpentaenoic acid |
| Tri-unsaturated fatty acids |
| Tricosylic acid |
| Tridecylic acid |
| (+)-α-turmerone, (+)-β-turmerone, (−)-α-zingiberene, (−)-β-sesquiphellandrene |
| Undecylic acid |
| Vaccenic acid |
| Valeric acid |
| methyl salicylate, α-Pinene, Myrcene, delta-3-Carene, Limonene, 3,7-Guaiadiene, and delta-Cadinene |
| Linalool, B-caryophyllene, germacrene D, benzyl acetate, methyl benzoate |
| α-Calendic acid |
| α-Eleostearic acid |
| α-Linolenic acid |
| α-Parinaric acid |
| β-Calendic acid |
| β-Eleostearic acid |
| β-Parinaric acid |
| γ-Linolenic acid |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition F features numerous benefits to human health from the high-quality shilajit resin, cannabinoids, fatty acids, essential oils, terpenes, terpenoids, and/or essential fatty acids present therein. It is contemplated that certain combinations of the ingredients of Composition F can elicit synergistic effects on one or more of the benefits of such ingredients. Composition F can have, among others, one, some or all of the following benefits: helps against (e.g., prevents) loss of appetite, prevents flatulence, helps against digestive issues (e.g., prevents, relieves symptoms associated with), helps against UTI, flavonoids help reduce the risk of heart disease, rich source of antioxidants vitamins and minerals supports immunity and support against the development of serious diseases, antioxidant support immune system, anti-inflammatory properties, relieves skin issues and acne, helps against skin problems (e.g., reduces, relieves, prevents, treats) such as psoriasis, eczema, and seborrhea (which causes hair loss), provides antimicrobial and antiparasitic benefits, contains nutrients, and antioxidants ease menopause symptoms, reduces blood glucose levels, supports healthy cholesterol levels, supports healthy heart health, improve anemia, and anti-inflammatory property improve skin health, reduce inflammation from arthritis and arthritic pain, promote healthy gut function, improve asthma and bronchitis, reduce stress, reduce inflammation, antioxidants support the immune system, and antimicrobial properties promote a healthy response to infection, improve digestion and oral health, promote focus, lessen allergic reaction, antiviral properties help reduce flu and flu symptoms, ease body tension and headaches, provides a rich source of nutrients, minerals, and vitamins, antioxidants promote healthy aging and immune support, lower blood sugar level, promote health digestive health, relieves or prevents coughs and colds, ease sore eyes, anti-inflammatory action, antioxidant properties reduce oxidative damage, curcumin brain-boosting properties, increase stomach juices and improve digestion, ease muscle tension and pain, relaxes skin, has aphrodisiac effects, lowers blood pressure.

Example Composition G

Example Composition G comprises shilajit resin and the enrichment ingredients set forth in

TABLE 11

| Ingredients |
|---|
| ambrette |
| bay laurel |
| cannabis |
| cardamom |
| CBC (cannabichromene) |
| CBCV (cannabichromevarin) |
| CBD (cannabidiol) |
| CBDA (cannabidiolic acid) |
| CBDV (cannabidivarin) |
| CBE (cannabielsoin) |
| CBG (cannabigerol) |
| CBGM (cannabigerol monomethyl ether) |
| CBGV (cannabigerovarin) |
| CBL (cannabicyclol) |
| CBN (cannabinol) |
| CBT (cannabicitran) |
| CBV (cannabivarin) |
| douglas fir |
| eucalyptus smithii |
| fenugreek |
| galbanum |
| glycine |
| hemp |
| innula |
| katafray |
| Lantana |
| manuka |
| neroli |
| opoponax |
| THC (tetrahydrocannabinol) |
| THCA (tetrahydrocannabinolic acid) |
| THCC (tetrahydrocannabiorcol) |
| THCP (tetrahydrocannabiphorol) |
| THCV (tetrahydrocannabivarin) |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition G features numerous benefits to human health from the high-quality shilajit resin, cannabinoids, fatty acids, essential oils, terpenes, terpenoids, and/or essential fatty acids present therein. It is contemplated that certain combinations of the ingredients of Composition G can elicit synergistic effects on one or more of the benefits of such ingredients. Composition G can have, among others, one, some or all of the following benefits: rich in antioxidants, help with digestive problems, nausea and vomiting, supports oral health, helps with stomach and intestinal disorders with cramps, prevents loss of appetite, helps stomach cancer, ease digestion soothes UTI, antiseptic and bactericidal properties, blood pressure-lowering, treat and eases tension and anxiety, prevents seizures, antiseptic for skin cuts, bruises, and burns, treat cold and cough symptoms, contains electrolytes, analgesic, antiviral and antibacterial properties, help against respiratory conditions such as asthma, flu, bronchitis, aids indigestion, aphrodisiac effects, improve diabetic health, improves digestion, diarrhea and flatulence, helps against seizure disorder, wound healing, contains fatty acids that promote heart health, reduce cholesterol and blood pressure, and lower the risk of heart disease, treats diabetes, soothing antiseptic effects, support respiratory health, anti-inflammatory action for rheumatism, arthritis and sprains, analgesic effect for pain, ease cold symptoms, lower blood pressure, eases symptoms of fever, wound healing, soothing sore throats, preventing tooth decay, improves digestive issues, reduce pain and inflammation, antimicrobial and antioxidant properties support immune health, treat skin conditions when applied topically, antiseptic for skin use, expectorant, antispasmodic.

Example Composition H

Example Composition H can be an alternative to Example Composition G, and comprises glycine, shilajit resin and the enrichment ingredients set forth in Table 12.

TABLE 12

| Ingredients |
|---|
| α-pinene, β-pinene, 1,8-cineole, terpineol-4, globulol |
| b-pinene, 2,5-dimethylpyrazine, 6-methyl-5-hep-ten-2-one, camphor, 3-octen-2-one, b-caryophyllene, neryl acetate, a-selinene, geranial |
| (−)-β-Pinene, (3E,5Z)-1,3,5-undecatriene (77), 2-methoxy-3-isopropyl-5-methylpyrazine(78) |
| pinene, limonene, myrcene, humulene, farnesol and caryophyllene |
| inusoniolide, 4-O-dihydroinusoniolide and 9β-hydroxyparthenolide |
| ishwarane (32, 33%), alpha-copaene (7, 41%), beta-elemene (6, 26%) |
| trans/β-caryophyllene, bicyclogermacrene, α-curcumene, sabinene, (E)-citral, 1,8-cineole, germacrene D, limonene and α-humulene |
| Leptospermone, α-and β-pinene, terpinen-4-ol, 1,8-cineole, β-triketones, linalool-and eudesmol |
| linalool, limonene, farnesol, geraniol and citral |
| β-Ocimene (82), (S,Z)-α-bisabolene (76), α-santalene (83), (e)-b-bergamotene, a-bergamotene, germacrene D, decanol |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition H features numerous benefits to human health from the high-quality shilajit resin, cannabinoids, fatty acids, essential oils, terpenes, terpenoids, and/or essential fatty acids present therein. It is contemplated that certain combinations of the ingredients of Composition H can elicit synergistic effects on one or more of the benefits of such ingredients. Composition H can have, among others, one, some or all of the following benefits: rich in antioxidants, help with digestive problems, nausea and vomiting, supports oral health, helps with stomach and intestinal disorders with cramps, prevents loss of appetite, helps stomach cancer, ease digestion soothes UTI, antiseptic and bactericidal properties, blood pressure-lowering, treat and eases tension and anxiety, prevents seizures, antiseptic for skin cuts, bruises, and burns, treat cold and cough symptoms, contains electrolytes, analgesic, antiviral and antibacterial properties, help against respiratory conditions such as asthma, flu, bronchitis, aids indigestion, aphrodisiac effects, improve diabetic health, improves digestion, diarrhea and flatulence, helps against seizure disorder, wound healing, contains fatty acids that promote heart health, reduce cholesterol and blood pressure, and lower the risk of heart disease, treats diabetes, soothing antiseptic effects, support respiratory health, anti-inflammatory action for rheumatism, arthritis and sprains, analgesic effect for pain, ease cold symptoms, lower blood pressure, eases symptoms of fever, wound healing, soothing sore throats, preventing tooth decay, improves digestive issues, reduce pain and inflammation, antimicrobial and antioxidant properties support immune health, treat skin conditions when applied topically, antiseptic for skin use, expectorant, antispasmodic.

Example Composition I

Example Composition I comprises shilajit resin and the enrichment ingredients set forth in Table 13.

TABLE 13

| Ingredients |
|---|
| amyris |
| beeswax absolute |
| cape chamomile |
| chamomile |
| davana oil |
| elemi |
| fir siberian |
| ginger |
| jasmine |
| kunzea |
| laurel |
| lovage |
| marjoram |
| naartjie |
| ocimum gratissimum |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition I features numerous benefits to human health from the high-quality shilajit resin, cannabinoids, fatty acids, essential oils, terpenes, terpenoids, and/or essential fatty acids present therein. It is contemplated that certain combinations of the ingredients of Composition I can elicit synergistic effects on one or more of the benefits of such ingredients. Composition I can have, among others, one, some or all of the following benefits: promotes sleep, relieves stress and anxiety, boost immunity with the antioxidants, soothing skin effects, great source of calories and nutrients, nourishing skin, treating irritated skin like eczema, rashes, and burns, reduces menstrual cramping, alleviates allergic reactions, fights anxiety and depression, improves sleep, has antiviral properties, for cough, cold, influenza and measles, normalize menstruation, promote healing, improves digestion and promotes health hormone secretion, stimulates nervous response, pain relief, and anti-inflammatory response, reduces stress, alleviates pain, fights infection with a rich terpene content, rich source of antioxidants boosts immunity, lower high blood pressure, avoids heart disease, promotes healthy aging, antidepressant effects, aphrodisiac effect enhance libido, sedative effects help with sleep, alleviates joint pain, relieves headaches and respiratory conditions, relieves mental exhaustion, stress and tension, ease digestion and reduce flatulence, sooth UTI symptoms and pain, bactericidicidal effects help against infection, relieves indigestion, diuretic effects, treats kidney stone, rich in folate and minerals beneficial effects for women with PCOS, reduces anxiety, anti-inflammatory, antimicrobial effects, anti-inflammatory and antimicrobial effects help against infection, rich in Vitamins for proper health, antidepressant effects, sedative, and calming effects, helps against digestive discomfort, lower blood sugar levels, antimicrobial effects.

Example Composition J

Example Composition J can be an alternative to Example Composition I, and comprises shilajit resin and the enrichment ingredients set forth in Table 14.

TABLE 14

| Ingredients |
|---|
| Valerianol, β-eudesmol |
| b-eudesmol |
| Linalyl acetate, a-pinene |
| alpha-bisabolol, chamazulene |
| davanone, linalool, dehydro-a-linalool, terpinen-4 oil, nordavanone (c11-terpenoid), devanafurans |
| phellandrene, dipentene |
| alpha pinene, limonene, camphene, myrcene, D3 carene |
| Zingiberene, β-Bisabolene, Cineol, Geraniol, Linalool, Citral, Borneol, α-Farnesene, β-Phellandrene and Curcumene |
| β-caryophyllene, trans-nerolidol, (E,E)-α-farnesene |
| Alpha-pinene, Viridiflorol, Ecualyptol |
| 1,8-cineole, linalool, α-terpinyl acetate, α-pinene, β-pinene, sabinene, α-terpineol, terpineol-4 |
| β-phellandrene, α-terpinyl acetate, and Z-ligustilide |
| pinene, sabinene, terpinene, limonene and linalool |
| methyl anthranilate, octanol, sisensal, citral, citronellal, y-terpinene, limonene, myrcene, p-cymene, linalool, citronellol |
| Eugenol, cis-ocimene, γ-muurolene, (Z,E)-α-farnesene, α-trans-bergamotene, and β-caryophyllene |

It is contemplated that ingredients can be removed. It is contemplated that ingredients can be added from other Examples described herein and/or from the ingredients listed in Table 1.

Example composition J features numerous benefits to human health from the high-quality shilajit resin, cannabinoids, fatty acids, essential oils, terpenes, terpenoids, and/or essential fatty acids present therein. It is contemplated that certain combinations of the ingredients of Composition J can elicit synergistic effects on one or more of the benefits of such ingredients. Composition J can have, among others, one, some or all of the following benefits: promotes sleep, relieves stress and anxiety, boost immunity with the antioxidants, soothing skin effects, great source of calories and nutrients, nourishing skin, treating irritated skin like eczema, rashes, and burns, reduces menstrual cramping, alleviates allergic reactions, fights anxiety and depression, improves sleep, has antiviral properties, for cough, cold, influenza and measles, normalize menstruation, promote healing, improves digestion and promotes health hormone secretion, stimulates nervous response, pain relief, and anti-inflammatory response, reduces stress, alleviates pain, fights infection with a rich terpene content, rich source of antioxidants boosts immunity, lower high blood pressure, avoids heart disease, promotes healthy aging, antidepressant effects, aphrodisiac effect enhance libido, sedative effects help with sleep, alleviates joint pain, relieves headaches and respiratory conditions, relieves mental exhaustion, stress and tension, ease digestion and reduce flatulence, sooth UTI symptoms and pain, bactericidicidal effects help against infection, relieves indigestion, diuretic effects, treats kidney stone, rich in folate and minerals beneficial effects for women with PCOS, reduces anxiety, anti-inflammatory, antimicrobial effects, anti-inflammatory and antimicrobial effects help against infection, rich in Vitamins for proper health, antidepressant effects, sedative, and calming effects, helps against digestive discomfort, lower blood sugar levels, antimicrobial effects.

Example Composition K

Example Composition K comprises shilajit resin and the enrichment ingredients set forth in Table 15.

TABLE 15

| Ingredient |
|---|
| angelica archangelica |
| benzoin |
| cinnamon |
| fragonia |
| grapefruit |
| hinoki wood |
| juniper leaf |
| khella |
| Lavandin |
| mastic leaf |
| oregano |
| Palmarosa |
| rhododendron |
| sandalwood |
| Tangerine |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition K features numerous benefits to human health from the high-quality shilajit resin, cannabinoids, fatty acids, essential oils, terpenes, terpenoids, and/or essential fatty acids present therein. It is contemplated that certain combinations of the ingredients of Composition K can elicit synergistic effects on one or more of the benefits of such ingredients. Composition K can have, among others, one, some or all of the following benefits: soothe stomach indigestion, reduce anxiety, control smoking cravings, antimicrobial, antiseptic, anti-inflammatory and astringent effects for skin use, blood sugar-lowering effects and other anti-diabetic effects, rich in antioxidants to fight age, help against cancer, anti-inflammatory properties, improves insulin response and diabetic health, rich in antioxidants, relieves anxiety and tension, improve immune system, decongests respiratory system, helps against urinary tract infections (UTIs) and kidney and bladder stones, relieve joint and muscle pain, vasodilating effect, promote healthy cholesterol levels, antimicrobial benefits, fights depression, reduce pain, treats respiratory discomforts, stomach and intestinal ulcers, breathing problems, muscle aches and bacterial and fungal infection, antibacterial agent contains phytonutrients that helps against infection, a great source of antioxidants and vitamins, calming, balancing effects aid in sleep, antimicrobial benefits fight infection, reduces effects of fever, reduce inflammation and pain, manage diabetes symptoms, prevent cancer, manage the common cold, manage infections (UTI), helps manage anxiety, rich sources of nutrients, antioxidants to support immunity, promote proper brain health, anti-cancer properties.

Example Composition L

Example Composition L can be an alternative to Example Composition K, and comprises shilajit resin and the enrichment ingredients set forth in Table 16.

TABLE 16

| Ingredients |
|---|
| limonene, α-phellandrene, pinene, p-cymene, terpinolene, myrcene, fenchone, linalool, α-terpineol, cadinene, borneol, β-caryophyllene, bisabolol, angelica lactone, |
| sumaresinolic acid, Sia resinolic acid, styrol, Vanillin and phenyl propyl cinnamate |
| eugenol, caryophyllene oxide, α-humulene, α-phellandrene, and α-pinene |
| alpha-pinene, beta-pinene, myrcene, 1,8-cineole, linalool, geraniol, terpinene4-ol, terpineol |
| Limonene |
| α-thujene, α-pinene, camphene, sabinene, β-pinene, myrcene, α-terpinene, limonene, p-cymene, Y-terpinene, terpinolene, terpinen-4-ol, α-terpineol, bornyl acetate, α-terpinyl acetate, cis-thujopsene, trans-muurola-4(14),5-diene, germacrene D, δ-cadinene, elemol, beyerene |
| α-pinene, myrcene, limonene, γ-terpinene, linalool, terpine-4-ol, geraniol, borneol |
| γ-pyrones, khellin, visnagin, visnaginone, ammiol, Khellinol, khellol, visammiol, khellinin, khellinone |
| Linalool, Linalyl Acetate, Camphor, and 1,8-Cineole, terpinene-4-ol, lavandulyl acetate, borneol |
| monoterpene hydrocarbons α-pinene, β-myrcene and camphen |
| carvacrol, thymol, γ-terpinene and p-cymene; while terpinen-4-ol, linalool, β-myrcene, trans-sabinene hydrate, and β-caryophyllene |
| Geraniol, Geranyl acetate, (E,Z)-Farnesol, Linalool, (E)-Beta-Ocimene, B-caryophyllene, Geranial, Caryophyllene oxide, B-Myrcene, Elemol, (Z,Z)-Farnesol |
| Limonene, Pinene (Alpha/Beta), Delta-Cadinene, Cis-Ocimene, Trans-Beta-Farnesene, Alpha-Selinene. Others in smaller concentration include: Myrcene, Para-Cymene, Trans Beta-Ocimen, Linalyl Propionate, Bornyl Acetate, Citronellyl Acetate, Alpha Copaene, Beta-Caryophyllene, and many others in $<1\%$ |
| α- & β-santalols (90%), α- & β santalenes |
| alpha-pinene, myrcene, d-limonene, linalool, terpineol, alpha-humulene, beta-caryophyllene, alpha-bisabolol, beta-pinene |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition L features numerous benefits to human health from the high-quality shilajit resin, cannabinoids, fatty acids, essential oils, terpenes, terpenoids, and/or essential fatty acids present therein. It is contemplated that certain combinations of the ingredients of Composition L can elicit synergistic effects on one or more of the benefits of such ingredients. Composition L can have, among others, one, some or all of the following benefits: soothe stomach indigestion, reduce anxiety, control smoking cravings, antimicrobial, antiseptic, anti-inflammatory and astringent effects for skin use, blood sugar-lowering effects and other anti-diabetic effects, rich in antioxidants to fight age, help against cancer, anti-inflammatory properties, improves insulin response and diabetic health, rich in antioxidants, relieves anxiety and tension, improve immune system, decongests respiratory system, helps against urinary tract infections (UTIs) and kidney and bladder stones, relieve joint and muscle pain, vasodilating effect, promote healthy cholesterol levels, antimicrobial benefits, fights depression, reduce pain, treats respiratory discomforts, stomach and intestinal ulcers, breathing problems, muscle aches and bacterial and fungal infection, antibacterial agent contains phytonutrients that helps against infection, a great source of antioxidants and vitamins, calming, balancing effects aid in sleep, antimicrobial benefits fight infection, reduces effects of fever, reduce inflammation and pain, manage diabetes symptoms, prevent cancer, manage the common cold, manage infections (UTI), helps manage anxiety, rich sources of nutrients, antioxidants to support immunity, promote proper brain health, anti-cancer properties.

Example Composition M

Example Composition M comprises shilajit resin and the enrichment ingredients set forth in Table 17.

TABLE 17

| Ingredients |
|---|
| cinnamon leaf |
| curry leaf |
| frangiapani absolute |
| hyssop decumbens |
| lavender |
| mimosa absolute |
| niaouli |
| osmanthus absolute |
| ravintsara organic |
| rose |
| Siberian fir wild |
| tulsi |
| vetiver |
| Zdravets |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition M features numerous benefits to human health from the high-quality shilajit resin, cannabinoids, fatty acids, essential oils, terpenes, terpenoids, and/or essential fatty acids present therein. It is contemplated that certain combinations of the ingredients of Composition M can elicit synergistic effects on one or more of the benefits of such ingredients. Composition < can have, among others, one, some or all of the following benefits: blood sugar-lowering effects and other anti-diabetic effects, rich in antioxidants to fight to age, protect against cancer, rich in vitamins A, B, C, B2, and minerals iron, and calcium, treat dysentery, constipation, diarrhea, helps against morning sickness and nausea, alleviate inflammation, headaches, back discomfort and tinnitus, loosen mucous and relieve bronchial congestion and spasms, relieves cold sores, improves sleep, and treat skin blemishes like eczema, acne and others, reduce blood pressure, soothing and nourishing properties to the skin, astringent and antiseptic, eases anxiety and sensitivity, stimulates the immune system, treats sinusitis, and rhinitis, antiseptic and antifungal properties, rich in antioxidants to combat aging and oxidative stress, may help with weight loss, detoxifying properties, helps relieve, antiviral and bacterial conditions, supports the immune system, relieves colds and cough, eases pain, stress and anxiety, antimicrobial properties help with infection, ease depressive episodes, reduces stress, alleviate pain, fights infection with rich terpene content, vitamins in tulsi boost immunity, reduces fever and has analgesic properties, lower blood glucose, relieving stress helps relieve insomnia and nervousness, relieves pain, lowers blood pressure, a natural relaxant, prevent heart disease and high blood pressure.

Example Composition N

Example Composition N can be an alternative to Example Composition M, and comprises shilajit resin and the enrichment ingredients set forth in Table 18.

TABLE 18

| Ingredients |
| --- |
| eugenol, trans-3-caren-2-ol, benzyl benzoate, caryophyllene, eugenyl acetate, α-phellandrene, α-pinene |
| linalool, elemol, geranyl acetate, myrcene, allo-ocimene, alpha-terpinene, (E)-beta-ocimene |
| Limonene, Linalool, α-cedrene, caryophyllene oxide, (E, E)-α-farnesene |
| α-pinene, Sabinene, β-pinene, Limonene, Pinocamphone, iso-pinocamphone, myrtenyl methyl ether, β-bourbonene, β-caryophyllene, allo-aromadendrene, germacrene-D, Elemol, Spathulenol, β-phellandrene, (E)-β-ocimene, γ-terpinene, Linalool, Pinocarveol, Myrtenol, methyl eugenol, α-gurjunene, Bicyclogermacrene, |
| Linalool, α-Terpineol, γ-Terpineol, Borneol, Terpinen-4-ol, Isobomeol, Nerol, Lavandulol, Linalyl acetate, Geranyl acetate, Neryl acetate, Octene-3-yl acetate, Lavandulyl acetate, Myrcene, α-Pinene, β-Pinene, Camphene, (E)-β-Ocimene, (Z)-β-Ocimene, β-Phellandrene, Eucalyptol, β-Caryophyllene, β-Farnesene, Germacrene, α-Humulene |
| d-limonene, myrcene, beta-caryophyllene, linalool |
| 1,8-cineole, a-pinene, (+)-Limonene, a-terpineol, B-pinene, viridiflorol |
| β-ionone, cis-linalool oxide (furan), trans-linalool oxide (furan), linalool, (E)-2-hexenal, (Z)-3-hexen-1-ol, hexanal |
| 1.8 cineole, terpineol, pinenes |
| Linalool, citronellol, geraniol, alkenes, nerol, 2-phenylethanol |
| Bornyl acetate. Camphene. A-Pinene. gamma-3-Carene. (+)-Limonene. Santene |
| caryophyllene oxide, linalool, myrcene, methyl chavicol, gamma caryophyllene, alpha humulene, thymol, cineole, methyl-eugenol, camphor |
| (−)-Vetiselinenol (55), (+)-α-vetivone (56), (−)-β-vetivone (57), (+)-khusimol (58), (−)-khusimone (59) |
| Germacrone, Beta-elemene, Germacrene B, Gamma-Elemene, Gamma Terpinene, A, B Pinene |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition N features numerous benefits to human health from the high-quality shilajit resin, cannabinoids, fatty acids, essential oils, terpenes, terpenoids, and/or essential fatty acids present therein. It is contemplated that certain combinations of the ingredients of Composition N can elicit synergistic effects on one or more of the benefits of such ingredients. Composition N can have, among others, one, some or all of the following benefits: blood sugar-lowering effects and other anti-diabetic effects, rich in antioxidants to fight to age, protect against cancer, rich in vitamins A, B, C, B2, and minerals iron, and calcium, treat dysentery, constipation, diarrhea, helps against morning sickness and nausea, alleviate inflammation, headaches, back discomfort and tinnitus, loosen mucous and relieve bronchial congestion and spasms, relieves cold sores, improves sleep, and treat skin blemishes like eczema, acne and others, reduce blood pressure, soothing and nourishing properties to the skin, astringent and antiseptic, eases anxiety and sensitivity, stimulates the immune system, treats sinusitis, and rhinitis, antiseptic and antifungal properties, rich in antioxidants to combat aging and oxidative stress, may help with weight loss, detoxifying properties, helps relieve, antiviral and bacterial conditions, supports the immune system, relieves colds and cough, eases pain, stress and anxiety, antimicrobial properties help with infection, ease depressive episodes, reduces stress, alleviate pain, fights infection with rich terpene content, vitamins in tulsi boost immunity, reduces fever and has analgesic properties, lower blood glucose, relieving stress helps relieve insomnia and nervousness, relieves pain, lowers blood pressure, a natural relaxant, prevent heart disease and high blood pressure.

Example Composition O

Example Composition O comprises shilajit resin and the enrichment ingredients set forth in Table 19.

TABLE 19

| Ingredients |
| --- |
| arnica |
| caraway |
| clementine |
| fenugreek |
| immortelle absolute |
| leleshwa |
| lemon myrtle |
| Lemongrass |
| Liquidambar |
| Mugwort |
| orris root |
| pine scotch |
| raspberry seed |
| rosemary et cineole |
| sea buckthorn |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition O features numerous benefits to human health from the high-quality shilajit resin, cannabinoids, fatty acids, essential oils, terpenes, terpenoids, and/or essential fatty acids present therein. It is contemplated that certain combinations of the ingredients of Composition O can elicit synergistic effects on one or more of the benefits of such ingredients. Composition O can have, among others, one, some or all of the following benefits: Rich in antioxidants and nutrients, which helps reduce inflammation, anticancer compounds help against cancer, can be used topically for bruises, wound healing, phlebitis, inflammation, insect bites, and to reduce swelling and muscle pain, alleviates digestive issues like bloating, heartburn and gas, reduce stomach spasms, acts as an expectorant, promote liver healing and gallbladder health, reduce dyspepsia and edema, promote bile flow, rich in nutrients like calcium, zinc, and magnesium contains antioxidants to combat oxidative stress and aging relieves infection, control bacterial growth, relieve pain, has anti-inflammatory effect, reduce swelling and fever, help lower blood sugar levels and cholesterol levels, can alleviate sore throat, cough, asthma, and stomach problems, tonic is used to boost energy, helps treat colic, diarrhea, constipation, and stomach cramps, and helps against vomiting, stimulates appetite, stimulates digestion and improve bile flow, eases headache and muscle pains, clears acne and clarifies skin, eases headache, natural insect repellant, relieves respiratory tract, anti-inflammatory activities help with swelling, antibacterial properties help with infection, compounds in raspberry help prevent cancer, promote healthy hair and skin, and nutrients and minerals for bone health, rich source of antioxidants and anti-inflammatory compounds to boost immunity may help improve blood circulation, and prevent coronary diseases, treats stomach or intestinal problems, improves blood pressure or blood cholesterol, and improve symptoms of cirrhosis, lowering blood sugar levels, boosting testosterone, and increasing milk production in breastfeeding mothers.

Example Composition P

Example Composition P can be an alternative to Example Composition O, and comprises shilajit resin and the enrichment ingredients set forth in Table 20.

TABLE 20

| Ingredients |
|---|
| 2,5-dimethoxy-p-cymene, cumene, thymol methyl ether, 2,6-diisopropylanisole, decanal, 1,2,2,3-tetramethylcyclopent-3-enol, α-pinene oxide, β-maaliene, E-α-bergamotene, lippifoli-1(6)-en-5-one, 7-epi-silphiperfol-5-ene, α-isocomene, 2,5-dimetoxy-p-cymene, E-caryophyllene, and caryophyllene oxide |
| carvone, limonene, carveol |
| Myrcene, D-limonene, beta-caryophyllene, linalool, terpineol, fenchol, borneol, caryophyllene-oxide, camphene, gernaiol |
| b-pinene, 2,5-dimethylpyrazine, 6-methyl-5-hep-ten-2-one, camphor, 3-octen-2-one, b-caryophyllene, neryl acetate, a-selinene, geranial |
| neryl acetate, rosifoliol, neryl propionate, y-curcumene, linalool, nerol, rosifoliol, geranyl propionate, ar-curcumene, italidione, alpha-eudesmol, limonene |
| Fenchol, 1,8-cineole, a-terpinol, a-pinene, trans-pinene hydrate, terpinen-4-ol, camphene |
| ctiral, neral and geranial, myrcene, linalool, citronellal, cyclocitral, methyl-heptenone |
| myrcene, limonene, citral, geraniol, citronellol, geranyl acetate, neral, nerol |
| terpinen-4-ol, α-terpineol, α-pinene, sabinene |
| camphor, eucalyptol, alpha-pinene, and beta-pinene |
| (+)-cis-γ-lrone (60), (+)-cis-α-irone (61) |
| beta-pinene, p-cymene, alpha-bisabolol, eugenol, carvone, terpineol, citral, bornyl aceteate, terpineol, camphene |
| alpha humulene, alpha pinene, alpha terpineol, beta caryophyllene, beta pinene, d-limonene, geraniol, linalool, myrcene |
| α-pinene, myrcene, 1,8-cineole, camphor, camphene, α-terpineol, and borneol. |
| β-maaliene, γ-selinene, cadina-1(10),6,8-triene, germacrene B, isocalamendiol, isolongifolanones, shyobunon |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition P features numerous benefits to human health from the high-quality shilajit resin, cannabinoids, fatty acids, essential oils, terpenes, terpenoids, and/or essential fatty acids present therein. It is contemplated that certain combinations of the ingredients of Composition P can elicit synergistic effects on one or more of the benefits of such ingredients. Composition P can have, among others, one, some or all of the following benefits: Rich in antioxidants and nutrients, which helps reduce inflammation, anticancer compounds help against cancer, can be used topically for bruises, wound healing, phlebitis, inflammation, insect bites, and to reduce swelling and muscle pain, alleviates digestive issues like bloating, heartburn and gas, reduce stomach spasms, acts as an expectorant, promote liver healing and gallbladder health, reduce dyspepsia and edema, promote bile flow, rich in nutrients like calcium, zinc, and magnesium contains antioxidants to combat oxidative stress and aging relieves infection, control bacterial growth, relieve pain, has anti-inflammatory effect, reduce swelling and fever, help lower blood sugar levels and cholesterol levels, can alleviate sore throat, cough, asthma, and stomach problems, tonic is used to boost energy, helps treat colic, diarrhea, constipation, and stomach cramps, and helps against vomiting, stimulates appetite, stimulates digestion and improve bile flow, eases headache and muscle pains, clears acne and clarifies skin, eases headache, natural insect repellent, relieves respiratory tract, anti-inflammatory activities help with swelling, antibacterial properties help with infection, compounds in raspberry help prevent cancer, promote healthy hair and skin, and nutrients and minerals for bone health, rich source of antioxidants and anti-inflammatory compounds to boost immunity may help improve blood circulation, and prevent coronary diseases, treats stomach or intestinal problems, improves blood pressure or blood cholesterol, and improve symptoms of cirrhosis, lowering blood sugar levels, boosting testosterone, and increasing milk production in breastfeeding mothers.

Example Composition Q

Example Composition Q comprises shilajit resin and the enrichment ingredients set forth in Table 21.

TABLE 21

| Ingredients |
|---|
| calamus |
| cocoa bean |
| coriander |
| cypress |
| Fennel |
| katafray |
| lemon tea tree |
| litsea cubeba |
| myrrh |
| rosewood |
| spikenard |
| turmeric |
| vanilla absolute |
| wintergreen |
| yarrow blue |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition Q features numerous benefits to human health from the high-quality shilajit resin, cannabinoids, fatty acids, essential oils, terpenes, terpenoids, and/or essential fatty acids present therein. It is contemplated that certain combinations of the ingredients of Composition Q can elicit synergistic effects on one or more of the benefits of such ingredients. Composition Q can have, among others, one, some or all of the following benefits: a mild sedative, helps manage rheumatoid arthritis, induces relaxation and sleep, rich polyphenol and flavonoids to help lower blood pressure, cholesterol and sugars, reduce risk of diabetes, improve circulation, lower blood sugar, rich in immune boosting antioxidants, may protect brain health, treat fungal infections, improve hair health, helps against varicose veins (e.g., prevents, reduces), supports healthy heart health, improve anemia, and anti-inflammatory property improve skin health, anti-inflammatory action for rheumatism, arthritis, sprains, analgesic effect for pain, boost health body response, reduce headache and pains, promote healthy skin, boosts mood, antibacterial properties, improves digestive system, kills bacteria, supports oral and skin health, combats pain and swelling, relieves depression, serves as an aphrodisiac, anti-inflammatory effects for pain, relieves anxiety, depression, insomnia, and stress, has antifungal properties, is anti-inflammatory for pain, anti-inflammatory action, antioxidant properties reduce oxidative damage, curcumin brain-boosting properties, reduce startle reflexes and also provide some relief from sleep apnea, vanillin offers antioxidant, anticancer, and anti-inflammatory properties, increase stomach juices and improve digestion, topical application for joint pain and sore muscles helps relieve muscle pain, boost immunity and inflammatory response, promote wound healing, prevent neurological diseases.

Example Composition R

Example Composition R can be an alternative to Example Composition Q, and comprises shilajit resin and the enrichment ingredients set forth in Table 22.

TABLE 22

| Ingredients |
| --- |
| α-asarone, (E)-methylisoeugenol, methyleugenol, β-asarone, α-cedrene, camphor |
| Linalool, myrcene and ocimene |
| β-linalool, α-pinene, γ-terpinene, camphor, sylvestrene, β-pinene, and o-cymene |
| B-pinene, terpineol |
| trans-anethole, estragole, fenchone, α-pinene, phellandrine, camphene, dipentene, methyl chavicole-hydroxyphenylacetone, and limonene |
| ishwarane (32, 33%), alpha-copaene (7, 41%), beta-elemene (6, 26%) |
| α-pinene. sabinene, α-terpinene, limonene, p-cymene, 1,8-cineole, γ-terpinene, terpinolene, terpinen-4-ol, α-terpineol, aromadendrene, ledene, δ-cadinene, globulol, viridifloral |
| limonol. β-linalool, 1,8-cineole, elemicin, methyleugenol, esteragenol, deoxygeraniol, citronellal, α-citral, α-pinene, myristicin, β-Geraniol, α-terpineol, α-ocimene, β-pinene, terpinen-4-ol, β-caryophyllene. limonol acetate, β-ocimene, shikomol, 2-carene, 3-carene, m-cymene, p-cymene, γ-terpinene, 6,7-epoxy-linalool, rosenoxide, limonol formate, β-elemene, β-patchoulene, β-selinene, methylisoeugenol, β-caryophyllene oxide |
| cadinene, curzerene, (1-3)-Furanoeudesma-Diene, Lindestrene, Elemene, Germacrene |
| linalool, α-terpineol, geraniol, benzyl benzoate |
| calarene, beta maaliene, valerena-4,7(11)-diene |
| germacrene D synthase, (S)-β-bisabolene synthase, α-humulene synthase, β-eudesmol synthase, (−)-caryolan-1-ol synthas, α-zingiberene/β-sesquiphellandrene |
| limonene, pinene, and beta-caryophyllene, vanillin |
| methyl salicylate, α-Pinene, Myrcene, delta-3-Carene, Limonene, 3,7-Guaiadiene, and delta-Cadinene |
| Sabinene, β-Pinene, Chamazulene |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition R features numerous benefits to human health from the high-quality shilajit resin, cannabinoids, fatty acids, essential oils, terpenes, terpenoids, and/or essential fatty acids present therein. It is contemplated that certain combinations of the ingredients of Composition R can elicit synergistic effects on one or more of the benefits of such ingredients. Composition R can have, among others, one, some or all of the following benefits: a mild sedative, helps manage rheumatoid arthritis, induces relaxation and sleep, rich polyphenol and flavonoids to help lower blood pressure, cholesterol and sugars, reduce risk of diabetes, improve circulation, lower blood sugar, rich in immune boosting antioxidants, may protect brain health, treat fungal infections, improve hair health, helps against varicose veins (e.g., prevents, reduces), supports healthy heart health, improve anemia, and anti-inflammatory property improve skin health, anti-inflammatory action for rheumatism, arthritis, sprains, analgesic effect for pain, boost health body response, reduce headache and pains, promote healthy skin, boosts mood, antibacterial properties, improves digestive system, kills bacteria, supports oral and skin health, combats pain and swelling, relieves depression, serves as an aphrodisiac, anti-inflammatory effects for pain, relieves anxiety, depression, insomnia, and stress, has antifungal properties, is anti-inflammatory for pain, anti-inflammatory action, antioxidant properties reduce oxidative damage, curcumin brain-boosting properties, reduce startle reflexes and also provide some relief from sleep apnea, vanillin offers antioxidant, anticancer, and anti-inflammatory properties, increase stomach juices and improve digestion, topical application for joint pain and sore muscles helps relieve muscle pain, boost immunity and inflammatory response, promote wound healing, prevent neurological diseases.

Example Composition S

Example Composition S comprises shilajit resin and the enrichment ingredients set forth in Table 23.

TABLE 23

| Ingredients |
| --- |
| angelica glauca |
| black currant bud absolute |
| blue tansy |
| carnation absolute |
| coffee |
| holy basil |
| katafray |
| lavandin grosso |
| Lemon organic |
| mastic leaf |
| petitgrain bigarade |
| pine wild |
| star anise |
| thyme |
| valerian |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition S features numerous benefits to human health from the high-quality shilajit resin, cannabinoids, fatty acids, essential oils, terpenes, terpenoids, and/or essential fatty acids present therein. It is contemplated that certain combinations of the ingredients of Composition S can elicit synergistic effects on one or more of the benefits of such ingredients. Composition S can have, among others, one, some or all of the following benefits: ease gastrointestinal discomfort, treat or prevent for anorexia, reduces anxiety, nourish skin, antihistamine properties for allergic reactions, anti-inflammatory for swelling and pain. antioxidant support immune system, anti inflammatory properties, relieves skin issues and acne, reduce inflammation and swelling, soothing sensation reduces anxiety and stress, use as a natural sedative, boost energy levels, help lower the risk of T2DM, supports heart health, and promote longevity, protect against infection, lower blood sugar, lower cholesterol, ease joint pain, protect stomach, anti-inflammatory action for rheumatism, arthritis, sprains, analgesic effect for pain, fights (e.g., treats) depression, reduces pain, is a natural expectorant for the respiratory system, aid in weight loss and reduce risks of heart disease, relieves sore throat, prevents or treats/alleviates stomach and intestinal ulcers, prevents or treats/alleviates breathing problems, muscle aches, and bacterial and fungal infection, treats insomnia, fatigue and stress induces sleep, contains vitamins and phenols for the immune system, pycnogenol anti-inflammatory benefits, reduces the risk of chronic disease, rich in antioxidant terpenes that help boost immunity and offer anti-inflammatory, anti-microbial properties, rich in vitamin c for immune support, potassium, rich in manganese for bone health, lower blood pressure and fighting acne, increases the amount of gamma-aminobutyric acid (GABA) in the brain, sedative effects helps reduce anxiety and stress, treats insomnia.

Example Composition T

Example Composition T can be an alternative to Example Composition S, and comprises shilajit resin and the enrichment ingredients set forth in Table 24.

TABLE 24

| Ingredients |
| --- |
| methyl octene, limonene, β-phellendrene, β-pinene), phthalides [(Z)-3-butyli-dene phthalide (Z)- and (E)-ligustilide], citronellyl acetate |
| sabinene, δ-3-carene, terpinolene, β-caryophyllene, β-phellandrene, cis-β-ocimene, γ-terpinene, terpinen-4-ol, limonene |
| Sabinene, camphor, myrcene, β-pinene, chamazulene, |
| eugenols, (Z)-3-hexenyl acetate, methyl benzoate, β-caryophyllene, and decanal |
| cafestol, cafestol |
| caryophyllene oxide, linalool, myrcene, methyl chavicol, gamma caryophyllene, alpha humulene, thymol, cineole, methyl-eugenol and camphor |
| ishwarane (32, 33%), alpha-copaene (7, 41%), beta-elemene (6, 26%) |
| Linalool, linalyl acetate, camphor |
| limonene, camphenes, α-terpineol, α-phellandrene, and 4-terpineol, α-selinene, caryophyllene oxide, t-nerolidol, valencene |
| monoterpene hydrocarbons α-pinene, β-myrcene and camphen |
| Linalyl acetate, Linalol, Citral, Geraniol, Limonene, Linalool |
| pinene, terpineol |
| α-Pinene, β-Pinene, cis-Anethole, trans-Anethole, Limonene, Linalool |
| thymol, p-cymene, carvacrol, linalool, β-caryphyllene, terpinen-4-ol |
| ar-curcumene, α,β,γ-patchoulenes, patchouli alcohol, β-sitosterol, valeranone, maali-oxide, maaliol, calarene, β-bergamotene |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition T features numerous benefits to human health from the high-quality shilajit resin, cannabinoids, fatty acids, essential oils, terpenes, terpenoids, and/or essential fatty acids present therein. It is contemplated that certain combinations of the ingredients of Composition T can elicit synergistic effects on one or more of the benefits of such ingredients. Composition T can have, among others, one, some or all of the following benefits: ease gastrointestinal discomfort, treat or prevent for anorexia, reduces anxiety, nourish skin, antihistamine properties for allergic reactions, anti-inflammatory for swelling and pain. antioxidant support immune system, anti inflammatory properties, relieves skin issues and acne, reduce inflammation and swelling, soothing sensation reduces anxiety and stress, use as a natural sedative, boost energy levels, help lower the risk of T2DM, supports heart health, and promote longevity, protect against infection, lower blood sugar, lower cholesterol, ease joint pain, protect stomach, anti-inflammatory action for rheumatism, arthritis, sprains, analgesic effect for pain, fights (e.g., treats) depression, reduces pain, is a natural expectorant for the respiratory system, aid in weight loss and reduce risks of heart disease, relieves sore throat, prevents or treats/alleviates stomach and intestinal ulcers, prevents or treats/alleviates breathing problems, muscle aches, and bacterial and fungal infection, treats insomnia, fatigue and stress induces sleep, contains vitamins and phenols for the immune system, pycnogenol anti-inflammatory benefits, reduces the risk of chronic disease, rich in antioxidant terpenes that help boost immunity and offer anti-inflammatory, anti-microbial properties, rich in vitamin c for immune support, potassium, rich in manganese for bone health, lower blood pressure and fighting acne, increases the amount of gamma-aminobutyric acid (GABA) in the brain, sedative effects helps reduce anxiety and stress, treats insomnia.

Example Composition U

Example Composition U comprises shilajit resin and the enrichment ingredients set forth in Table 25.

TABLE 25

| Ingredients |
| --- |
| ajwain |
| artemisia annua |
| bergamot mint |
| boronia |
| citronella |
| combava lime |
| hyssop decumbens |
| kunzea |
| linden blossom |
| manuka |
| mugwort |
| myrtle |
| opoponax |
| tobacco |
| lemon |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition U features numerous benefits to human health from the high-quality shilajit resin, cannabinoids, fatty acids, essential oils, terpenes, terpenoids, and/or essential fatty acids present therein. It is contemplated that certain combinations of the ingredients of Composition U can elicit synergistic effects on one or more of the benefits of such ingredients. Composition U can have, among others, one, some or all of the following benefits: antibacterial and antifungal properties, helps to lower blood pressure, relieves indigestion, useful in the treatment of different cancers, helps with constipation, indigestion and diarrhea, terpenes found helpful against herpes, influenza and hepatitis, anti-inflammatory, anti-spasmodic, analgesic and carminative properties, soothe upset or nervous tummies, nausea and travel sickness, alleviate anxiety and stress, induce calming experience, has aphrodisiac effects, insect repellent, antifungal properties, lifts mood and fights fatigue, promotes oral health, detoxifying components boost immunity, reduce stress and inflammation, loosen mucous and relieve bronchial congestion and spasms, relieves cold sores, relieves, reduces or prevents joint pain, relieves headaches and respiratory conditions, relieves mental exhaustion, stress, tension, promotes relaxation, fights inflammation and pain, diuretic and diaphoretic effects, wound healing, soothes sore throats, prevents tooth decay, improves digestive issues, boosts energy, helps treat colic, diarrhea, constipation and stomach cramps, and helps against vomiting, treating lung infections including bronchitis, whooping cough and tuberculosis, treat or prevent bladder conditions, diarrhea, yeast infection, and parasitic worms, antiseptic for skin use, expectorant, antispasmodic, laxative, induce vomiting, expectorant, aids in weight loss, reduces inflammation and fevers, has calming effect that helps reduce muscle tension and anxiety.

Example Composition V

Example Composition V can be an alternative to Example Composition U, and comprises shilajit resin and the enrichment ingredients set forth in Table 26.

TABLE 26

| Ingredients |
|---|
| thymol, gammaterpene, orthocymene, heptaethylene, glycol, monododecyl ether, oleic acid, linoleic acid |
| artemisinin, deoxyartemisinin, artemisinic acid, arteannuin-B, stigmasterol, friedelin, friedelan-3 beta-ol, artemetin, and quercetagetin 6,7,3',4'-tetramethyl ether |
| linalool, linalyl acetate, a-terpineol, beta-caryophyllene, nerol |
| spathulenol and 1 (10),5-germacradien-4-ol, moronic acid, moronic aldehyde (novel), betulonic acid and lupeol, the alkaloids dictamnine, evolitrine, isodictamnine and hordenine, and 8-(3,7-dimethyl-2,6-octadienyl)-7-hydroxy coumarin |
| Geraniol, linalool, citronellol |
| beta-pinenes, limonenes, terpinenes, cineoles, citroneloles |
| α -pinene, Sabinene, β -pinene, Limonene, Pinocamphone, iso - pinocamphone, myrtenyl methyl ether, β -bourbonene, β -caryophyllene, allo -aromadendrene, germacrene-D, Elemol, Spathulenol, β - phellandrene, (E)-β-ocimene, γ - terpinene, Linalool, Pinocarveol, Myrtenol, methyl eugenol, α -gurjunene, Bicyclogermacrene, Alpha-pinene, Viridiflorol, Ecualyptol |
| alpha pinene, linalool, nerol, terpineol, limonene, taxerol |
| Leptospermone, α- and β-pinene, terpinen-4-ol, 1,8-cineole, ß-triketones, linalool- and eudesmol |
| camphor, eucalyptol, alpha-pinene, and beta-pinene |
| Geranyl acetate, 1,8-cineole, α-terpinyl acetate, methyleugenol, linalool, α-terpineol, β-caryophyllene, α-humulene, Trans-caryophyllene oxide, humulene epoxide II |
| β-Ocimene (82), (S,Z)-α-bisabolene (76), α-santalene (83), (e)-b-bergamotene, a-bergamotene, germacrene D, decanol |
| β-pinene, limonene, and γ-terpinene |
| neral, geranial, δ-limonene, β-ocimene, and δ-+-3-carene, germacrene-D, trans-caryophyllene, bicyclogermacrene, and α-curcumene |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition U features numerous benefits to human health from the high-quality shilajit resin, cannabinoids, fatty acids, essential oils, terpenes, terpenoids, and/or essential fatty acids present therein. It is contemplated that certain combinations of the ingredients of Composition U can elicit synergistic effects on one or more of the benefits of such ingredients. Composition U can have, among others, one, some or all of the following benefits: antibacterial and antifungal properties, helps to lower blood pressure, relieves indigestion, useful in the treatment of different cancers, helps with constipation, indigestion and diarrhea, terpenes found helpful against herpes, influenza and hepatitis, anti-inflammatory, anti-spasmodic, analgesic and carminative properties, soothe upset or nervous tummies, nausea and travel sickness, alleviate anxiety and stress, induce calming experience, has aphrodisiac effects, insect repellent, antifungal properties, lifts mood and fights fatigue, promotes oral health, detoxifying components boost immunity, reduce stress and inflammation, loosen mucous and relieve bronchial congestion and spasms, relieves cold sores, relieves, reduces or prevents joint pain, relieves headaches and respiratory conditions, relieves mental exhaustion, stress, tension, promotes relaxation, fights inflammation and pain, diuretic and diaphoretic effects, wound healing, soothes sore throats, prevents tooth decay, improves digestive issues, boosts energy, helps treat colic, diarrhea, constipation and stomach cramps, and helps against vomiting, treating lung infections including bronchitis, whooping cough and tuberculosis, treat or prevent bladder conditions, diarrhea, yeast infection, and parasitic worms, antiseptic for skin use, expectorant, antispasmodic, laxative, induce vomiting, expectorant, aids in weight loss, reduces inflammation and fevers, has calming effect that helps reduce muscle tension and anxiety.

Example Composition V

Example Composition V comprises shilajit resin and the enrichment ingredients set forth in Table 27.

TABLE 27

| Ingredients |
|---|
| cape snowbush |
| coriander |
| damiana |
| davana oil |
| douglas fir |
| frankincense frereana |
| helichrysum bractiferium |
| jasmine sambac absolute |
| lavandula antinea |
| lime |
| lippia javanica |
| neroli |
| plai |
| sea buckthorn |
| tulip |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition V features numerous benefits to human health from the high-quality shilajit resin, cannabinoids, fatty acids, essential oils, terpenes, terpenoids, and/or essential fatty acids present therein. It is contemplated that certain combinations of the ingredients of Composition V can elicit synergistic effects on one or more of the benefits of such ingredients. Composition V can have, among others, one, some or all of the following benefits: relieves muscle spasms, stop bleeding, antiseptic and antiviral properties, lower blood sugar, rich in immune boosting antioxidants, protect brain health, treats headaches, prevent or treat depression, boosts mental and physical stamina, antiviral properties for cough, cold, influenza and measles, normalize menstruation, promotes healing, antiseptic for skin cuts, bruises and burns, treat cold and cough symptoms, contains electrolytes, soothes skin, removes fine lines, wrinkles and scars, promotes natural healing of skin, and wounds, reduce arthritis, anti-inflammatory properties, regulate cholesterol, anti-spasmodic, rich in antioxidants for healthy aging benefits, aid in weight loss, aid in management of alzheimers and parkinson's disease, boost brain health, treat anxiety, depression and restlessness, help with digestive issues, relieve pain and headaches, boost immunity, reduce heart disease factors, aid in iron absorption, treats cough, colds and headaches, treats digestive disorders, analgesic effect, reduce pain and inflammation, antimicrobial and antioxidant properties support immune health, treat skin conditions wen applied topically, stimulate immunity and vitality, antimicrobial compounds fight infection, soothes muscle pain, treat stomach or intestinal problems, improve blood pressure or blood cholesterol, improve symptoms of cirrhosis, diuretic, antiseptic, anti-inflammatory benefits.

Example Composition W

Example Composition W can be an alternative to Example Composition V, and comprises shilajit resin and the enrichment ingredients set forth in Table 28.

TABLE 28

| Ingredients |
|---|
| linalyl acetate, α-pinene |
| β-linalool, α-pinene, γ-terpinene, camphor, sylvestrene, β-pinene, and o-cymene |
| p-cymene; β-sitosterol; 1,8-cineole; apigenin, α-pinene; β-carotene; β-pinene; tannins; thymol |
| davanone, linalool, dehydro-a-linalool, terpinen-4 oil, nordavanone (c11-terpenoid), devanafurans |
| limonene, camphene, and isobornyl acetate |
| α-pinene, α-amyrin, β-amyrin, β-phellandrene |
| neryl acetate, rosifoliol, neryl propionate, y-curcumene, linalool, nerol, rosifoliol, geranyl propionate, ar-curcumene, italidione, alpha-eudesmol, limonene |
| (E)-ocimene, linalool, and α-farnesene |
| camphor, 1,8-cineol, carvacrol |
| limonene; limonene/beta-pinene/gamma-terpinene; and limonene/linalyl acetate/linalool |
| 3-methyl-6-(1-methylethylidene)-cyclohexen-2-en-1-one (piperitenone)2-methyl-6-methylene-2,7-octadien-4-one (ipsdienone, myrcenone), myrcene and (E)- and (Z)-tagetenone |
| linalool, limonene, farnesol, geraniol and citral |
| sabinene, y-terpinene, a-terpinene, terpinen (E)-1-(3,4-dimethoxyphenol) butadiene4-ol |
| β-maaliene, γ-selinene, cadina-1(10),6,8-triene, germacrene B, isocalamendiol, isolongifolanones, shyobunon |
| a-pinene, d-limonene, beta-ocimene, 2,6-octadiene-2,6-dimethyl, longifolene, a-farnesene |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition W features numerous benefits to human health from the high-quality shilajit resin, cannabinoids, fatty acids, essential oils, terpenes, terpenoids, and/or essential fatty acids present therein. It is contemplated that certain combinations of the ingredients of Composition W can elicit synergistic effects on one or more of the benefits of such ingredients. Composition W can have, among others, one, some or all of the following benefits: relieves muscle spasms, stop bleeding, antiseptic and antiviral properties, lower blood sugar, rich in immune boosting antioxidants, protect brain health, treats headaches, prevent or treat depression, boosts mental and physical stamina, antiviral properties for cough, cold, influenza and measles, normalize menstruation, promotes healing, antiseptic for skin cuts, bruises and burns, treat cold and cough symptoms, contains electrolytes, soothes skin, removes fine lines, wrinkles and scars, promotes natural healing of skin, and wounds, reduce arthritis, anti-inflammatory properties, regulate cholesterol, anti-spasmodic, rich in antioxidants for healthy aging benefits, aid in weight loss, aid in management of alzheimers and parkinson's disease, boost brain health, treat anxiety, depression and restlessness, help with digestive issues, relieve pain and headaches, boost immunity, reduce heart disease factors, aid in iron absorption, treats cough, colds and headaches, treats digestive disorders, analgesic effect, reduce pain and inflammation, antimicrobial and antioxidant properties support immune health, treat skin conditions wen applied topically, stimulate immunity and vitality, antimicrobial compounds fight infection, soothes muscle pain, treat stomach or intestinal problems, improve blood pressure or blood cholesterol, improve symptoms of cirrhosis, diuretic, antiseptic, anti-inflammatory benefits.

Example Composition X

Example Composition X comprises shilajit resin and the enrichment ingredients set forth in Table 29.

TABLE 29

| Ingredients |
|---|
| buchu crenulata |
| celery seed |
| frankincense negleta |
| geranium |
| grapefruit pink |
| innula |
| jasmine sambac absolute |
| lavander |
| linden blossom |
| lovage |
| naartjie |
| petitgrain sur fleur |
| rosemary Spanish |
| sandalwood nut |
| spruce absolute black |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition X features numerous benefits to human health from the high-quality shilajit resin, cannabinoids, fatty acids, essential oils, terpenes, terpenoids, and/or essential fatty acids present therein. It is contemplated that certain combinations of the ingredients of Composition X can elicit synergistic effects on one or more of the benefits of such ingredients. Composition X can have, among others, one, some or all of the following benefits: anti-inflammatory, treats UTI infections and acts as diuretic, useful in gout treatment, rich in vitamins, minerals, and antioxidants that support bone health, support blood formation, may aid in blood sugar regulation, useful as an effective expectorant and other respiratory issues such as colds and the flu, useful to maintain or treat asthma, improve gut health, prevent or treat anxiety and depression, antimicrobial and analgesic benefits, promote immune health and healthy aging, prevent insulin resistance and diabetes, soothing antiseptic benefits for respiratory tract diseases, relieve skin conditions, useful against parasites, rich in antioxidants for healthy aging benefits, aid in weight loss, aid in the management of Alzheimers and Parkinson's disease, boost brain health, helps with insomnia, improves sleep and reduces depression, helps with anxiety and pain from headaches and migraine, promote relaxation, fight inflammation and pain, diuretic and diaphoretic effects, digestive aid, reduce flatulence and other stomach discomforts, treat UTI and kidney stones, help with joint pain and migraines, anti-inflammatory and antimicrobial effects help against infection, rich in Vitamins for proper health, antidepressant effects, sedative, and calming effects, relaxing effect help relieve anxiety, stress, and even depression, antiseptic benefits against common infections, antispasmodic for coughs and respiratory congestion, may improve brain function, focus, concentration, and memory retention, the analgesic effect may be used for mild pain, help ease stress, helps with weight loss, reduces the risk of heart disease, and helps manage inflammation, soothing respiratory problems such as coughs, colds, flu, bronchitis, catarrh, sinus congestion, asthma, and allergies.

Example Composition Y

Example Composition Y can be an alternative to Example Composition X, and comprises shilajit resin and the enrichment ingredients set forth in Table 30.

TABLE 30

| Ingredients |
|---|
| limonene, menthone, diosphenol and one of its isomers (ψ)-diosphenol, and l-pulegone, 9-mercapto-p-menthan-3-one |
| d-limonene, selinene, sesquiterpene alcohols |
| α-pinene, α-thujen, β-pinene, myrcene, sabinene, limonene, p-cymene, beta-caryophyllene |
| geraniol, linalool, citronellol |
| limonen, myrcene, a-pinene, sabinene, geraniol, citronellal, linalool, decyl acetate, neryl acetate, terpinen-4-ol, Nootkatone |
| inusoniolide, 4-O-dihydroinusoniolide and 9β-hydroxyparthenolide, inulin, |
| (E)-ocimene, linalool, and α-farnesene |
| Caryophyllene, Limonene, Pinene |
| alpha pinene, linalool, nerol, terpineol, limonene, taxerol |
| β- phellandrene, α-terpinyl acetate, and Z- ligustilide |
| methyl anthranilate, octanol, sisensal, citral, citronellal, y-terpinene, limonene, myrcene, p-cymene, linalool, citronellol |
| linanlyl acetate, linalool, myrcene, geranyl acetate, alpha-terpineol |
| α-pinene, myrcene, 1,8-cineole, camphor, camphene, α-terpineol, and borneol. |
| α-santalol. β-Santalol |
| camphene, a-pinene, delta-3-caren, bornyl acetate |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition Y features numerous benefits to human health from the high-quality shilajit resin, cannabinoids, fatty acids, essential oils, terpenes, terpenoids, and/or essential fatty acids present therein. It is contemplated that certain combinations of the ingredients of Composition Y can elicit synergistic effects on one or more of the benefits of such ingredients. Composition Y can have, among others, one, some or all of the following benefits: anti-inflammatory, treats UTI infections and acts as diuretic, useful in gout treatment, rich in vitamins, minerals, and antioxidants that support bone health, support blood formation, may aid in blood sugar regulation, useful as an effective expectorant and other respiratory issues such as colds and the flu, useful to maintain or treat asthma, improve gut health, prevent or treat anxiety and depression, antimicrobial and analgesic benefits, promote immune health and healthy aging, prevent insulin resistance and diabetes, soothing antiseptic benefits for respiratory tract diseases, relieve skin conditions, useful against parasites, rich in antioxidants for healthy aging benefits, aid in weight loss, aid in the management of Alzheimers and Parkinson's disease, boost brain health, helps with insomnia, improves sleep and reduces depression, helps with anxiety and pain from headaches and migraine, promote relaxation, fight inflammation and pain, diuretic and diaphoretic effects, digestive aid, reduce flatulence and other stomach discomforts, treat UTI and kidney stones, help with joint pain and migraines, anti-inflammatory and antimicrobial effects help against infection, rich in Vitamins for proper health, antidepressant effects, sedative, and calming effects, relaxing effect help relieve anxiety, stress, and even depression, antiseptic benefits against common infections, antispasmodic for coughs and respiratory congestion, may improve brain function, focus, concentration, and memory retention, the analgesic effect may be used for mild pain, help ease stress, helps with weight loss, reduces the risk of heart disease, and helps manage inflammation, soothing respiratory problems such as coughs, colds, flu, bronchitis, catarrh, sinus congestion, asthma, and allergies.

Example Composition Z

Example Composition Z comprises shilajit resin and the enrichment ingredients set forth in Table 31.

TABLE 31

| Ingredients |
|---|
| Cajeput |
| CBC (cannabichromene) |
| CBCV (cannabichromevarin) |
| CBD (cannabidiol) |
| CBDA (cannabidiolic acid) |
| CBDV (cannabidivarin) |
| CBE (cannabielsoin) |
| CBG (cannabigerol) |
| CBGM (cannabigerol monomethyl ether) |
| CBGV (cannabigerovarin) |
| CBL (cannabicyclol) |
| CBN (cannabinol) |
| CBT (cannabicitran) |
| CBV (cannabivarin) |
| chamomile |
| coconut pulp |
| eucalyptus lemon |
| fragonia |
| frankincense papyrifera |
| ginger |
| helichrysum Italicum |
| lavender |
| rose oil |
| spruce |
| THC (tetrahydrocannabinol) |
| THCA (tetrahydrocannabinolic acid) |
| THCC (tetrahydrocannabiorcol) |
| THCP (tetrahydrocannabiphorol) |
| THCV (tetrahydrocannabivarin) |

TABLE 31-continued

| Ingredients |
|---|
| Thyme |
| vanilla |
| vetiver |
| ylang ylang |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition Z features numerous benefits to human health from the high-quality shilajit resin, cannabinoids, fatty acids, essential oils, terpenes, terpenoids, and/or essential fatty acids present therein. It is contemplated that certain combinations of the ingredients of Composition Z can elicit synergistic effects on one or more of the benefits of such ingredients. Composition Z can have, among others, one, some or all of the following benefits: alleviates anxiety, stress, and depression, offers skincare benefits as an antiseptic and antioxidant, reduces pain, anti-inflammatory properties, regulate cholesterol, anti-spasmodic, antibacterial and mucolytic properties, support respiratory function, boost memory and focus, antiseptic, analgesic, treats skin wounds and inflammation, treats colds, effective expectorant and other respiratory issues such as colds and the flu, used to maintain (or treat) asthma, improve gut health, offers anti-inflammatory, and antioxidant effects, reduces nausea treats indigestion, lower blood sugar, highly nutritious, a great source of calories and nutrients, help control blood sugar levels and blood pressure, contains powerful antioxidants, treats inflammation of the respiratory tract, arthritis pain, nerve pain and feelings of tension, reduce inflammation, and reduce infection, may help with alopecia areata, reduce startle reflexes and also provide some relief from sleep apnea, vanillin offers antioxidant, anticancer and anti-inflammatory properties, relaxing effects on skin, aphrodisiac effects, lower blood pressure, relieves indigestion and its effects, promote healing and pain reduction, relieve anxiety, relieving stress helps relieve insomnia and nervousness, relieves pain, stimulate circulation, reduces pain and inflammation, antioxidants, antimicrobial qualities support immune system, treat skin disorders and reduce signs of skin aging, treats leucorrhoea, skin inflammatory conditions.

Example Composition AA

Example Composition AA can be an alternative to Example Composition Z, and comprises shilajit resin and the enrichment ingredients set forth in Table 32.

TABLE 32

| Ingredients |
|---|
| Beta-Caryophyllene, D-Limonene, Alpha-Caryophyllene, Linalool, Valencene |
| (−)-Vetiselinenol (55), (+)-α-vetivone (56), (−)-β-vetivone (57), (+)-khusimol (58), (−)-khusimone (59) |
| 1.8 Cineole, limomene, alpha terpineol, Beta-Caryophyllene |
| a-pinene, a-cedrene, aromadendrene, beta-caryophyllene, limonene |
| alpha-pinene, beta-pinene, myrcene, 1,8-cineole, linalool, geraniol, terpinene4-ol, terpineol |
| carvacrol, thymol, linalool, cineol, camphor borneol |
| citronellal, limonene |
| citronellol, geraniol, geranyl acetate, farnesol |
| lactones |
| linalool, a-terpineol, y-terpineol, borneol, isoborneol, terpinen-4-oil, nerol, lavandulol, linalyl acetate, geranyl acetate, neryl acetate, octene-3-yl-acetate, lavandulyl acetate, myrcene, a-pinene, b-pinene, camphene, (e)-b-ocimene, (z)-b-ocimene, beta- phellandrene, eucalyptol, β-Caryophyllene, β-Farnesene, Germacrene, α-Humulene |
| linalool, B-caryophyllene, germacrene D, benzyl acetate, methyl benzoate |
| α-bisabolol, chamazulene, farnesene, α-pinene, lactones |
| α-pinene, α-amyrin, β-amyrin, phellandrene, camphene |
| α-pinene, β-pinene, camphene and limonene |
| β-bisabolene, α-curcumene, zingiberene, α-farnesene, and β-sesquiphellandrene |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition AA features numerous benefits to human health from the high-quality shilajit resin, cannabinoids, fatty acids, essential oils, terpenes, terpenoids, and/or essential fatty acids present therein. It is contemplated that certain combinations of the ingredients of Composition AA can elicit synergistic effects on one or more of the benefits of such ingredients. Composition AA can have, among others, one, some or all of the following benefits: alleviates anxiety, stress, and depression, offers skincare benefits as an antiseptic and antioxidant, reduces pain, anti-inflammatory properties, regulate cholesterol, anti-spasmodic, antibacterial and mucolytic properties, support respiratory function, boost memory and focus, antiseptic, analgesic, treats skin wounds and inflammation, treats colds, effective expectorant and other respiratory issues such as colds and the flu, used to maintain (or treat) asthma, improve gut health, offers anti-inflammatory, and antioxidant effects, reduces nausea treats indigestion, lower blood sugar, highly nutritious, a great source of calories and nutrients, help control blood sugar levels and blood pressure, contains powerful antioxidants, treats inflammation of the respiratory tract, arthritis pain, nerve pain and feelings of tension, reduce inflammation, and reduce infection, may help with alopecia areata, reduce startle reflexes and also provide some relief from sleep apnea, vanillin offers antioxidant, anticancer and anti-inflammatory properties, relaxing effects on skin, aphrodisiac effects, lower blood pressure, relieves indigestion and its effects, promote healing and pain reduction, relieve anxiety, relieving stress helps relieve insomnia and nervousness, relieves pain, stimulate circulation, reduces pain and inflammation, antioxidants, antimicrobial qualities support immune system, treat skin disorders and reduce signs of skin aging, treats leucorrhoea, skin inflammatory conditions.

Example Composition BB

Example Composition BB comprises shilajit resin and the enrichment ingredients set forth in Table 33.

TABLE 33

| Ingredients |
|---|
| agarwood |
| ajwain |

TABLE 33-continued

| Ingredients |
| --- |
| cedarwood |
| choya loban |
| cinnamon cassia |
| clove bud |
| geranium |
| lavender |
| lavender spike |
| lime |
| lippia javanica |
| lovage |
| eroli |
| spearmint |
| tea tree |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition BB features numerous benefits to human health from the high-quality shilajit resin, cannabinoids, fatty acids, essential oils, terpenes, terpenoids, and/or essential fatty acids present therein. It is contemplated that certain combinations of the ingredients of Composition BB can elicit synergistic effects on one or more of the benefits of such ingredients. Composition BB can have, among others, one, some or all of the following benefits: treat skin disorders and reduce signs of skin aging, treats leucorrhoea and skin inflammatory conditions, antibacterial and antifungal properties, help lower blood pressure, relieves indigestion, blood sugar-lowering effects and other anti-diabetic effects, rich in antioxidants to fight age, help against cancer, treats cough, colds, and headaches, treats digestive disorders, analgesic effect, antiseptic properties for skin and mouth may boost wound healing, antifungal, and antibacterial properties prevent acne and nail fungus, help balance hormones, lower blood sugar and improve digestion, Rich source of antioxidants and vitamin C to boost immunity, reduce heart disease factors, aid in iron absorption, contains nutrients and minerals, high in antioxidants to combat oxidative stress and to promote and assist liver health, treat digestive system, relieve spasm, relieve pain, anti-inflammatory properties for skin and scalp, acne, help with hair loss, when inhaled, highly effective against various respiratory problems such as bronchitis, asthma, laryngitis, asthma, coughs and others, beneficial for those with anxiety, and depression, potential antimicrobial and analgesic benefits, contains antibacterial characteristics that aid in the healing of wounds, burns, and scarred or injured skin, relieves stress, and headaches, treat colds, and acts as a decongestant, reduce pain and inflammation, antimicrobial and antioxidant properties support immune health, treat skin conditions when applied topically, digestive aid, prevent flatulence and other stomach discomforts, treats UTI and kidney stones, relieve joint pain and migraines.

Example Composition CC

Example Composition CC can be an alternative to Example Composition BB, and comprises shilajit resin and the enrichment ingredients set forth in Table 34.

TABLE 34

| Ingredients |
| --- |
| a-copaene, b-caryophyllene, |
| beta pinene, limonene, linalool |
| caryophyllene, carvone, ipsenone, ipsdienone, limonene, linalool, myrcene, myrcenone, ocimenone, p-cymene, piperitenone, sabinene, and tagetenone |
| caryopyllene |
| citronellol, geraniol, linalool |
| limonene; limonene/beta-pinene/gamma-terpinene; and limonene/linalyl acetate/linalool |
| Linalool, a-terpineol, y-terpineol, borneol, isoborneol, terpinen-4-oil, nerol, lavandulol, linalyl acetate, geranyl acetate, neryl acetate, octene-3-yl-acetate, lavandulyl acetate, myrcene, a-pinene, b-pinene, camphene, (e)-b-ocimene, (z)-b-ocimene, beta- phellandrene, eucalyptol, β-Caryophyllene, β-Farnesene, Germacrene, α-Humulene |
| linalool, cineole and camphor |
| Pinene, beta Pinene, Carvone, Cineole, Caryophyllene, Linalool, Limolene, Menthol, Myrcene |
| terpinolene, 1,8-cineole, terpinen-4-ol |
| Thujopsene, Cedrol, ∀-Cedrene, ∃-Cedrene, ∀-Copaene, Widdrol |
| thymol, gammaterpene, orthocymene, heptaethylene, glycol, monododecyl ether, oleic acid, linoleic acid |
| ugenol, caryophyllene oxide, α-humulene, α-phellandrene, and α-pinene |
| β- phellandrene, α-terpinyl acetate, and Z- ligustilide |
| β-agarofuran, α-agarofuran, Nor-ketoagarofuran, Agarospirol, β-eudesmol, kusunol |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition CC features numerous benefits to human health from the high-quality shilajit resin, cannabinoids, fatty acids, essential oils, terpenes, terpenoids, and/or essential fatty acids present therein. It is contemplated that certain combinations of the ingredients of Composition CC can elicit synergistic effects on one or more of the benefits of such ingredients. Composition CC can have, among others, one, some or all of the following benefits: treat skin disorders and reduce signs of skin aging, treats leucorrhoea and skin inflammatory conditions, antibacterial and antifungal properties, help lower blood pressure, relieves indigestion, blood sugar-lowering effects and other anti-diabetic effects, rich in antioxidants to fight age, help against cancer, treats cough, colds, and headaches, treats digestive disorders, analgesic effect, antiseptic properties for skin and mouth may boost wound healing, antifungal, and antibacterial properties prevent acne and nail fungus, help balance hormones, lower blood sugar and improve digestion, Rich source of antioxidants and vitamin C to boost immunity, reduce heart disease factors, aid in iron absorption, contains nutrients and minerals, high in antioxidants to combat oxidative stress and to promote and assist liver health, treat digestive system, relieve spasm, relieve pain, anti-inflammatory properties for skin and scalp, acne, help with hair loss, when inhaled, highly effective against various respiratory problems such as bronchitis, asthma, laryngitis, asthma, coughs and others, beneficial for those with anxiety, and depression, potential antimicrobial and analgesic benefits, contains antibacterial characteristics that aid in the healing of wounds, burns, and scarred or injured skin, relieves stress, and headaches, treat colds, and acts as a decongestant, reduce pain and inflammation, antimicrobial and antioxidant properties support immune health, treat skin conditions when applied topically, digestive aid, prevent flatulence and other stomach discomforts, treats UTI and kidney stones, relieve joint pain and migraines.

Example Composition DD

Example Composition DD comprises shilajit resin and the enrichment ingredients set forth in Table 35.

TABLE 35

| Ingredients |
|---|
| blue tansy |
| cilantro |
| cinnamon |
| citronella |
| Fennel |
| fenugreek |
| hemp |
| lemon |
| lippia javanica |
| naartjie |
| palmarosa |
| peppercorn |
| spikenard |
| vetiver |
| ylang ylang |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition DD features numerous benefits to human health from the high-quality shilajit resin, cannabinoids, fatty acids, essential oils, terpenes, terpenoids, and/or essential fatty acids present therein. It is contemplated that certain combinations of the ingredients of Composition DD can elicit synergistic effects on one or more of the benefits of such ingredients. Composition DD can have, among others, one, some or all of the following benefits: benefits (e.g., improve, maintain health) to the heart and circulatory health, help prevent kidney stones, treats cough, colds and headaches, treats digestive disorders, analgesic effect, relaxing effects on skin, aphrodisiac effects, lower blood pressure, relieving stress helps relieve insomnia and nervousness, relieves pain, popular insect repellant has antifungal properties, may help lift mood and fight fatigue, antioxidant support immune system, anti-inflammatory properties, relieves skin issues and acne, lowering blood sugar levels, boosting testosterone, and increasing milk production in breastfeeding mothers, calming, balancing effects aid in sleep, antimicrobial benefits fight infection, reduces effects of fever, supports healthy heart health, improve anemia, and anti-inflammatory property improve skin health, acts as a diuretic, antiseptic, helps against urinary infections, relieves colds and cough, relieves anxiety, depression, insomnia, and stress, has antifungal properties, is anti-inflammatory for pain, lower blood sugar, rich in immune-boosting antioxidants, protect brain health, contains fatty acids that promote heart health, reduce cholesterol and blood pressure, and lower the risk of heart disease, blood sugar-lowering effects and other anti-diabetic effects, rich in antioxidants to fight age, help against cancer, anti-inflammatory and antimicrobial effects help against infection, rich in Vitamins for proper health, antidepressant effects, sedative, and calming effects.

Example Composition EE

Example Composition EE can be an alternative to Example Composition DD, and comprises shilajit resin and the enrichment ingredients set forth in Table 36.

TABLE 36

| Ingredients |
|---|
| (−)-Vetiselinenol (55), (+)-α-vetivone (56), (−)-β-vetivone (57), (+)-khusimol (58), (−)-khusimone (59) |
| (S)-(+)-linalool, coriandrol, (R)-(−)-linalool, licareol |
| b-pinene, 2,5-dimethylpyrazine, 6-methyl-5-hep-ten-2-one, camphor, 3-octen-2-one, b-caryophyllene, neryl acetate, a-selinene, geranial |
| calarene, beta maaliene, valerena-4,7(11)-diene |
| caryophyllene, carvone, ipsenone, ipsdienone, limonene, linalool, myrcene, myrcenone, ocimenone, p-cymene, piperitenone, sabinene, and tagetenone |
| eugenol, caryophyllene oxide, α-humulene, α-phellandrene, and α-pinene |
| Geraniol, Geranyl acetate, (E,Z)-Farnesol, Linalool, (E)-Beta-Ocimene, B-caryophyllene, Geranial, Caryophyllene oxide, B-Myrcene, Elemol, (Z,Z)-Farnesol |
| Geraniol, linalool, citronellol |
| Germacrene-D, cadinene, caryophyllene |
| limonene, camphenes, α-terpineol, α-phellandrene, and 4-terpineol, α-selinene, caryophyllene oxide, t-nerolidol, valencene |
| limonene, pinene, phellandrene, carene, cardanol |
| methyl anthranilate, octanol, sisensal, citral, citronellal, y-terpinene, limonene, myrcene, p-cymene, linalool, citronellol |
| pinene, limonene, myrcene, humulene, farnesol and caryophyllene |
| Sabinene, camphor, myrcene, β-pinene, chamazulene, |
| Shilajit manufactured under this patent |
| trans-anethole, estragole, fenchone, α-pinene, phellandrine, camphene, dipentene, methyl chavicole-hydroxyphenylacetone, and limonene |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition EE features numerous benefits to human health from the high-quality shilajit resin, cannabinoids, fatty acids, essential oils, terpenes, terpenoids, and/or essential fatty acids present therein. It is contemplated that certain combinations of the ingredients of Composition EE can elicit synergistic effects on one or more of the benefits of such ingredients. Composition EE can have, among others, one, some or all of the following benefits: benefits (e.g., improve, maintain health) to the heart and circulatory health, help prevent kidney stones, treats cough, colds and headaches, treats digestive disorders, analgesic effect, relaxing effects on skin, aphrodisiac effects, lower blood pressure, relieving stress helps relieve insomnia and nervousness, relieves pain, popular insect repellant has antifungal properties, may help lift mood and fight fatigue, antioxidant support immune system, anti-inflammatory properties, relieves skin issues and acne, lowering blood sugar levels, boosting testosterone, and increasing milk production in breastfeeding mothers, calming, balancing effects aid in sleep, antimicrobial benefits fight infection, reduces effects of fever, supports healthy heart health, improve anemia, and anti-inflammatory property improve skin health, acts as a diuretic, antiseptic, helps against urinary infections, relieves colds and cough, relieves anxiety, depression, insomnia, and stress, has antifungal properties, is anti-inflammatory for pain, lower blood sugar, rich in immune-boosting antioxidants, protect brain health, contains fatty acids that promote heart health, reduce cholesterol and blood pressure, and lower the risk of heart disease, blood sugar-lowering effects and other anti-diabetic effects, rich in antioxidants to fight age, help against cancer, anti-inflammatory and antimicrobial effects help against infection, rich in Vitamins for proper health, antidepressant effects, sedative, and calming effects.

Example Composition FF

Example Composition FF comprises shilajit resin and the enrichment ingredients set forth in Table 37.

TABLE 37

| Ingredients |
| --- |
| bergamot |
| boronia |
| davana |
| desert sage |
| helichrysum bractiferium |
| hemp |
| hinoki wood |
| lemon myrtle |
| mimosa absolute |
| myrrh |
| naartjie |
| ocimum gratissimum |
| sea buckthorn |
| valerian |
| zdravets |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition FF features numerous benefits to human health from the high-quality shilajit resin, cannabinoids, fatty acids, essential oils, terpenes, terpenoids, and/or essential fatty acids present therein. It is contemplated that certain combinations of the ingredients of Composition FF can elicit synergistic effects on one or more of the benefits of such ingredients. Composition FF can have, among others, one, some or all of the following benefits: rich in nutrients like calcium, zinc, and magnesium contains antioxidants to combat oxidative stress and aging, relieves infection, regenerate skin, slow aging, alleviate anxiety, antiviral properties, for cough, cold, influenza, and measles, normalize menstruation, promote healing, contains nutrients, and antioxidants ease menopause symptoms, reduce blood glucose levels, support healthy cholesterol levels, contains fatty acids that promote heart health, reduce cholesterol and blood pressure, lower the risk of heart disease, helps against digestive discomfort, lower blood sugar levels, antimicrobial effects, relieves anxiety and tension, improves immune system, decongests respiratory system, anti-inflammatory and antimicrobial effects help against infection, rich in Vitamins for proper health, antidepressant effects, sedative, and calming effects, soothing and nourishing properties to the skin, astringent and antiseptic, eases anxiety and sensitivity, treat stomach or intestinal problems, improves blood pressure or blood cholesterol, improve symptoms of cirrhosis, anti-inflammatory to regulate cholesterol, stimulate the cells of the liver, acts as an antispasmodic, kills bacteria, supports oral and skin health, combats pain and swelling, increases the amount of gamma-aminobutyric acid (GABA) in the brain, sedative effects help reduce anxiety and stress, treat insomnia, alleviate anxiety and stress, induce calming experience, have aphrodisiac effects, generally used to lower blood pressure, a natural relaxant, prevent heart disease and high blood pressure.

Example Composition GG

Example Composition GG can be an alternative to Example Composition FF, and comprises shilajit resin and the enrichment ingredients set forth in Table 38.

TABLE 38

| Ingredients |
| --- |
| (R)-p-mentha-1,8-diene, citral, linalool, (R)-p-mentha-1,8-diene |
| ar-curcumene, $\alpha,\beta,\gamma$-patchoulenes, patchouli alcohol, $\beta$-sitosterol, |
| valeranone, maali-oxide, maaliol, calarene, $\beta$-bergamotene |
| cadinene, curzerene, (1-3)-Furanoeudesma-Diene, Lindestrene, |
| Elemene, Germacrene |
| Camphor, $\alpha$-Thujone, $\beta$-Thujone, 1,8-Cineole, and $\alpha$-Pinene |
| ctiral, neral and geranial, myrcene, linalool, citronellal, cyclocitral, |
| methyl-heptenone |
| d-limonene, myrcene, beta-caryophyllene, linalool |
| davanone, linalool, dehydro-a-linalool, terpinen-4 oil, nordavanone |
| (c11-terpenoid), devanafurans |
| Eugenol, cis-ocimene, $\gamma$-muurolene, (Z,E)-$\alpha$-farnesene, $\alpha$-trans- |
| bergamotene, and $\beta$-caryophyllene |
| Germacrone, Beta-elemene, Germacrene B, Gamma-Elemene, |
| Gamma Terpinene, A, B Pinene |
| methyl anthranilate, octanol, sisensal, citral, citronellal, y-terpinene, |
| limonene, myrcene, p-cymene, linalool, citronellol |
| neryl acetate, rosifoliol, neryl propionate, y-curcumene, linalool, |
| nerol, rosifoliol, geranyl propionate, ar-curcumene, italidione, alpha- |
| eudesmol, limonene |
| pinene, limonene, myrcene, humulene, farnesol and caryophyllene |
| spathulenol and 1 (10),5-germacradien-4-ol, moronic acid, moronic |
| aldehyde (novel), betulonic acid and lupeol, the alkaloids dictamnine, |
| evolitrine, isodictamnine and hordenine, and 8-(3,7-dimethyl-2,6- |
| octadienyl)-7-hydroxycoumarin |
| $\alpha$-thujene, $\alpha$-pinene, camphene, sabinene, $\beta$-pinene, myrcene, $\alpha$- |
| terpinene, limonene, p-cymene, Y-terpinene, terpinolene , terpinen-4- |
| ol, $\alpha$-terpineol, bornyl acetate, $\alpha$-terpinyl acetate, cis-thujopsene, |
| trans-muurola-4(14),5-diene, germacrene D, $\delta$-cadinene, |
| elemol, beyerene |
| $\beta$-maaliene, $\gamma$-selinene, cadina-1(10),6,8-triene, germacrene B, |
| isocalamendiol, isolongifolanones, shyobunon |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition GG features numerous benefits to human health from the high-quality shilajit resin, cannabinoids, fatty acids, essential oils, terpenes, terpenoids, and/or essential fatty acids present therein. It is contemplated that certain combinations of the ingredients of Composition GG can elicit synergistic effects on one or more of the benefits of such ingredients. Composition GG can have, among others, one, some or all of the following benefits: rich in nutrients like calcium, zinc, and magnesium contains antioxidants to combat oxidative stress and aging, relieves infection, regenerate skin, slow aging, alleviate anxiety, antiviral properties, for cough, cold, influenza, and measles, normalize menstruation, promote healing, contains nutrients, and antioxidants ease menopause symptoms, reduce blood glucose levels, support healthy cholesterol levels, contains fatty acids that promote heart health, reduce cholesterol and blood pressure, lower the risk of heart disease, helps against digestive discomfort, lower blood sugar levels, antimicrobial effects, relieves anxiety and tension, improves immune system, decongests respiratory system, anti-inflammatory and antimicrobial effects help against infection, rich in Vitamins for proper health, antidepressant effects, sedative, and calming effects, soothing and nourishing properties to the skin, astringent and antiseptic, eases anxiety and sensitivity, treat stomach or intestinal problems, improves blood pressure or blood cholesterol, improve symptoms of cirrhosis, anti-inflammatory to regulate cholesterol, stimulate the cells of the liver, acts as an antispasmodic, kills bacteria, supports oral and skin health, combats pain and swelling, increases the amount of gamma-aminobutyric acid (GABA) in the brain, sedative effects help reduce anxiety and stress, treat insomnia, alleviate anxiety and stress, induce calming experience, have aphrodisiac effects, generally used to lower blood pressure, a natural relaxant, prevent heart disease and high blood pressure.

Example Composition HH

Example Composition HH comprises shilajit resin and the enrichment ingredients set forth in Table 39.

TABLE 39

| Ingredients |
| --- |
| cistus ladanifer |
| curry leaf |
| fragonia |
| kunzea |
| lemon myrtle |
| lime |
| manuka |
| mastic leaf |
| neroli |
| opoponax |
| petitgrain sur fleur |
| rhododendron |
| spruce eastern hemlock |
| wintergreen |
| ylang ylang |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition HH features numerous benefits to human health from the high-quality shilajit resin, cannabinoids, fatty acids, essential oils, terpenes, terpenoids, and/or essential fatty acids present therein. It is contemplated that certain combinations of the ingredients of Composition HH can elicit synergistic effects on one or more of the benefits of such ingredients. Composition HH can have, among others, one, some or all of the following benefits: wound healing, soothing sore throats, preventing tooth decay, and improving digestive issues, rich in nutrients like calcium, zinc, and magnesium contains antioxidants to combat oxidative stress and aging relieves infection, reduce inflammation and pain, manage diabetes symptoms, may health prevent cancer, reduce pain and inflammation, antimicrobial and antioxidant properties support immune health, treat skin conditions when applied topically, inflammation of the respiratory tract, arthritis pain, nerve pain, and feelings of tension, relaxing effect help relieve anxiety, stress, and even depression, antiseptic benefits against common infections, antispasmodic for coughs and respiratory congestion, boost immunity, reduce heart disease factors, aid in iron absorption, relieves joint pain, relieves headaches and respiratory conditions, relieves mental exhaustion, stress and tension, increase stomach juices and improve digestion, ease muscle tension and pain, stomach and intestinal ulcers, breathing problems, muscle aches and bacterial and fungal infection, treat dysentery, constipation and diarrhea, helps against morning sickness and nausea, antiseptic for skin use, expectorant, antispasmodic, relaxing effects on skin, aphrodisiac effects, lower blood pressure, antibacterial and mucolytic properties, support respiratory function, boost memory and focus, antiseptic and antibacterial properties, anti-inflammatory properties, and slows skin aging.

Example Composition II

Example Composition II can be an alternative to Example Composition HH, and comprises shilajit resin and the enrichment ingredients set forth in Table 40.

TABLE 40

| Ingredients |
| --- |
| alpha-pinene, beta-pinene, myrcene, 1,8-cineole, linalool, geraniol, terpinene4-ol, terpineol |
| Alpha-pinene, Viridiflorol, Ecualyptol |
| beta pinene, limonene, linalool |
| ctiral, neral and geranial, myrcene, linalool, citronellal, cyclocitral, methyl-heptenone |
| Leptospermone, α- and β-pinene, terpinen-4-ol, 1,8-cineole, ß-triketones, linalool- and eudesmol |
| Limonene, Pinene (Alpha/Beta), Delta-Cadinene, Cis-Ocimene, Trans-Beta-Farnesene, Alpha-Selinene. Others in smaller concentration include: Myrcene, Para-Cymene, Trans Beta-Ocimen, Linalyl Propionate, Bornyl Acetate, Citronellyl Acetate, Alpha Copaene, Beta-Caryophyllene, and many others in <1% |
| limonene; limonene/beta-pinene/gamma-terpinene; and limonene/linalyl acetate/linalool |
| Linalool, B-caryophyllene, germacrene D, benzyl acetate, methyl benzoate |
| linalool, elemol, geranyl acetate, myrcene, allo-ocimene, alpha-terpinene, (E)-beta-ocimene |
| linanlyl acetate, linalool, myrcene, geranyl acetate, alpha-terpineol |
| methyl salicylate, α-Pinene, Myrcene, delta-3-Carene, Limonene, 3,7-Guaiadiene, and delta-Cadinene |
| monoterpene hydrocarbons α-pinene, β-myrcene and camphen |
| shilajit manufactured under this patent |
| α-pinene, viridiflorol, borneol, trimethyl cyclohexanone, and camphene |
| α-pinene, β-pinene, camphene and limonene |
| β-Ocimene (82), (S,Z)-α-bisabolene (76), α-santalene (83), (e)-b-bergamotene, a-bergamotene, germacrene D, decanol |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition II features numerous benefits to human health from the high-quality shilajit resin, cannabinoids, fatty acids, essential oils, terpenes, terpenoids, and/or essential fatty acids present therein. It is contemplated that certain combinations of the ingredients of Composition II can elicit synergistic effects on one or more of the benefits of such ingredients. Composition II can have, among others, one, some or all of the following benefits: wound healing, soothing sore throats, preventing tooth decay, and improving digestive issues, rich in nutrients like calcium, zinc, and magnesium contains antioxidants to combat oxidative stress and aging relieves infection, reduce inflammation and pain, manage diabetes symptoms, may health prevent cancer, reduce pain and inflammation, antimicrobial and antioxidant properties support immune health, treat skin conditions when applied topically, inflammation of the respiratory tract, arthritis pain, nerve pain, and feelings of tension, relaxing effect help relieve anxiety, stress, and even depression, antiseptic benefits against common infections, antispasmodic for coughs and respiratory congestion, boost immunity, reduce heart disease factors, aid in iron absorption, relieves joint pain, relieves headaches and respiratory conditions, relieves mental exhaustion, stress and tension, increase stomach juices and improve digestion, ease muscle tension and pain, stomach and intestinal ulcers, breathing problems, muscle aches and bacterial and fungal infection, treat dysentery, constipation and diarrhea, helps against morning sickness and nausea, antiseptic for skin use, expectorant, antispasmodic, relaxing effects on skin, aphrodisiac effects, lower blood pressure, antibacterial and mucolytic properties, support respiratory function, boost memory and focus, antiseptic and antibacterial properties, anti-inflammatory properties, and slows skin aging.

Example Composition JJ

Example Composition JJ comprises shilajit resin and the enrichment ingredients set forth in Table 41.

TABLE 41

| Ingredients |
| --- |
| black pepper |
| cannabis |
| celery seed |
| clove bud |
| coconut pulp |
| cumin black |
| cypress |
| ginger |
| immortelle absolute |
| lippia javanica |
| orange |
| oregano |
| orris root |
| rose otto |
| yarrow blue |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition JJ features numerous benefits to human health from the high-quality shilajit resin, cannabinoids, fatty acids, essential oils, terpenes, terpenoids, and/or essential fatty acids present therein. It is contemplated that certain combinations of the ingredients of Composition JJ can elicit synergistic effects on one or more of the benefits of such ingredients. Composition JJ can have, among others, one, some or all of the following benefits: antioxidant levels support immunity, lower cholesterol, lower blood sugar levels, blood pressure-lowering, treat and eases tension and anxiety, prevents seizures, rich in vitamins, minerals, and antioxidants that support bone health, support blood formation, aid in blood sugar regulation, contains nutrients and minerals, high in antioxidants to combat oxidative stress, promote and assist liver health, highly nutritious, great source of calories and nutrients, help control blood sugar levels and blood pressure, rich in iron and antioxidants to fight oxidative stress, promotes health digestion, help with diabetes, treat fungal infections, improve hair health, help (e.g., prevent, reduce, treat) against varicose veins, rich source of antioxidants boosts immunity, lower high blood pressure, avoids heart disease, promotes healthy aging, promote liver healing and gallbladder health, reduce dyspepsia and edema, promote bile flow, treats cough, colds and headaches, treats digestive disorders, analgesic effect, rich source of antioxidants vitamins and minerals supports immunity and support against the development of serious diseases, antibacterial agent contains phytonutrients that helps against infection, a great source of antioxidants and vitamins, stimulates appetite, stimulates digestion and improve bile flow, eases headache and muscle pains, eases pain, stress and anxiety, antimicrobial properties help with infection, ease depressive episodes, boost immunity and inflammatory response, promote wound healing, prevent neurological diseases.

Example Composition KK

Example Composition KK can be an alternative to Example Composition JJ, and comprises shilajit resin and the enrichment ingredients set forth in Table 42.

TABLE 42

| Ingredients |
| --- |
| (+)-cis-γ-lrone (60), (+)-cis-α-irone (61) |
| a-pinene, camphene, sabinene, b-pinene, myrcene, d-3-carene, d-limonene, terpinolene, a-copaene, b-elemene, b-caryophyllene, a-cadinene, a-humulene, b-farnesene, valencene, and d-cadinene |
| alpha-pinene, beta-pinene, camphene, myrcene, γ-terpinene, zeta-cymene, terpinolene, linalool, pulegone, cuminal, 2,3-dihydrocuminal, myrtenal |
| B-pinene, terpineol |
| Beta-caryophyllene, Beta-pinene, Humulene, Limonene, Linalool, Myrcene |
| carvacrol, thymol, γ-terpinene and p-cymene; while terpinen-4-ol, linalool, β-myrcene, trans-sabinene hydrate, and β-caryophyllene |
| caryophyllene, carvone, ipsenone, ipsdienone, limonene, linalool, myrcene, myrcenone, ocimenone, p-cymene, piperitenone, sabinene, and tagetenone |
| caryopyllene |
| d-limonene, selinene, sesquiterpene alcohols |
| lactones |
| Linalool, citronellol, geraniol, alkenes, nerol, 2-phenylethanol |
| neryl acetate, rosifoliol, neryl propionate, y-curcumene, linalool, nerol, rosifoliol, geranyl propionate, ar-curcumene, italidione, alpha-eudesmol, limonene |
| pinene, caryophyllene |
| Sabinene, β-Pinene, Chamazulene |
| Zingiberene, β-Bisabolene, Cineol, Geraniol, Linalool, Citral, Borneol, α-Farnesene, β-Phellandrene and Curcumene |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition KK features numerous benefits to human health from the high-quality shilajit resin, cannabinoids, fatty acids, essential oils, terpenes, terpenoids, and/or essential fatty acids present therein. It is contemplated that certain combinations of the ingredients of Composition KK can elicit synergistic effects on one or more of the benefits of such ingredients. Composition KK can have, among others, one, some or all of the following benefits: antioxidant levels support immunity, lower cholesterol, lower blood sugar levels, blood pressure-lowering, treat and eases tension and anxiety, prevents seizures, rich in vitamins, minerals, and antioxidants that support bone health, support blood formation, aid in blood sugar regulation, contains nutrients and minerals, high in antioxidants to combat oxidative stress, promote and assist liver health, highly nutritious, great source of calories and nutrients, help control blood sugar levels and blood pressure, rich in iron and antioxidants to fight oxidative stress, promotes health digestion, help with diabetes, treat fungal infections, improve hair health, help (e.g., prevent, reduce, treat) against varicose veins, rich source of antioxidants boosts immunity, lower high blood pressure, avoids heart disease, promotes healthy aging, promote liver healing and gallbladder health, reduce dyspepsia and edema, promote bile flow, treats cough, colds and headaches, treats digestive disorders, analgesic effect, rich source of antioxidants vitamins and minerals supports immunity and support against the development of serious diseases, antibacterial agent contains phytonutrients that helps against infection, a great source of antioxidants and vitamins, stimulates appetite, stimulates digestion and improve bile flow, eases headache and muscle pains, eases pain, stress and anxiety, antimicrobial properties help with infection, ease depressive episodes, boost immunity and inflammatory response, promote wound healing, prevent neurological diseases.

Example Composition LL

Example Composition LL comprises shilajit resin and the enrichment ingredients set forth in Table 43.

TABLE 43

| Ingredients |
|---|
| cistus ladanifer sp. |
| clementine |
| douglas fir |
| elemi |
| galanga |
| hemp |
| hyssop decumbens |
| innula |
| mastic leaf |
| nagarmotha |
| peppermint |
| petitgrain sur fleur |
| rhododendron |
| Spearmint |
| tea tree |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition LL features numerous benefits to human health from the high-quality shilajit resin, cannabinoids, fatty acids, essential oils, terpenes, terpenoids, and/or essential fatty acids present therein. It is contemplated that certain combinations of the ingredients of Composition LL can elicit synergistic effects on one or more of the benefits of such ingredients. Composition LL can have, among others, one, some or all of the following benefits: relaxing effect help relieve anxiety, stress, and even depression, antiseptic benefits against common infections, antispasmodic for coughs and respiratory congestion, soothing antiseptic benefits for respiratory tract diseases relieve skin conditions, can be used for parasites, improve digestion and oral health, promote focus, lessen allergic reaction. reduce inflammation and pain, manage diabetes symptoms, may health prevent cancer, rich source of antioxidants to support immunity, reduce pain and inflammation, help improve fertility, antiseptic properties for skin and mouth may boost wound healing, antifungal, and antibacterial properties, prevent acne and nail fungus, loosen mucous and relieve bronchial congestion and spasms, relieves cold sores, stimulates health growth, helps with indigestion, helps manage obesity, rich in antioxidants and nutrients, helps reduce inflammation, and anticancer compounds help against cancer, contains fatty acids that promote heart health, reduce cholesterol and blood pressure, and lower the risk of heart disease, antiseptic for skin cuts, bruises, and burns, treat cold and cough symptoms, contains electrolytes, improves digestion and promotes health hormone secretion, stimulates nervous response, relieves pain, anti-inflammatory response, antiseptic and antibacterial properties, anti-inflammatory, and slows skin aging, stomach and intestinal ulcers, helps breathing problems, relieves muscle aches, treats or reduces symptoms of bacterial and fungal infection, help balance hormones, lower blood sugar, and improve digestion.

Example Composition MM

Example Composition MM can be an alternative to Example Composition LL, and comprises shilajit resin and the enrichment ingredients set forth in Table 44.

TABLE 44

| Ingredients |
|---|
| 1,8-cineole, exo-2-hydroxy-l,8-cineole acetate, -caryophyllene,-and-pinenes, -bisabolene, chavicol, limonene, 4-terpineol,, chavicol acetate, methyl eugenol |
| alpha-cyperone, beta-selinene, cyperene, cyperotundone, patchoulenone, sugeonol, kobusone, iskobusone |
| enthol, menthone, menthofuran, isomenthone, (E)-caryophyllene, 1,8-cineole, linalool, limonene, carvone, pulegone and α-terpineol |
| inusoniolide, 4-O-dihydroinusoniolide and 9β-hydroxyparthenolide, inulin, |
| limonene, camphene, and isobornyl acetate |
| Limonene, Pinene (Alpha/Beta), Delta-Cadinene, Cis-Ocimene, Trans-Beta-Farnesene, Alpha-Selinene. Others in smaller concentration include: Myrcene, Para-Cymene, Trans Beta-Ocimen, Linalyl Propionate, Bornyl Acetate, Citronellyl Acetate, Alpha Copaene, Beta-Caryophyllene, and many others in <1% |
| linanlyl acetate, linalool, myrcene, geranyl acetate, alpha-terpineol |
| monoterpene hydrocarbons α-pinene, β-myrcene and camphen |
| Myrcene, D-limonene, beta-caryophyllene, linalool, terpineol, fenchol, borneol, caryophyllene-oxide, camphene, gernaiol |
| phellandrene, dipentene |
| Pinene, beta Pinene, Carvone, Cineole, Caryophyllene, Linalool, Limolene, Menthol, Myrcene |
| pinene, limonene, myrcene, humulene, farnesol and caryophyllene |
| terpinolene, 1,8-cineole, terpinen-4-ol |
| α-pinene, Sabinene, β-pinene, Limonene, Pinocamphone, iso-pinocamphone, myrtenyl methyl ether, β-bourbonene, β-caryophyllene, allo-aromadendrene, germacrene-D, Elemol, Spathulenol, β-phellandrene, (E)-β-ocimene, γ-terpinene, Linalool, Pinocarveol, Myrtenol, methyl eugenol, α-gurjunene, Bicyclogermacrene, |
| α-pinene, viridiflorol, borneol, trimethyl cyclohexanone, and camphene |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition MM features numerous benefits to human health from the high-quality shilajit resin, cannabinoids, fatty acids, essential oils, terpenes, terpenoids, and/or essential fatty acids present therein. It is contemplated that certain combinations of the ingredients of Composition MM can elicit synergistic effects on one or more of the benefits of such ingredients. Composition MM can have, among others, one, some or all of the following benefits: relaxing effect help relieve anxiety, stress, and even depression, antiseptic benefits against common infections, antispasmodic for coughs and respiratory congestion, soothing antiseptic benefits for respiratory tract diseases relieve skin conditions, can be used for parasites, improve digestion and oral health, promote focus, lessen allergic reaction. reduce inflammation and pain, manage diabetes symptoms, may health prevent cancer, rich source of antioxidants to support immunity, reduce pain and inflammation, help improve fertility, antiseptic properties for skin and mouth may boost wound healing, antifungal, and antibacterial properties, prevent acne and nail fungus, loosen mucous and relieve bronchial congestion and spasms, relieves cold sores, stimulates health growth, helps with indigestion, helps manage obesity, rich in antioxidants and nutrients, helps reduce inflammation, and anticancer compounds help against cancer, contains fatty acids that promote heart health, reduce cholesterol and blood pressure, and lower the risk of heart disease, antiseptic for skin cuts, bruises, and burns, treat cold and cough symptoms, contains electrolytes, improves digestion and promotes health hormone secretion, stimulates nervous response, relieves pain, anti-inflammatory response, antiseptic and antibacterial properties, anti-inflammatory, and slows skin aging, stomach and intestinal ulcers, helps breathing problems, relieves muscle aches, treats or reduces symptoms of bacterial and fungal infection, help balance hormones, lower blood sugar, and improve digestion.

Example Composition NN

Example Composition NN comprises shilajit resin and the enrichment ingredients set forth in Table 45.

TABLE 45

| Ingredients |
|---|
| amyris |
| anethi |
| arnica |
| choya loban |
| clove bud |
| cocoa bean |
| copaiba balsam |
| cumin |
| grapefruit |
| hyssop decumbens |
| jasmine |
| marjoram |
| Thyme |
| tulsi |
| valerian |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition NN features numerous benefits to human health from the high-quality shilajit resin, cannabinoids, fatty acids, essential oils, terpenes, terpenoids, and/or essential fatty acids present therein. It is contemplated that certain combinations of the ingredients of Composition NN can elicit synergistic effects on one or more of the benefits of such ingredients. Composition NN can have, among others, one, some or all of the following benefits: rich antioxidant content and vitamin C promote immune health and healthy aging, prevent insulin resistance and diabetes, when inhaled, highly effective against various respiratory problems such as bronchitis, asthma, laryngitis, asthma, coughs and others, reduce fever and have analgesic properties, lower blood glucose, antidepressant effects, aphrodisiac effect enhance libido, sedative effects help with sleep, increases the amount of gamma-aminobutyric acid (GABA) in the brain, sedative effects help reduce anxiety and stress, treat insomnia, reduce inflammation, and reduce infection, may help with alopecia areata, clear skin, and acne, reduce inflammation and provide pain relief, lower blood pressure, rich in folate and minerals, beneficial effects for women with PCOS, reduces anxiety, anti-inflammatory, antimicrobial effects, contains nutrients and minerals, high in antioxidants to combat oxidative stress, promote and assist liver health, rich in polyphenols and flavonoids to help lower blood pressure, cholesterol and sugars, reduce risk of diabetes, improve circulation, fight oxidative stress, promotes health digestion, help with diabetes, helps against loss of appetite, helps prevent or relieve flatulence, and digestive issues help against UTI, flavonoids help reduce the risk of heart disease, regenerate skin, slow aging, alleviate anxiety, loosen mucous and relieve bronchial congestion and spasms, relieves cold sores, can be used topical to treat bruises, wounds, phlebitis, inflammation, insect bites, reduce swelling and muscle pain.

Example Composition OO

Example Composition OO can be an alternative to Example Composition NN, and comprises shilajit resin and the enrichment ingredients set forth in Table 46.

TABLE 46

| Ingredients |
|---|
| 2,5-dimethoxy-p-cymene, cumene, thymol methyl ether, 2,6-diisopropylanisole, decanal, 1,2,2,3-tetramethylcyclopent-3-enol, α-pinene oxide, β-maaliene, E-α-bergamotene, lippifoli-1(6)-en-5-one, 7-epi-silphiperfol-5-ene, α-isocomene, 2,5-dimetoxy-p-cymene, E-caryophyllene, and caryophyllene oxide |
| a-cubebene, a-copaene, b-elemene, b-caryophyllene, y-elemene, a-bergamotene, a-humulene, trans-cadina-1(6),4 diene, germacrene D, b-bisabolene, a-cadiene |
| a = copaene, b-caryophyllene, |
| alpha-pinene, beta-pinene, camphene, myrcene, γ-terpinene, zeta-cymene, terpinolene, linalool, pulegone, cuminal, 2,3-dihydrocuminal, myrtenal |
| ar-curcumene, α,β,γ-patchoulenes, patchouli alcohol, β-sitosterol, valeranone, maali-oxide, maaliol, calarene, β-bergamotene |
| carvacrol, thymol, linalool, cineol, camphor borneol |
| caryophyllene oxide, linalool, myrcene, methyl chavicol, gamma caryophyllene, alpha humulene, thymol, cineole, methyl-eugenol, camphor |
| caryopyllene |
| limonen, myrcene, a-pinene, sabinene, geraniol, citronellal, linalool, decyl acetate, neryl acetate, terpinen-4-ol, Nootkatone |
| Linalool, myrcene and ocimene |
| phellandrene, dill ether, limonene, p-cymene |
| pinene, sabinene, terpinene, limonene and linalool |
| Valerianol, B-eudesmol, A-eudesmol, Elemol, Y-eudismol |
| α-pinene, Sabinene, β-pinene, Limonene, Pinocamphone, iso-pinocamphone, myrtenyl methyl ether, β-bourbonene, β-caryophyllene, allo-aromadendrene, germacrene-D, Elemol, Spathulenol, β-phellandrene, (E)-β-ocimene, γ-terpinene, Linalool, Pinocarveol, Myrtenol, methyl eugenol, α-gurjunene, Bicyclogermacrene, |
| β-caryophyllene, trans-nerolidol, (E,E)-α-farnesene |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition OO features numerous benefits to human health from the high-quality shilajit resin, cannabinoids, fatty acids, essential oils, terpenes, terpenoids, and/or essential fatty acids present therein. It is contemplated that certain combinations of the ingredients of Composition OO can elicit synergistic effects on one or more of the benefits of such ingredients. Composition OO can have, among others, one, some or all of the following benefits: rich antioxidant content and vitamin C promote immune health and healthy aging, prevent insulin resistance and diabetes, when inhaled, highly effective against various respiratory problems such as bronchitis, asthma, laryngitis, asthma, coughs and others, reduce fever and have analgesic properties, lower blood glucose, antidepressant effects, aphrodisiac effect enhance libido, sedative effects help with sleep, increases the amount of gamma-aminobutyric acid (GABA) in the brain, sedative effects help reduce anxiety and stress, treat insomnia, reduce inflammation, and reduce infection, may help with alopecia areata, clear skin, and acne, reduce inflammation and provide pain relief, lower blood pressure, rich in folate and minerals, beneficial effects for women with PCOS, reduces anxiety, anti-inflammatory, antimicrobial effects, contains nutrients and minerals, high in antioxidants to combat oxidative stress, promote and assist liver health, rich in polyphenols and flavonoids to help lower blood pressure, cholesterol and sugars, reduce risk of diabetes, improve circulation, fight oxidative stress, promotes health digestion, help with diabetes, helps against loss of appetite, helps prevent or relieve flatulence, and digestive issues help against UTI, flavonoids help reduce the risk of heart disease, regenerate skin, slow aging, alleviate anxiety, loosen mucous and relieve bronchial congestion and spasms, relieves cold sores, can be used topical to treat bruises, wounds, phlebitis, inflammation, insect bites, reduce swelling and muscle pain.

Example Composition PP

Example Composition PP comprises shilajit resin and the enrichment ingredients set forth in Table 47.

TABLE 47

| Ingredients |
| --- |
| ambrette |
| black pepper |
| cannabis |
| chamomile |
| choya loban |
| copaiba balsam |
| fenugreek |
| Liquidambar |
| nagarmotha |
| plai |
| sandalwood |
| Spearmint |
| star anise |
| Tulip absolute |
| zdravets |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition PP features numerous benefits to human health from the high-quality shilajit resin, cannabinoids, fatty acids, essential oils, terpenes, terpenoids, and/or essential fatty acids present therein. It is contemplated that certain combinations of the ingredients of Composition PP can elicit synergistic effects on one or more of the benefits of such ingredients. Composition PP can have, among others, one, some or all of the following benefits: can be used to lower blood pressure, natural relaxant, prevent heart disease and high blood pressure, can be chewed for sore throat, cough, asthma and stomach problems, help balance hormones, lower blood sugar and improve digestion, when inhaled, highly effective against various respiratory problems such as bronchitis, asthma, laryngitis, asthma, coughs and others, blood pressure-lowering, treat and eases tension and anxiety, prevents seizures, prevents stomach and intestinal disorders with cramps, prevents loss of appetite, and prevents stomach cancer, antioxidant levels support immunity, may lower cholesterol, may lower blood sugar levels, clear skin, and acne, reduce inflammation and provide pain relief, lower blood pressure, rich in antioxidant terpenes that help boost immunity and offer anti-inflammatory, anti-microbial properties, lowering blood sugar levels, boosting testosterone, and increasing milk production in breastfeeding mothers, relieves indigestion, and its effects, promote healing and pain relief, relieve anxiety, manage the common cold, and infections (UTI), helps manage anxiety, stimulates health growth, helps with indigestion, helps manage obesity, stimulate immunity and vitality, antimicrobial compounds fight infection, soothes muscle pain, diuretic, antiseptic, anti-inflammatory benefits.

Example Composition QQ

Example Composition QQ can be an alternative to Example Composition PP, and comprises shilajit resin and the enrichment ingredients set forth in Table 48.

TABLE 48

| Ingredients |
| --- |
| a-cubebene, a-copaene, b-elemene, b-caryophyllene, y-elemene, a-bergamotene, a-humulene, trans-cadina-1(6),4 diene, germacrene D, b-bisabolene, a-cadiene |
| a-pinene, d-limonene, beta-ocimene, 2,6-octadiene-2,6-dimethyl, longifolene, a-farnesene |
| a = copaene, b-caryophyllene, |
| alpha-cyperone, beta-selinene, cyperene, cyperotundone, patchoulenone, sugeonol, kobusone, iskobusone |
| b-pinene, 2,5-dimethylpyrazine, 6-methyl-5-hep-ten-2-one, camphor, 3-octen-2-one, b-caryophyllene, neryl acetate, a-selinene, geranial |
| Beta-caryophyllene, Beta-pinene, Humulene, Limonene, Linalool, Myrcene |
| farnesol acetate, ambrettolide, Cis-a-Farnesene, Aromandendrene, Bicyclo[3.1.1]hept-2-ene, 2,6-dimethyl-6(4-methyl-3-pentenyl)-, a-Farnesene, Nerolidyl acetate, a-Guaiene, 1,3,6,10-Cyclotetradecatetraene, 3,7,11-trimethyl-14-(1-methylethyl) |
| Germacrone, Beta-elemene, Germacrene B, Gamma-Elemene, Gamma Terpinene, A, B Pinene |
| Pinene, beta Pinene, Carvone, Cineole, Caryophyllene, Linalool, Limolene, Menthol, Myrcene |
| pinene, caryophyllene |
| sabinene, y-terpinene, a-terpinene, terpinen (E)-1-(3,4-dimethoxyphenol) butadiene4-ol |
| shilajit manufactured under this patent |
| terpinen-4-ol, α-terpineol, α-pinene, sabinene |
| α- & β-santalols (90%), α- & β santalenes |
| α-bisabolol, chamazulene, farnesene, α-pinene, lactones |
| α-Pinene, β-Pinene, cis-Anethole, trans-Anethole, Limonene, Linalool |

It is contemplated that ingredients can be removed. It is contemplated that ingredients can be added from other Examples described herein and/or from the ingredients listed in Tables 1-4. Further, it is contemplated that any other suitable cannabinoids, fatty acids, essential oils, terpenes and/or terpenoids can be included in such composition.

Example composition QQ features numerous benefits to human health from the high-quality shilajit resin, cannabinoids, fatty acids, essential oils, terpenes, terpenoids, and/or essential fatty acids present therein. It is contemplated that certain combinations of the ingredients of Composition QQ can elicit synergistic effects on one or more of the benefits of such ingredients. Composition QQ can have, among others, one, some or all of the following benefits: can be used to lower blood pressure, natural relaxant, prevent heart disease and high blood pressure, can be chewed for sore throat, cough, asthma and stomach problems, help balance hormones, lower blood sugar and improve digestion, when inhaled, highly effective against various respiratory problems such as bronchitis, asthma, laryngitis, asthma, coughs and others, blood pressure-lowering, treat and eases tension and anxiety, prevents seizures, prevents stomach and intestinal disorders with cramps, prevents loss of appetite, and prevents stomach cancer, antioxidant levels support immunity, may lower cholesterol, may lower blood sugar levels, clear skin, and acne, reduce inflammation and provide pain relief, lower blood pressure, rich in antioxidant terpenes that help boost immunity and offer anti-inflammatory, anti-microbial properties, lowering blood sugar levels, boosting testosterone, and increasing milk production in breastfeeding mothers, relieves indigestion, and its effects, promote healing and pain relief, relieve anxiety, manage the common cold, and infections (UTI), helps manage anxiety, stimulates health growth, helps with indigestion, helps manage obesity, stimulate immunity and vitality, antimicrobial compounds fight infection, soothes muscle pain, diuretic, antiseptic, anti-inflammatory benefits, In another aspect of the disclosure, a ready to consume emulsified product is provided, comprising a processed mineral pitch resin, and at least one enriching ingredient, wherein the at least one enriching ingredient comprises a set of essential oils, the set of essential oils comprising a grapefruit oil and at least one of a clementine oil, a lemon oil, a cardamom oil, a ginger oil, a coffee oil, a cocoa oil, a bergamot oil, a manuka oil, a lemon myrtle oil, a cinnamon oil, a cardamom oil, a zdravetz oil, a damiana oil, an orange oil, and a coffee CO2 oil.

In another aspect of the disclosure, a ready to consume emulsified product is provided, comprising a processed mineral pitch resin, and at least one enriching ingredient, wherein the at least one enriching ingredient comprises a set of essential oils, the set of essential oils comprising an orange oil and at least one of a lavender oil, a roman chamomile oil, a rose geranium oil, a manuka oil, a chamomile oil, a ginger oil, a cinnamon oil, a petitgrain sur fleur oil, a clementine oil, a combava lime oil, a black pepper oil, a cardamom oil, a cocoa bean oil, a zdravetz oil, a ginger oil, a damiana oil, and a grapefruit oil.

In another aspect of the disclosure, a ready to consume emulsified product is provided, comprising a processed mineral pitch resin, and at least one enriching ingredient, wherein the at least one enriching ingredient, wherein the at least one enriching ingredient comprises a set of essential oils, the set of essential oils comprising a cacao oil and at least one of a vanilla oil, a rose oil, a lemon oil, a cinnamon oil, and a ginger oil.

In some embodiments, the product is an orally consumable product. In some embodiments, the product stays emulsified with no visible separation of oil and resin when stored at 25 degrees Celsius for a period of at least one month. In some embodiments, the at least one enriching ingredient comprises no more than 10% of the mineral pitch resin product by weight. In some embodiments, the product is a paste that provides a reading of between 5-8 on the Hegman gage. In some embodiments, the at least one enriching ingredient further comprises a cannabinoid. In some embodiments, the at least one enriching ingredient further comprises a fatty acid. In some embodiments, the at least one enriching ingredient further comprises at least one of a terpene and a terpenoid. In some embodiments, the product comprises no greater than 3 mg/kg lead, no greater than 6 mg/kg arsenic, no greater than 0.5 mg/kg cadmium, no greater than 1 mg/kg mercury, less than 10 GFU/g microbiological pathogens, a moisture level by mass of 0.001 up to 60%, no less than 1% glycine; and at least 1 fatty acid.

In another aspect of the disclosure, a ready to consume emulsified product is provided, consisting essentially of a processed mineral pitch resin and enriching ingredients, the enriching ingredients consist essentially of a cardamom oil, a damiana oil, a cocoa bean oil, a zdravetz oil, and at least one of a cinnamon oil, an orange oil, a ginger oil, and a grapefruit oil. In another aspect of the disclosure, a ready to consume emulsified product is provided, comprising a processed mineral pitch resin and enriching ingredients, the enriching ingredients comprising a cardamom oil, a damiana oil, a cocoa bean oil, a zdravetz oil, and at least one of a cinnamon oil, an orange oil, a ginger oil, and a grapefruit oil.

In another aspect of the disclosure, a ready to consume emulsified product is provided, consisting essentially of a processed mineral pitch resin and enriching ingredients, the enriching ingredients consist essentially of at least one cannabinoid, a cardamom oil, a damiana oil, a cocoa bean oil, a zdravetz oil, and at least one of a cinnamon oil, an orange oil, a ginger oil, and a grapefruit oil. In another aspect of the disclosure, a ready to consume emulsified product is provided, comprising a processed mineral pitch resin and enriching ingredients, the enriching ingredients comprising at least one cannabinoid, a cardamom oil, a damiana oil, a cocoa bean oil, a zdravetz oil, and at least one of a cinnamon oil, an orange oil, a ginger oil, and a grapefruit oil.

In another aspect of the disclosure, a ready to consume emulsified product is provided, consisting essentially of a processed mineral pitch resin and enriching ingredients, the enriching ingredients consist essentially of at least one cannabinoid, at least one fatty acid, a cardamom oil, a damiana oil, a cocoa bean oil, a zdravetz oil, and at least one of a cinnamon oil, an orange oil, a ginger oil, and a grapefruit oil. In another aspect of the disclosure, a ready to consume emulsified product is provided, comprising a processed mineral pitch resin and enriching ingredients, the enriching ingredients comprising at least one cannabinoid, at least one fatty acid, a cardamom oil, a damiana oil, a cocoa bean oil, a zdravetz oil, and at least one of a cinnamon oil, an orange oil, a ginger oil, and a grapefruit oil.

In another aspect of the disclosure, a ready-to-consume emulsified product is provided, comprising a processed mineral pitch resin and enriching ingredients, the enriching ingredients comprising at least one cannabinoid, at least one fatty acid, at least one oil, and at least one component resulting from the emulsification process. In another aspect of the disclosure, a ready-to-consume emulsified product is provided, consisting essentially of a processed mineral pitch resin and enriching ingredients, the enriching ingredients consisting essentially of at least one cannabinoid, at least one fatty acid, at least one oil, and at least one component resulting from the emulsification process. In another aspect of the disclosure, a ready-to-consume emulsified product is provided, comprising a processed mineral pitch resin and enriching ingredients, the enriching ingredients consisting essentially of at least one cannabinoid, at least one fatty acid, at least one oil, and at least one component resulting from the emulsification process. Any suitable number of cannabinoids, fatty acids, and oils are contemplated herein, including any of the cannabinoids, fatty acids, and oils set forth in this application.

It should be appreciated that the at least one component resulting from the emulsification process can be present in the emulsion (e.g., resulting from combining the mineral pitch resin with one of the enriching ingredients due to a predetermined shear force or temperature range) that is not present in any of the mineral pitch resin or enriching ingredients alone. Without wishing to be bound by any particular theory, it is contemplated that at least two molecules of the ingredients are bound chemically or physically, catalyzed (e.g., by shear force and heat), or coagulated. The at least two molecules can comprise, among other things, molecule(s) of the mineral pitch resin and molecule(s) of an essential oil, molecule(s) of the mineral pitch resin and molecule(s) of a fatty acid, molecule(s) of the mineral pitch resin and molecule(s) of a cannabinoid, molecule(s) of the mineral pitch resin and molecule(s) of a terpene, molecule(s) of the mineral pitch resin and molecule(s) of a terpenoid, molecule(s) of the first and second essential oils, molecule (s) of the first and second fatty acids, molecule(s) of the first and second cannabinoids, molecule(s) of the first and second terpenes, molecule(s) of the first and second terpenoids, molecule(s) of an essential oil and molecule(s) of any other enriching ingredient, molecule(s) of a fatty acid and molecule(s) of any other enriching ingredient, molecule(s) of a cannabinoid and molecule(s) of any other enriching ingredient, molecule(s) of a terpene and molecule(s) of any other enriching ingredient, molecule(s) of a terpenoid and molecule(s) of any other enriching ingredient. The products described herein have a highly unique organoleptic profile, and an ability to produce beneficial effects not present in shilajit resin alone, for example, to change a mood and shift brain frequencies relatively quickly. Without wishing to be bound by any particular theory, it is contemplated that certain combinations of terpenes in certain combinations of essential oils as described herein may contribute to or cause the change in the organoleptic profile and shift the brain frequencies, for example, with the formation of diterpenes. Whether diterpenes or other terpenes form can depend on one or more factors such as reactivity, catalysts or enzymes present, conditions such as temperature and pressure, the availability of precursor compounds, and other factors. Olfactory stimulation is an alternative way to pass information to the brain, and can be much quicker than through the mouth. While genuine Shilajit generally has an unpleasant smell and taste, the products described herein and the products produced using the methods described herein have a pleasant smell and taste and results in quicker and enhanced benefits. Further, where enriching ingredients comprise one or more essential oils, it has been found that the essential oil(s) are trapped in the structure and stay preserved without going bad in terms of the smell. The emulsion form may interfere with oxygenation and deterioration, and improve viscosity.

In another aspect of the disclosure, a ready to consume emulsified product is provided, comprising a processed mineral pitch resin and enriching ingredients, the enriching ingredients comprising at least four terpenes. In another aspect of the disclosure, a ready to consume emulsified product is provided, consisting essentially of a processed mineral pitch resin and enriching ingredients, the enriching ingredients consisting essentially of at least four terpenes. In another aspect of the disclosure, a ready to consume emulsified product is provided, comprising a processed mineral pitch resin and enriching ingredients, the enriching ingredients consisting essentially of at least four terpenes.

In another aspect of the disclosure, a ready to consume emulsified product is provided comprising a processed mineral pitch resin and enriching ingredients comprising at least two cannabinoids. In another aspect of the disclosure, a ready to consume emulsified product is provided consisting essentially of a processed mineral pitch resin and enriching ingredients comprising at least two cannabinoids. In another aspect of the disclosure, a ready to consume emulsified product is provided consisting essentially of a processed mineral pitch resin and enriching ingredients consisting essentially of at least two cannabinoids.

In another aspect of the disclosure, a ready to consume emulsified product is provided comprising a processed mineral pitch resin and enriching ingredients, the enriching ingredients comprising at least two fatty acids. In another aspect of the disclosure, a ready to consume emulsified product is provided consisting essentially of a processed mineral pitch resin and enriching ingredients, the enriching ingredients comprising at least two fatty acids. In another aspect of the disclosure, a ready to consume emulsified product is provided consisting essentially of a processed mineral pitch resin and enriching ingredients, the enriching ingredients consisting essentially of at least two fatty acids.

In another aspect of the disclosure, a ready to consume emulsified mineral pitch product is provided comprising at least one of the following: 1,8-cineole (CAS #470-82-6), α-Bisabolol (CAS #23089-26-1), α-Pinene (CAS #80-56-8), α-terpinyl acetate (CAS #80-26-2), β-Pinene (CAS #127-91-3), β-Sesquiphellandrene (CAS #20307-83-9), Cafestol (CAS #469-83-0), Caffeine (CAS #58-08-2), Caryophyllene (CAS #87-44-5), Chamazulene (CAS #529-05-5), Citral (CAS #5392-40-5), Citronellol (CAS #106-22-9), Cinnamaldehyde (CAS #104-55-2), Curcumene (CAS #644-30-4), Eugenol (CAS #97-53-0), Flavesone (CAS #Not available), Geraniol (CAS #106-24-1), Geranyl acetate (CAS #105-87-3), Germacrone (CAS #6902-91-6), Isoleptospermone (CAS #Not available), Leptospermone (CAS #567-75-9), Limonene (CAS #5989-27-5), Linalool (CAS #78-70-6), Linalyl acetate (CAS #115-95-7), Myrcene (CAS #123-35-3), Nerol (CAS #106-25-2), Pinene (CAS #1330-16-1), Sabinene (CAS #3387-41-5), Terpinolene (CAS #586-62-9), Theobromine (CAS #83-67-0), Zdravets lactone (CAS #Not available), γ-Terpinene (CAS #99-85-4), and Zingiberene (CAS #495-60-3). The terpenes and terpenoids are of natural or synthetic origin.

In another aspect of the disclosure, a ready to consume emulsified mineral pitch product is provided comprising at least one of the following: 1,8-cineole, α-Bisabolol, α-Pinene, α-terpinyl acetate, β-Pinene, β-Sesquiphellandrene, Cafestol, Caffeine, Caryophyllene, Chamazulene, Citral, Citronellol, Cinnamaldehyde, Curcumene, Eugenol, Flavesone, Geraniol, Geranyl acetate, Germacrone, Isoleptospermone, Leptospermone, Limonene, Linalool, Linalyl acetate, Myrcene, Nerol, Pinene, Sabinene, Terpinolene, Theobromine, Zdravets lactone, γ-Terpinene, and Zingiberene. The terpenes and terpenoids are of natural or synthetic origin.

In another aspect of the disclosure, a ready to consume emulsified mineral pitch product is provided that is usable for olfactory stimulation, producing a brainwave change within 0.5 to 3 HZ, 3 to 8 HZ, 8 to 13 Hz, 12 to 15 Hz, 16 to 31 Hz, 32 to 100 Hz ranges.

In another aspect of the disclosure, a ready to consume emulsified mineral pitch product is provided that is usable for olfactory stimulation, producing a brainwave change in a hyman within 0.5 to 3 HZ, 3 to 8 HZ, 8 to 13 Hz, 12 to 15 Hz, 16 to 31 Hz, 32 to 100 Hz ranges within up to 60, up to 3600, up to 43200 seconds.

Thus, specific embodiments and applications of enriched mineral pitch resin products and methods of manufacturing enriched mineral pitch resin products for human consumption have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The word "exemplary" is used herein to mean "serving as an example, instance, or illustration." Any aspect described herein as "exemplary" is not necessarily to be construed as preferred or advantageous over other aspects. Unless specifically stated otherwise, the term "some" refers to one or more.

All structural and functional equivalents to the elements of the various aspects described throughout this disclosure that are known or later come to be known to those of ordinary skill in the art are expressly incorporated herein by reference and are intended to be encompassed by the claims.

The accompanying claims and their equivalents are intended to cover such forms or modifications as would fall within the scope of the disclosure. The features and attributes of the specific example embodiments of the enriched shilajit products and related methods disclosed above may be combined in different ways to form additional embodiments, all of which fall within the scope of the disclosure.

Although the present disclosure provides certain example embodiments and applications, other embodiments that are apparent to those of ordinary skill in the art, including embodiments which do not provide all of the features and advantages set forth herein, are also within the scope of this disclosure.

What is claimed is:

1. An emulsified mineral pitch resin consisting essentially of grapefruit oil, orange oil, cannabidiol oil, cacao oil and mineral pitch resin.

2. The emulsified mineral pitch resin of claim 1, wherein a particulate size within the emulsion is in the range of 1-10 nm.

3. An emulsified mineral pitch resin consisting essentially of lemon oil, orange oil, cacao oil, cannabidiol oil and mineral pitch resin.

4. The emulsified mineral pitch resin of claim 3, wherein a particulate size within the emulsion is in the range of 1-10 nm.

5. An emulsified mineral pitch resin consisting essentially of lavender oil, tangerine oil, clementine oil and mineral pitch resin.

6. The emulsified mineral pitch resin of claim 5, wherein a particulate size within the emulsion is in the range of 1-10 nm.

* * * * *